United States Patent
Wengrenovich et al.

(10) Patent No.: US 12,129,525 B2
(45) Date of Patent: Oct. 29, 2024

(54) OPTIMIZED GAMMA-PRIME STRENGTHENED AUSTENITIC TRIP STEEL AND DESIGNING METHODS OF SAME

(71) Applicant: NORTHWESTERN UNIVERSITY, Evanston, IL (US)

(72) Inventors: Nicholas J. Wengrenovich, Evanston, IL (US); Gregory B. Olson, Riverswood, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 266 days.

(21) Appl. No.: 17/568,835

(22) Filed: Jan. 5, 2022

(65) Prior Publication Data
US 2022/0195547 A1     Jun. 23, 2022

Related U.S. Application Data

(62) Division of application No. 15/483,559, filed on Apr. 10, 2017, now Pat. No. 11,242,576.

(Continued)

(51) Int. Cl.
| | |
|---|---|
| *G01N 33/48* | (2006.01) |
| *C21D 6/00* | (2006.01) |
| *C21D 6/02* | (2006.01) |
| *C21D 7/13* | (2006.01) |
| *C22C 33/00* | (2006.01) |
| *C22C 38/06* | (2006.01) |

(Continued)

(52) U.S. Cl.
CPC ............... *C21D 6/02* (2013.01); *C21D 6/004* (2013.01); *C21D 7/13* (2013.01); *C22C 33/00* (2013.01); *C22C 38/06* (2013.01); *C22C 38/44* (2013.01); *C22C 38/46* (2013.01); *C22C 38/50* (2013.01); *C22C 38/54* (2013.01); *G16C 60/00* (2019.02); *C21D 2211/001* (2013.01); *C21D 2211/004* (2013.01); *G06F 30/27* (2020.01); *G06F 2113/26* (2020.01)

(58) Field of Classification Search
CPC ............ C21D 6/02; C21D 6/004; C21D 7/13; C21D 2211/001; C21D 2211/004; C22C 33/00; G16C 60/00; G06F 2113/26
See application file for complete search history.

(56) References Cited

PUBLICATIONS

Wengrenovich et al. Optimization of a TRIP steel for adiabatic fragment protection. Materials Today: Proceedings 2S, 2015, pp. S639-S642. From: International Conference of Mertensitic Transformations, ICOMAT-2014, Jul. 2014.*

* cited by examiner

*Primary Examiner* — Russell S Negin
(74) *Attorney, Agent, or Firm* — Locke Lord LLP; Tim Tingkang Xia, Esq.

(57) ABSTRACT

An optimized Gamma-prime (γ') strengthened austenitic transformation induced plasticity (TRIP) steel comprises a composition designed and processed such that the optimized γ' strengthened austenitic TRIP steel meets property objectives comprising a yield strength of 896 MPa (130 ksi), and an austenite stability designed to have $M_s^o(sh)=-40°$ C., wherein $M_s^o(sh)$ is a temperature for shear, and wherein the property objectives are design specifications of the optimized γ' strengthened austenitic TRIP steel. The optimized γ' strengthened austenitic TRIP steel is Blastalloy TRIP 130.

18 Claims, 70 Drawing Sheets
(68 of 70 Drawing Sheet(s) Filed in Color)

Related U.S. Application Data

(60) Provisional application No. 62/320,036, filed on Apr. 8, 2016.

(51) Int. Cl.
*C22C 38/44* (2006.01)
*C22C 38/46* (2006.01)
*C22C 38/50* (2006.01)
*C22C 38/54* (2006.01)
*G01N 33/50* (2006.01)
*G16C 60/00* (2019.01)
G06F 30/27 (2020.01)
G06F 113/26 (2020.01)

(a) (b)

(c) (d)

OPTIMIZED GAMMA-PRIME STRENGTHENED AUSTENITIC TRIP STEEL AND DESIGNING METHODS OF SAME

CROSS-REFERENCE TO RELATED PATENT APPLICATIONS

This application is a divisional patent application of U.S. patent application Ser. No. 15/483,559, filed Apr. 10, 2017, now allowed, which itself claims priority to and the benefit of, pursuant to 35 U.S.C. § 119(e), of U.S. provisional patent application Ser. No. 62/320,036, filed Apr. 8, 2016, which are incorporated herein by reference in their entireties.

STATEMENT AS TO RIGHTS UNDER FEDERALLY-SPONSORED RESEARCH

This invention was made with government support under N00014-12-1-0455 awarded by the Office of Naval Research. The government has certain rights in the invention.

Some references, which may include patents, patent applications and various publications, are cited in a reference list and discussed in the description of this invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [23] represents the 23th reference cited in the reference list, namely, Nicholas J. Wengrenovich and Gregory B. Olson. Optimization of a TRIP steel for adiabatic fragment protection. Materials Today: Proceedings, S2:S639-S642, 2015.

FIELD OF THE INVENTION

The invention relates generally to materials, and more particularly, to optimized gamma-prime strengthened austenitic transformation induced plasticity (TRIP) steel and designing methods of the same.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Computational materials design has given materials engineers the tools to drastically reduce both the time and the cost of creating and deploying new materials. When focusing on the design of high performance blast and fragment resistant steels, the materials designer must create a material that not only exhibits high uniform ductility but also high shear localization resistance at high strengths. Classically, ductility and strength are inversely related as the microstructural characteristics that promote high strength generally limit ductility and vice-versa. However, high strength and ductility can be achieved in metastable austenitic steels by exploiting the transformation induced plasticity effect. The transformation induced plasticity (TRIP) effect utilizes the diffusionless, distortive, shear dominated martensitic transformation to introduce a strain hardening effect with the application of stress. Through transformation plasticity, a structural change in the material allows for combinations of high strength, ductility, and shear localization resistance.

With an increasing number of terrorist attacks globally and the continued decrease in differentiation between civilians and combatants, the need to protect both military personnel and civilians domestically and abroad is paramount. On Oct. 12, 2000 the USS Cole was attacked by a suicide bomber piloting a small craft filled with explosives. When the explosives detonated, a 40 by 60 foot hole was blown into the side of the ship, leaving 17 American sailors dead and another 39 injured. The following year, the eyes of Americans were opened to the terrorist threat on the home front after the al-Qaeda attacks of Sep. 11, 2001. Three years later, a different terrorist cell bombed commuter trains in Madrid, Spain, resulting in the deaths of 191 civilians and the injury of over 1,800 more. In early 2013, terrorism was brought back to U.S. soil when pressure cooker bombs placed in trash cans exploded near the finish line of the Boston Marathon. Three died and over 250 were injured from the two blasts.

Responding to both the increasing occurrence of terrorist attacks and the vulnerability of the hulls of US Navy ships to these attacks, the Office of Naval Research (ONR) has launched a research initiative to develop and engineer high performance materials able to withstand high-impulse and high-stress conditions that result from explosions. Supported under the "Naval Materials by Design" Grand Challenge and the Materials Genome Initiative, a multi-disciplinary research initiative focuses on developing new steel compositions and structures for integration into the hulls of US Navy ships.

SUMMARY OF THE INVENTION

One of the objectives of this invention is to develop a novel blast resistant steel with superior fragment penetration resistance by using the goal/means engineering approach within the materials design framework. A system of predictive models is further developed and implemented to design a high performance steel that meets the property objectives. In certain aspects, this invention relates to a method to analyze a high-performance, computationally designed, fully austenitic, $\gamma'$ precipitation strengthened steel, TRIP-180, and optimize it for fragment penetration resistance while comparing it to the widely used HSLA-100 steel. Following this analysis, parametric models are improved to allow for the computational design of a new steel, Blastalloy TRIP 130, for optimum performance for blast and fragment protection applications.

In one aspect of the invention, an optimized Gamma-prime ($\gamma'$) strengthened austenitic transformation induced plasticity (TRIP) steel comprises a composition designed and processed such that the optimized $\gamma'$ strengthened austenitic TRIP steel meets property objectives comprising a yield strength of 896 MPa (130 ksi), and an austenite stability designed to have $M_s^o$(sh)=−40° C., wherein $M_s^o$(sh) is a temperature for shear, and wherein the property objectives are design specifications of the optimized γ' strengthened austenitic TRIP steel.

In one embodiment, the property objectives further comprise a fragment simulating projectile (FSP) ballistic limit, $V_{50}$>1.2*$V_{50}^{baseline}$, a shear instability resistance, $\gamma_i^a$>75%, a uniform tensile ductility, $\varepsilon_u$>30%, and a fracture toughness, $K_{IC}$≥90 MPa/m$^{0.5}$.

In one embodiment, the composition comprises nickel (Ni) in a range of about 28.93±0.2 wt. %, chromium (Cr) in a range of about 4.0±0.2 wt. %, titanium (Ti) in a range of about 2.03±0.1 wt. %, aluminum (Al) in a range of about 1.23±0.05 wt. %, molybdenum (Mo) in a range of about 1.2±0.05 wt. %, vanadium (V) in a range of about 0.3±0.05 wt. %, C in a range of about 0.01±0.005 wt. %, boron (B) in a range of about 0.0125±0.005 wt. %, and iron (Fe) in balance.

In one embodiment, the optimized γ' strengthened austenitic TRIP steel is Blastalloy TRIP 130.

In one embodiment, η grain boundary cellular precipitation is thermodynamically eliminated, and a peak strength of 896 MPa is achieved through precipitation of γ', and wherein the austenite stability designed to have $M_s^o$(sh)=−40° C. is achieved given the austenite matrix composition at the peak strength.

In one embodiment, a driving force difference between the γ' and η phases is −285 J/mol.

In one embodiment, a volume fraction and a radius of the γ' precipitates are controlled by tempering times and temperatures while an antiphase boundary energy (APBE) is a function of the composition of the γ' precipitates.

In one embodiment, the radius, the volume fraction, and the APBE of the γ' precipitates at peak strengthening are respectively 13.343 nm, 0.1473, 0.2489 J/mol providing a strength increase of 552 MPa from the γ' precipitates.

In one embodiment, the strength increase is a function of the radius, the volume fraction, and the APBE.

In another aspect of the invention, a method for designing an iron-based alloy comprises defining property objectives of the iron-based alloy, wherein the property objectives are design specifications of the iron-based alloy; designing a composition of the iron-based alloy according to the property objectives; and processing the composition to form the iron-based alloy that meets the property objectives.

In one embodiment, the iron-based alloy is an optimized Gamma-prime (γ') strengthened austenitic transformation induced plasticity (TRIP) steel.

In one embodiment, the property objectives comprise a yield strength of 896 MPa (130 ksi), and a austenite stability designed to have $M_s^o$(sh)=−40° C., $M_s^o$(sh) being a temperature for shear.

In one embodiment, the property objectives further comprise a fragment simulating projectile (FSP) ballistic limit, $V_{50}$>1.2*$V_{50}^{baseline}$, a shear instability resistance, $\gamma_i^a$>75%, a uniform tensile ductility, $\varepsilon_u$>30%, and a fracture toughness, $K_{ID}$≥90 MPa/m$^{0.5}$.

In one embodiment, the composition comprises nickel (Ni) in a range of about 28.93±0.2 wt. %, chromium (Cr) in a range of about 4.0±0.2 wt. %, titanium (Ti) in a range of about 2.03±0.1 wt. %, aluminum (Al) in a range of about 1.23±0.05 wt. %, molybdenum (Mo) in a range of about 1.2±0.05 wt. %, vanadium (V) in a range of about 0.3±0.05 wt. %, C in a range of about 0.01±0.005 wt. %, boron (B) in a range of about 0.0125±0.005 wt. %, and iron (Fe) in balance.

In one embodiment, the optimized γ' strengthened austenitic TRIP steel is Blastalloy TRIP 130.

In one embodiment, η grain boundary cellular precipitation is thermodynamically eliminated, and a peak strength of 896 MPa is achieved through γ' precipitation, and wherein the austenite stability designed to have $M_s^o$(sh)=−40° C. is achieved given the austenite matrix composition at the peak strength.

In one embodiment, a driving force difference between the γ' and η phases is −285 J/mol.

In one embodiment, a volume fraction and a radius of the γ' precipitates are controlled by tempering times and temperatures while an antiphase boundary energy (APBE) is a function of the composition of the γ' precipitates.

In one embodiment, the radius, the volume fraction, and the APBE of the γ' precipitates at peak strengthening are respectively 13.343 nm, 0.1473, 0.2489 J/mol providing a strength increase of 552 MPa from the γ' precipitates.

In one embodiment, the strength increase is a function of the radius, the volume fraction, and the APBE.

In one embodiment, the step of defining the property objectives of the iron-based alloy is implemented based on design specifications of one or more selected alloys, and experimental knowledge, computational predictions and empirical data from the one or more selected alloys.

In one embodiment, the step of designing the composition of the iron-based alloy is implemented based on designed compositions of the one or more selected alloys.

In one embodiment, the step of processing the composition to form the iron-based alloy comprises deoxidizing and melting the composition; solidifying the deoxidized and melted composition to form an ingot; homogenizing the ingot at a homogenization temperature, wherein the homogenization temperature is selected at a high enough temperature to promote fast diffusion, but below a temperature to prevent incipient melting; performing hot working for the ingot at a hot working temperature that is above its recrystallization temperature at which the ingot is plastically deformed; solution treating the ingot at a solution temperature, wherein the solution temperature is selected not only at a temperature above where the γ' phase is in solution, but also where the grain refining titanium carbide phase is present, such that at the solution temperature, the only phases present are the austenite matrix and titanium carbide grain refiners; fast cooling the ingot; and tempering the ingot at a tempering temperature for a tempering time to form the iron-based alloy.

In one embodiment, to effectively model an extreme case of incipient melting during solidification as compared to equilibrium solidification, a Scheil simulation is performed using the Scheil module in Thermo-Calc, wherein the Scheil simulation implements the Scheil-Gulliver equation for solute redistribution during solidification.

In one embodiment, the homogenizing step is performed to ensure that the incipient melting does not occur.

In one embodiment, the titanium carbide phase allows for grain boundary pinning in order to maintain the grain structure achieved by the hot working.

In one embodiment, in order to determine the tempering time at 700° C. for Blastalloy TRIP 130 to reach peak strengthening and optimum austenite stability, the PrecipiCalc models are used to simulate precipitation kinetics of the γ' precipitates, wherein at each timestep of output, the room temperature yield strength and the $M_s^o$ temperatures are calculated.

In one embodiment, to reduce the tempering time being less than about 20 hrs, a number of PrecipiCalc simulations are run at different tempering times to create precipitation predictions aligning time to peak strength to the tempering temperature, wherein the tempering temperature calculated to achieve peak strengthening at about 20 hr is about 738° C.

In one embodiment, to achieve the designed strength and austenite stability, the tempering step is performed at about 740° C. for about 18 hr, followed by a furnace cooling to at 700° C. for about 2 hr, wherein a yield strength of 887.6 MPa and a $M_s^o(sh)$ temperature of −39.5° C. are achieved.

In yet another aspect of the invention, a parametric computational design of an alloy that meets property objectives comprising a strength goal, an austenite stability goal, and a thermodynamic suppression of η grain boundary cellular reactions comprises thermodynamically suppressing an η phase of the alloy to prevent grain boundary cellular precipitation; building γ' precipitation strengthening on output from thermodynamic calculations to provide a range of radii and volume fractions of γ' that satisfy the strength goal; and achieving the austenite stability goal, while maintaining the thermodynamic suppression of the η phase, and the γ' precipitation required to obtain the strength goal, wherein the evolution of the matrix composition with the γ' precipitation is quantified, and constrained equilibrium calculations within Thermo-Calc are made.

In one embodiment, the thermodynamically suppressing step comprises Thermo-Calc calculations of driving forces for the γ' and η phases.

In one embodiment, to ensure the η phase is thermodynamically suppressed, the alloy is designed to have a driving force difference between the γ' phase and the η phase at a tempering temperature at least equal to or greater than −415 J/mol.

In one embodiment, the driving force difference changes by varying a composition of the alloy.

In one embodiment, the volume fraction and radius of the γ' precipitates are controlled by tempering times and temperatures while an antiphase boundary energy (APBE) is a function of the composition of the γ' precipitates.

In one embodiment, a strength increase is a function of the radius, the volume fraction, and the APBE.

In one embodiment, to achieve the strength goal, the γ' precipitation is controlled to obtain the radius at peak strengthening with a large volume fraction if the APBE is decreased from the design of TRIP-180.

In one embodiment, the austenite stability is controlled primarily by nickel and chromium content remaining in the matrix after the precipitation of the γ'.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

The following drawings form part of the present specification and are included to further demonstrate certain aspects of the invention. The invention may be better understood by reference to one or more of these drawings in combination with the detailed description of specific embodiments presented herein. The drawings described below are for illustration purposes only. The drawings are not intended to limit the scope of the present teachings in any way.

DETAILED DESCRIPTION OF THE INVENTION

Figure 1:
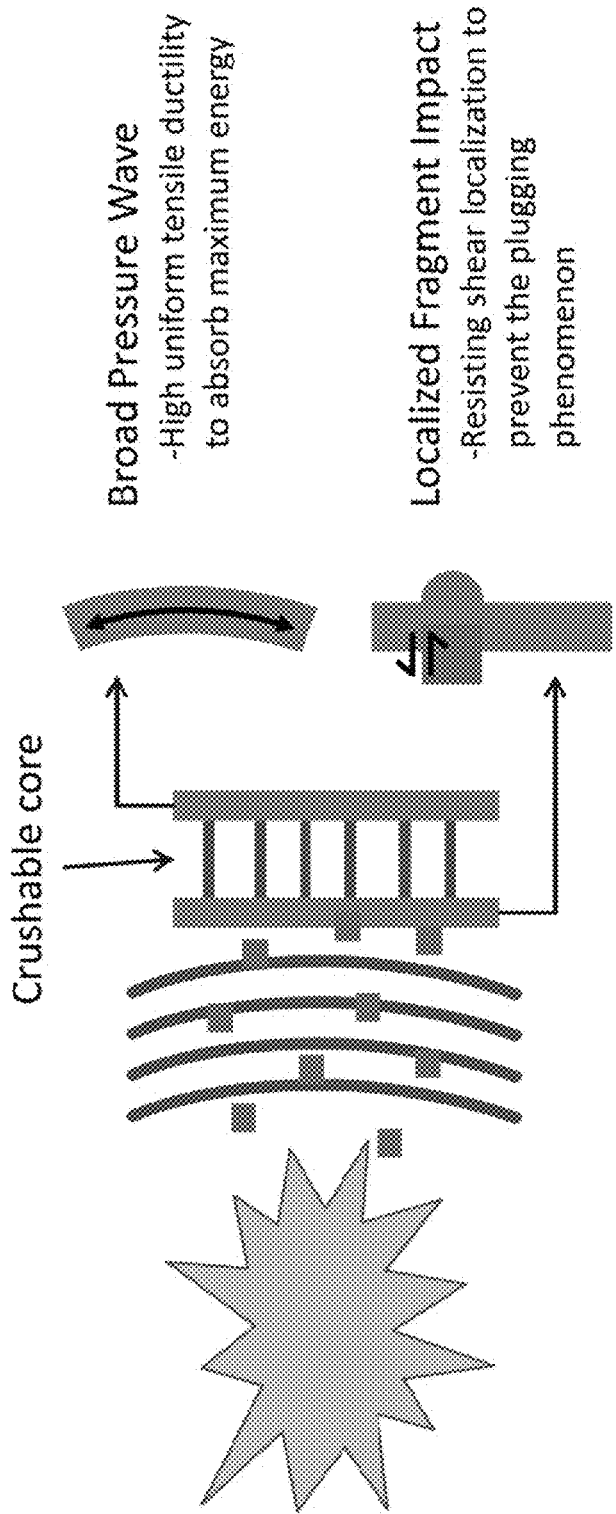
FIG. 1 shows a schematic of the deformation mechanisms a steel would need to withstand to survive an explosion.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the phrase "at least one of A, B, and C" should be construed to mean a logical (A or B or C), using a non-exclusive logical OR. It should be understood that one or more operations within a method is executed in different order (or concurrently) without altering the principles of the invention.

Embodiments of the invention are illustrated in detail hereinafter with reference to accompanying drawings. It should be understood that specific embodiments described herein are merely intended to explain the invention, but not intended to limit the invention. In accordance with the purposes of this invention, as embodied and broadly described herein, this invention, in certain aspects, relates to optimized gamma-prime strengthened austenitic TRIP steel and designing methods of the same.

Blast and Fragment Protection Overview: Before designing a steel that is able to withstand explosions, it is critical to develop an understanding of the deformation mechanisms and stress states that metallic alloys undergo when subjected to an explosion. The schematic in FIG. 1 displays the primary deformation mechanisms present during an explosion: a broad pressure wave and localized fragment penetration. These two mechanisms present two entirely different stress states and thus require two different sets of property objectives to obtain the performance of blast resistance. Therefore, the steel must be able to withstand the pressure wave resulting from the energy release of the explosion as well as the shear localization resulting from the high velocity impact of shrapnel and debris impacting the steel. To withstand the pressure wave, the steel must have high uniform ductility and have the potential to undergo large amounts of deformation to absorb the maximum amount of energy. To resist fragment penetration, the steel must have a high shear localization resistance to avoid the plugging phenomenon that occurs during pure shear conditions. One aspect of this invention focuses on maximizing the shear localization resistance while maintaining a high level of uniform ductility.

Systems Design Approach: Within materials science and engineering, more is known about steel than any other class of materials as it is one of the oldest "engineered" materials. Since the earliest mention of steel making in 1800 B.C., empirical processes have been employed to develop new alloys. With the expansion of computational power, empirical material development processes become more difficult and expensive to keep pace with the advancement of other scientific and engineering disciplines. Given these limitations, a systems based approach to materials design has been employed. This framework, where materials are viewed as a system of hierarchical structures, was first proposed by Smith [21]. Although this framework of relating internal structures to external properties can be applied to all classes of materials, the vast body of knowledge surrounding steel alloys allows for the most directed application of the framework. This systems design approach requires an understanding of the complex interactions of all the sub-systems within materials and how they can be developed to achieve the design objective with high levels of efficiency.

Figure 2:
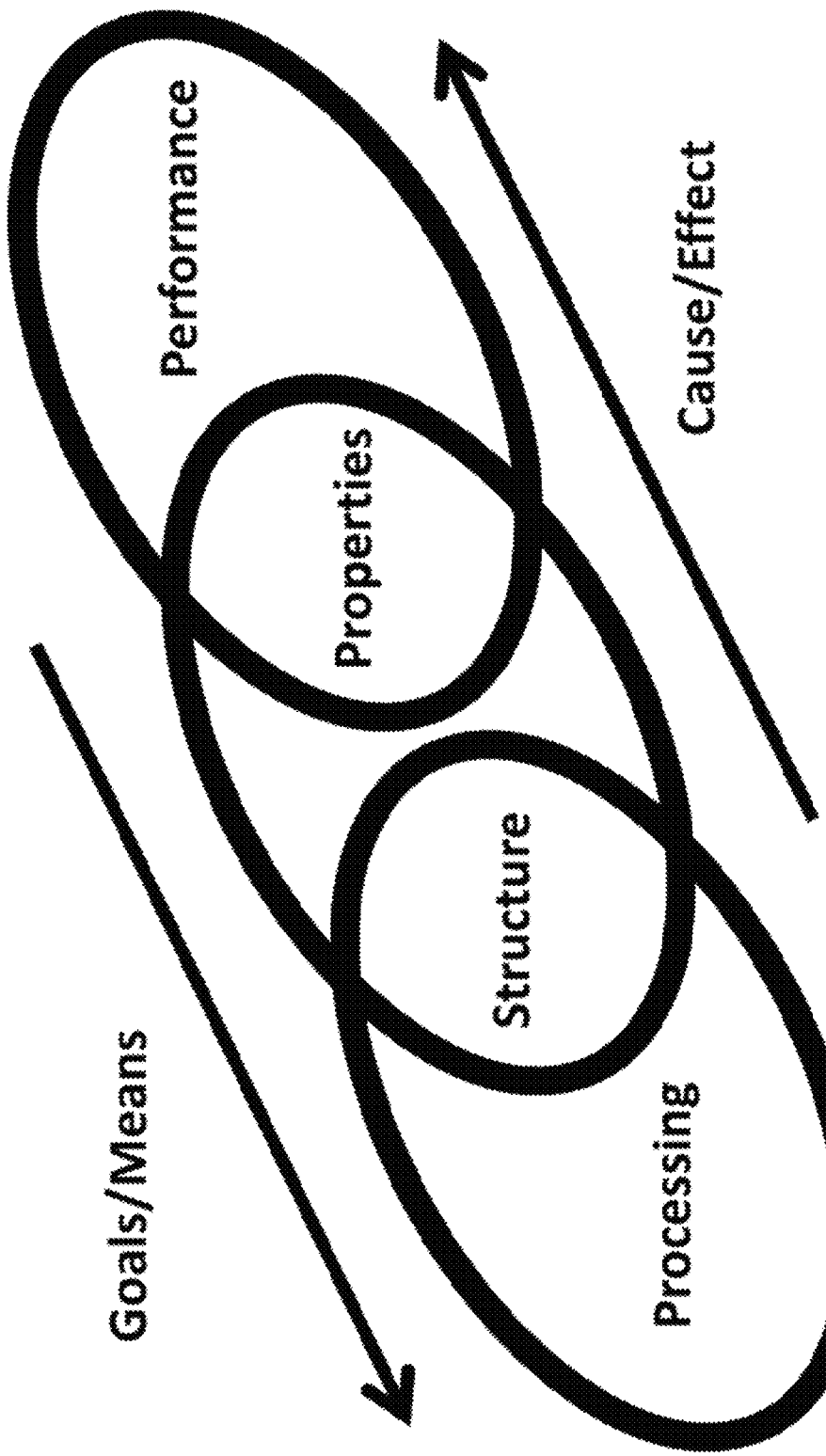
FIG. 2 shows a three link chain model describing the interrelation between processing, structure, properties, and performance [16].
Figure 3:
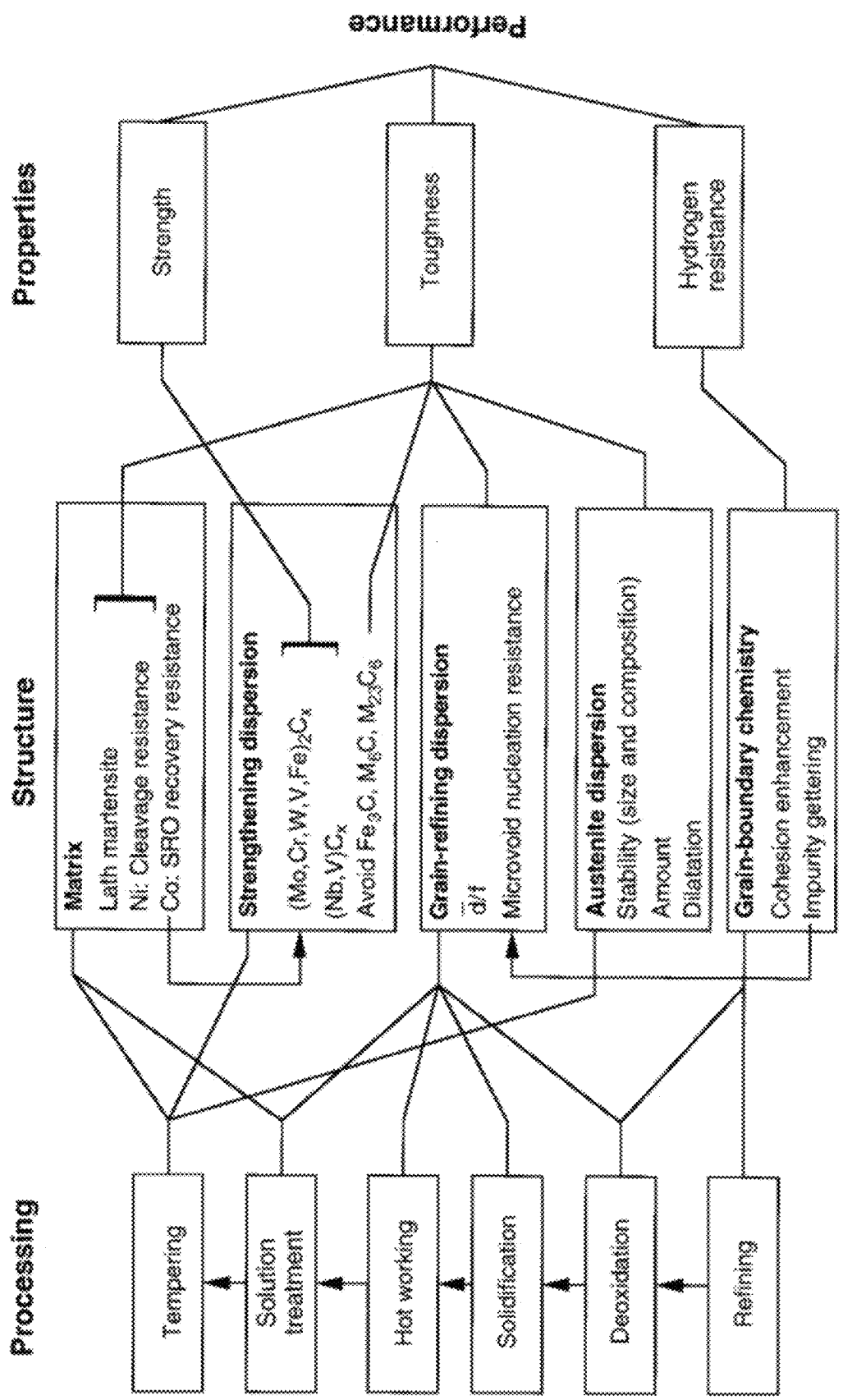
FIG. 3 shows systems design chart for a high-performance secondary-hardening martensitic steel [16].

In the 1970s, Cohen introduced the concept of reciprocity between the processing, structure, properties, and performance of materials [6]. This identified the relationships between the first order of sub-systems as shown in the three link chain in FIG. 2. The reciprocity not only confirms the traditional understanding of materials science in the cause/effect framework where processing affects structure, which affects properties, which gives a level of performance but also asserts that the performance dictates the required properties, these properties dictate the structure, and the structure requires a certain processing path. Working down the three link chain gives a goals/means framework and provides the basis for materials design. Materials design begins with defining the desired performance. Once the performance is stated, the specific properties that produce the performance are quantified and then the selection of structures that yield these properties are chosen. Finally, the processing pathways are selected which deliver the required structure. This is exemplified in FIG. 3 for the case of a high-performance secondary-hardening martensitic steel [16]. The links between the processing, structure, properties, and performance are clearly identified by sets of connecting lines, each of these requires a set of models developed from advanced characterization techniques. This systems based approach drives the design work discussed in the disclosure.

In one aspect of the invention, an optimized Gamma-prime (γ') strengthened austenitic transformation induced plasticity (TRIP) steel comprises a composition designed and processed such that the optimized γ' strengthened austenitic TRIP steel meets property objectives comprising a yield strength of 896 MPa (130 ksi), and an austenite stability designed to have $M_s^o(sh)=-40°$ C., wherein $M_s^o(sh)$ is a temperature for shear, and wherein the property objectives are design specifications of the optimized γ' strengthened austenitic TRIP steel.

In one embodiment, the property objectives further comprise a fragment simulating projectile (FSP) ballistic limit, $V_{50}>1.2*V_{50}^{baseline}$, a shear instability resistance, $\gamma_i^a>75\%$, a uniform tensile ductility, $\varepsilon_u>30\%$, and a fracture toughness, $K_{IC} \geq 90$ MPa/m$^{0.5}$. In one embodiment, the composition comprises nickel (Ni) in a range of about 28.93±0.2 wt. %, chromium (Cr) in a range of about 4.0±0.2 wt. %, titanium (Ti) in a range of about 2.03±0.1 wt. %, aluminum (Al) in a range of about 1.23±0.05 wt. %, molybdenum (Mo) in a range of about 1.2±0.05 wt. %, vanadium (V) in a range of about 0.3±0.05 wt. %, C in a range of about 0.01±0.005 wt. %, boron (B) in a range of about 0.0125±0.005 wt. %, and iron (Fe) in balance.

In one embodiment, the optimized γ' strengthened austenitic TRIP steel is Blastalloy TRIP 130.

In one embodiment, η grain boundary cellular precipitation is thermodynamically eliminated, and a peak strength of 896 MPa is achieved through precipitation of γ', and wherein the austenite stability designed to have $M_s^o(sh)=-40°$ C. is achieved given the austenite matrix composition at the peak strength.

In one embodiment, a driving force difference between the γ' and η phases is −285 J/mol.

In one embodiment, a volume fraction and a radius of the γ' precipitates are controlled by tempering times and temperatures while an antiphase boundary energy (APBE) is a function of the composition of the γ' precipitates.

In one embodiment, the radius, the volume fraction, and the APBE of the γ' precipitates at peak strengthening are respectively 13.343 nm, 0.1473, 0.2489 J/mol providing a strength increase of 552 MPa from the γ' precipitates.

In one embodiment, the strength increase is a function of the radius, the volume fraction, and the APBE.

In another aspect of the invention, a method for designing an iron-based alloy comprises defining property objectives of the iron-based alloy, wherein the property objectives are design specifications of the iron-based alloy; designing a composition of the iron-based alloy according to the property objectives; and processing the composition to form the the iron-based alloy that meets the property objectives.

In one embodiment, the iron-based alloy is an optimized Gamma-prime (γ') strengthened austenitic transformation induced plasticity (TRIP) steel.

In one embodiment, the property objectives comprise a yield strength of 896 MPa (130 ksi), and a austenite stability designed to have $M_s^o(sh)=-40°$ C., $M_s^o(sh)$ being a temperature for shear.

In one embodiment, the property objectives further comprise a fragment simulating projectile (FSP) ballistic limit, $V_{50}>1.2*V_{50}^{baseline}$, a shear instability resistance, $\gamma_i^a>75\%$, a uniform tensile ductility, $\varepsilon_u>30\%$, and a fracture toughness, $K_{IC} \geq 90$ MPa/m$^{0.5}$.

In one embodiment, the composition comprises nickel (Ni) in a range of about 28.93±0.2 wt. %, chromium (Cr) in a range of about 4.0±0.2 wt. %, titanium (Ti) in a range of about 2.03±0.1 wt. %, aluminum (Al) in a range of about 1.23±0.05 wt. %, molybdenum (Mo) in a range of about 1.2±0.05 wt. %, vanadium (V) in a range of about 0.3±0.05 wt. %, C in a range of about 0.01±0.005 wt. %, boron (B) in a range of about 0.0125±0.005 wt. %, and iron (Fe) in balance.

In one embodiment, the optimized γ' strengthened austenitic TRIP steel is Blastalloy TRIP 130.

In one embodiment, η grain boundary cellular precipitation is thermodynamically eliminated, and a peak strength of 896 MPa is achieved through γ' precipitation, and wherein the austenite stability designed to have $M_s^o(sh)=-40°$ C. is achieved given the austenite matrix composition at the peak strength.

In one embodiment, a driving force difference between the γ' and η phases is −285 J/mol.

In one embodiment, a volume fraction and a radius of the γ' precipitates are controlled by tempering times and temperatures while an antiphase boundary energy (APBE) is a function of the composition of the γ' precipitates.

In one embodiment, the radius, the volume fraction, and the APBE of the γ' precipitates at peak strengthening are respectively 13.343 nm, 0.1473, 0.2489 J/mol providing a strength increase of 552 MPa from the γ' precipitates.

In one embodiment, the strength increase is a function of the radius, the volume fraction, and the APBE.

In one embodiment, the step of defining the property objectives of the iron-based alloy is implemented based on design specifications of one or more selected alloys, and experimental knowledge, computational predictions and empirical data from the one or more selected alloys.

In one embodiment, the step of designing the composition of the iron-based alloy is implemented based on designed compositions of the one or more selected alloys.

Figure 40:
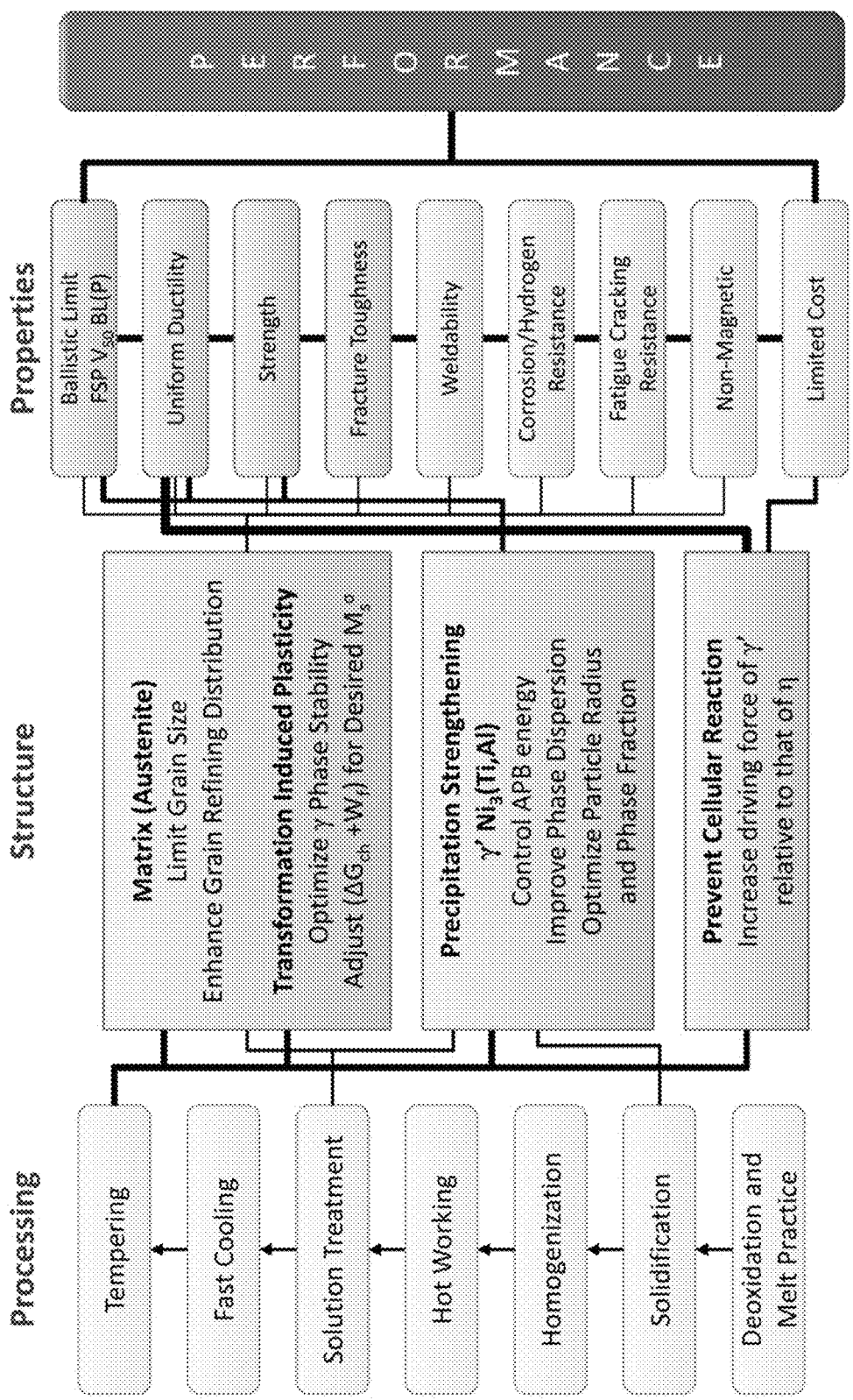
FIG. 40 shows systems design chart for Blastalloy TRIP 130, according to one embodiment of the invention.

In one embodiment, as shown in FIG. 40, the step of processing the composition to form the iron-based alloy comprises deoxidizing and melting the composition; solidifying the deoxidized and melted composition to form an ingot; homogenizing the ingot at a homogenization temperature, wherein the homogenization temperature is selected at a high enough temperature to promote fast diffusion, but below a temperature to prevent incipient melting; performing hot working for the ingot at a hot working temperature that is above its recrystallization temperature at which the ingot is plastically deformed; solution treating the ingot at a solution temperature, wherein the solution temperature is selected not only at a temperature above where the γ' phase is in solution, but also where the grain refining titanium carbide phase is present, such that at the solution temperature, the only phases present are the austenite matrix and titanium carbide grain refiners; fast cooling the ingot; and tempering the ingot at a tempering temperature for a tempering time to form the iron-based alloy.

In one embodiment, to effectively model an extreme case of incipient melting during solidification as compared to equilibrium solidification, a Scheil simulation is performed using the Scheil module in Thermo-Calc, wherein the Scheil simulation implements the Scheil-Gulliver equation for solute redistribution during solidification.

In one embodiment, the homogenizing step is performed to ensure that the incipient melting does not occur.

In one embodiment, the titanium carbide phase allows for grain boundary pinning in order to maintain the grain structure achieved by the hot working.

In one embodiment, in order to determine the tempering time at 700° C. for Blastalloy TRIP 130 to reach peak strengthening and optimum austenite stability, the Precipi-Calc models are used to simulate precipitation kinetics of the γ' precipitates, wherein at each timestep of output, the room temperature yield strength and the $M_s^\sigma$ temperatures are calculated.

In one embodiment, to reduce the tempering time being less than about 20 hrs, a number of PrecipiCalc simulations are run at different tempering times to create precipitation predictions aligning time to peak strength to the tempering temperature, wherein the tempering temperature calculated to achieve peak strengthening at about 20 hr is about 738° C.

In one embodiment, to achieve the designed strength and austenite stability, the tempering step is performed at about 740° C. for about 18 hr, followed by a furnace cooling to at 700° C. for about 2 hr, wherein a yield strength of 887.6 MPa and a $M_s^\sigma$(sh) temperature of −39.5° C. are achieved.

Figure 41:
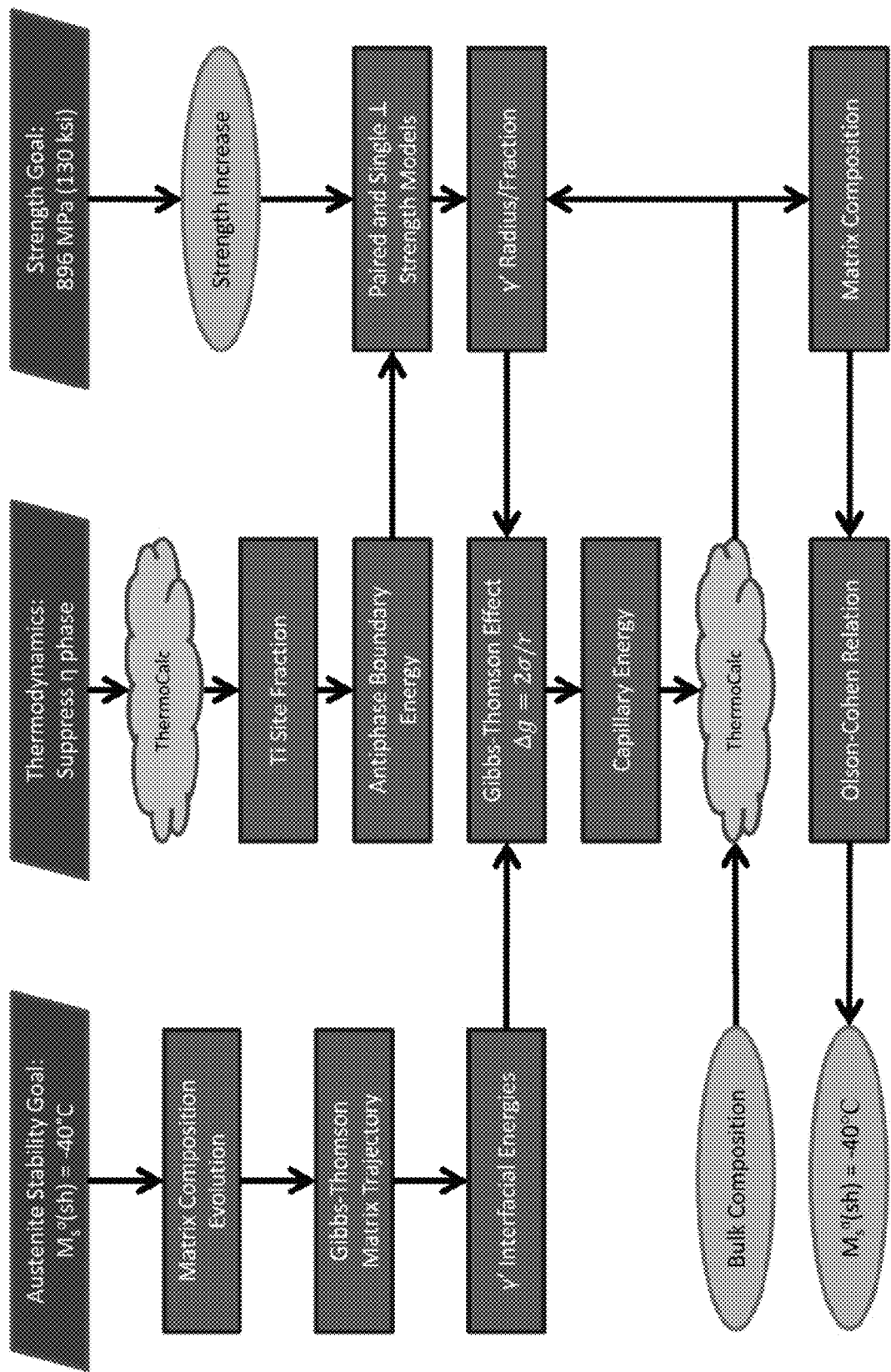
FIG. 41 shows an overview of the approach for the parametric design of Blastalloy TRIP 130, according to one embodiment of the invention.

In yet another aspect of the invention, as shown in FIGS. 40 and 41, a parametric computational design of an alloy that meets property objectives comprising a strength goal, an austenite stability goal, and a thermodynamic suppression of η grain boundary cellular reactions comprises thermodynamically suppressing an η phase of the alloy to prevent grain boundary cellular precipitation; building γ' precipitation strengthening on output from thermodynamic calculations to provide a range of radii and volume fractions of γ' that satisfy the strength goal; and achieving the austenite stability goal, while maintaining the thermodynamic suppression of the η phase, and the γ' precipitation required to obtain the strength goal, wherein the evolution of the matrix composition with the γ' precipitation is quantified, and constrained equilibrium calculations within Thermo-Calc are made.

In one embodiment, the thermodynamically suppressing step comprises Thermo-Calc calculations of driving forces for the γ' and η phases.

In one embodiment, to ensure the η phase is thermodynamically suppressed, the alloy is designed to have a driving force difference between the γ' phase and the η phase at a tempering temperature at least equal to or greater than −415 J/mol.

In one embodiment, the driving force difference changes by varying a composition of the alloy.

In one embodiment, the volume fraction and radius of the γ' precipitates are controlled by tempering times and temperatures while an antiphase boundary energy (APBE) is a function of the composition of the γ' precipitates.

In one embodiment, a strength increase is a function of the radius, the volume fraction, and the APBE.

In one embodiment, to achieve the strength goal, the γ' precipitation is controlled to obtain the radius at peak strengthening with a large volume fraction if the APBE is decreased from the design of TRIP-180.

In one embodiment, the austenite stability is controlled primarily by nickel and chromium content remaining in the matrix after the precipitation of the γ'.

Without intent to limit the scope of the invention, examples according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

1 TRIP-180 Mechanical and Predictive Model Optimization

In certain embodiments of the invention, the mechanical properties of TRIP-180 are optimized for maximum fragment penetration resistance, and the predictive models used for designing Blastalloy TRIP 130 are optimized in the high nickel steel composition space. The experiments performed start under quasi-static conditions in Section 1.1 and progress through ballistic conditions in Section 1.3 to find the optimum $M_s^\sigma$(sh) temperature. Sections 1.4, 1.5, and 1.6 detail the experiments gathering data about the γ' precipitation, austenite stability, and how that data is used to calibrate a precipitation model showing the temporal evolution of the γ' precipitates and matrix composition. For clarity, color schemes throughout this disclosure are kept similar between mechanical tests for identical heat treatment times. For reference, they are listed below for TRIP-180 in hours tempered at 700° C., with the data for HSLA-100 shown in gray:

| Tempering Time (hr): | Color: |
| --- | --- |
| 0.25 | bright blue |
| 0.83 | red |
| 1.0 | forest green |
| 2.5 | green |
| 4.67 | black |
| 5.0 | dark orange |
| 5.25 | purple |
| 6.25 | blue |
| 16.5 | bright purple |

1.1 Quasi-Static Torsion Testing

Figure 4:
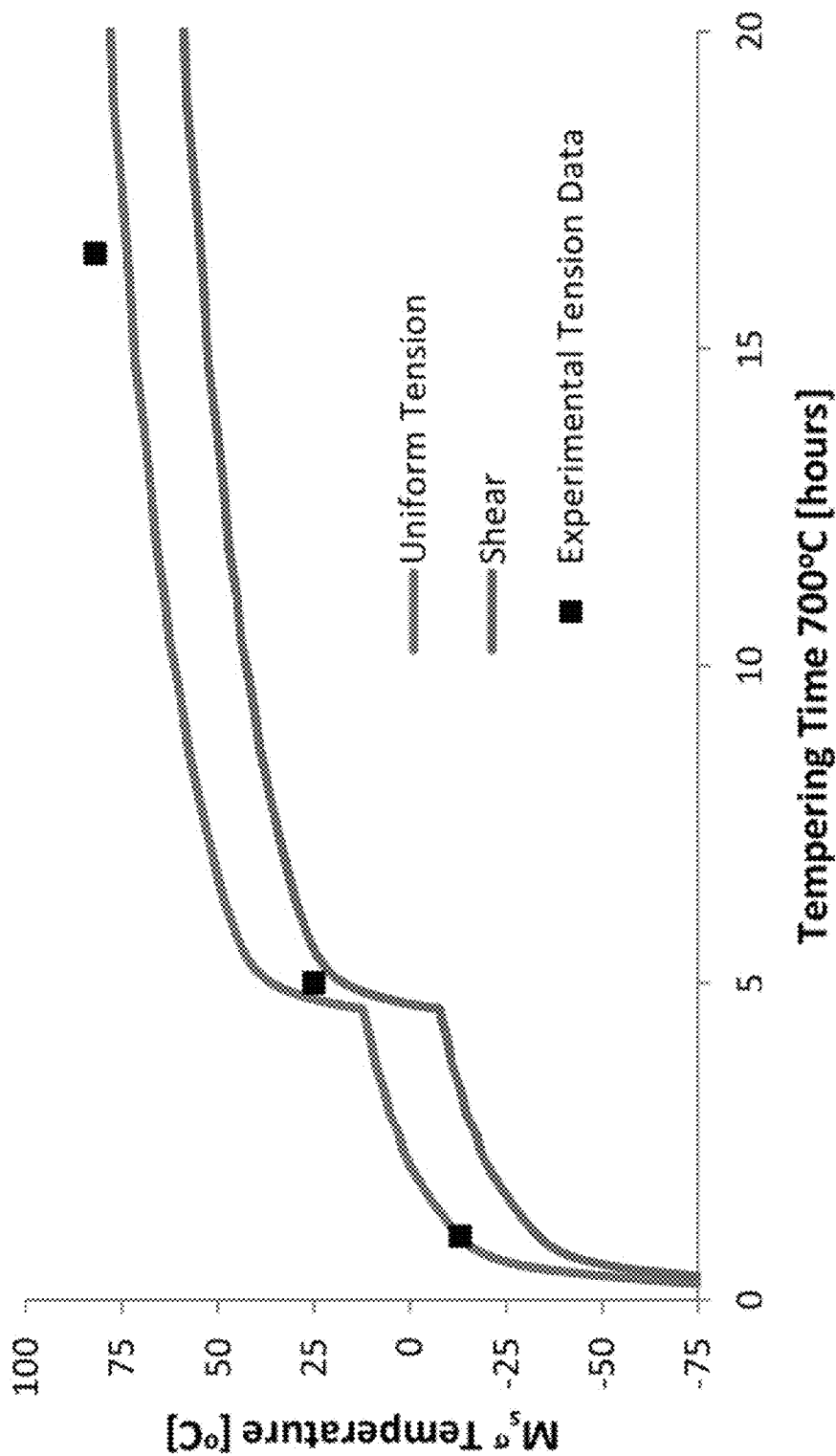
FIG. 4 shows a $M_s^o$ temperature model showing predictions for $M_s^o(u.t.)$ and $M_s^o(sh)$ with comparisons to experimental measurements, according to one embodiment of the invention.

The first step towards understanding the properties that are required to obtain superior fragment protection is to assess TRIP-180's performance under quasi-static torsion. This provides information for which heat treatment allows for the most uniform shear deformation prior to reaching the shear instability strain relative to the $M_s^\sigma$(sh) temperature. In order to calibrate performance to the $M_s^\sigma$(sh) temperature, a $M_s^\sigma$ temperature model, modified from the work of Feinberg, was used by calibrating the $M_s^\sigma$(u.t.) temperature to experimental data, which is shown in FIG. 4.

Figure 5:
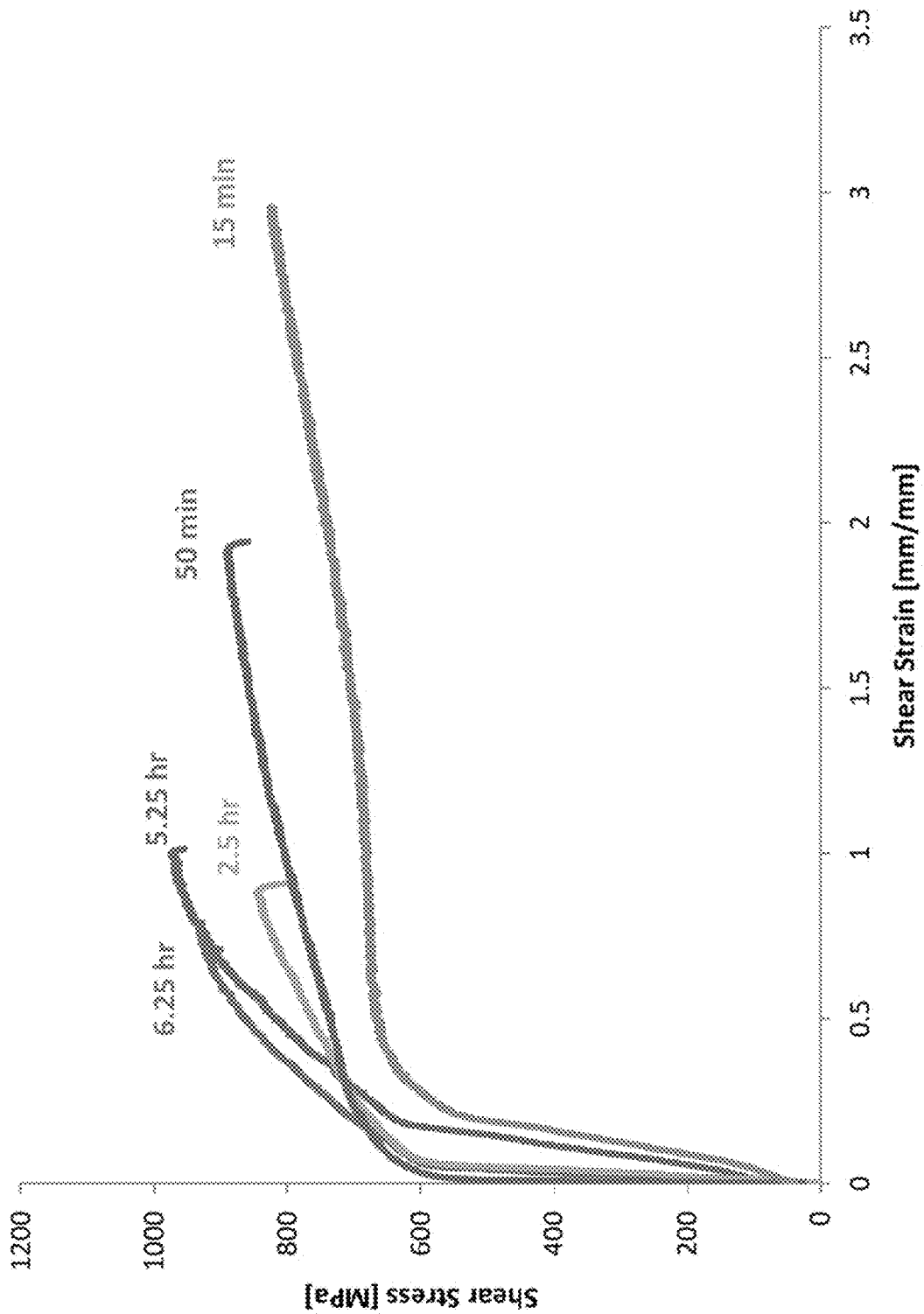
FIG. 5 shows stress-strain curves for TRIP-180 testing in quasi-static torsion as a function of tempering time at 700° C., according to one embodiment of the invention.

A first series of tests was performed where all samples failed in buckling, rather than shear. This resulted in skewed stress/strain measurements as well as martensite fraction calculations. This required the use of the age hardened 1566 steel mandrel inside the specimen to ensure failure occurs in pure shear rather than buckling. The results of this second series of tests are shown in FIG. 5 and the quantitative results of shear failure strain, $\gamma_f$, instability strain, $\gamma_{in}$, ultimate stress, $\tau_{max}$, yield stress, $\tau_y$, plastic strain, $\gamma_p$, martensite fraction, f, rate parameter, f/$\gamma_p$, and performance product, $\tau_f^* \gamma_p$, are tabulated in Table 1.

TABLE 1

Results from quasi-static torsion tests for TRIP-180.

| | TRIP-180 | | | | | |
|---|---|---|---|---|---|---|
| Tempering Time at 700° C. | 6.25 | 5.25 | 2.5 | 0.83 | 0.25 | hr |
| $M_s^\sigma$ (sh) | 29 | 22 | −18 | −37 | −107 | ° C. |
| $T - M_s^\sigma$ (sh) | −8 | −1 | 39 | 58 | 128 | ° C. |
| Shear Failure Strain | 0.789 | 1.01 | 0.909 | 1.94 | 2.96 | mm/mm |
| Shear Instability Strain | 0.789 | 1.01 | 0.909 | 1.94 | 2.96 | mm/mm |
| Shear Ultimate Stress | 934 | 974 | 846 | 891 | 827 | MPa |
| Shear Yield Stress | 581 | 637 | 578 | 542 | 547 | MPa |
| Plastic Strain | 0.737 | 0.822 | 0.848 | 1.93 | 2.75 | mm/mm |
| Martensite Fraction | 0.655 | 0.639 | 0.487 | 0.637 | 0.528 | |
| Rate Parameter | 0.889 | 0.778 | 0.575 | 0.330 | 0.192 | |
| Performance Product | 688 | 801 | 717 | 1720 | 2270 | MPa |

Figure 6:
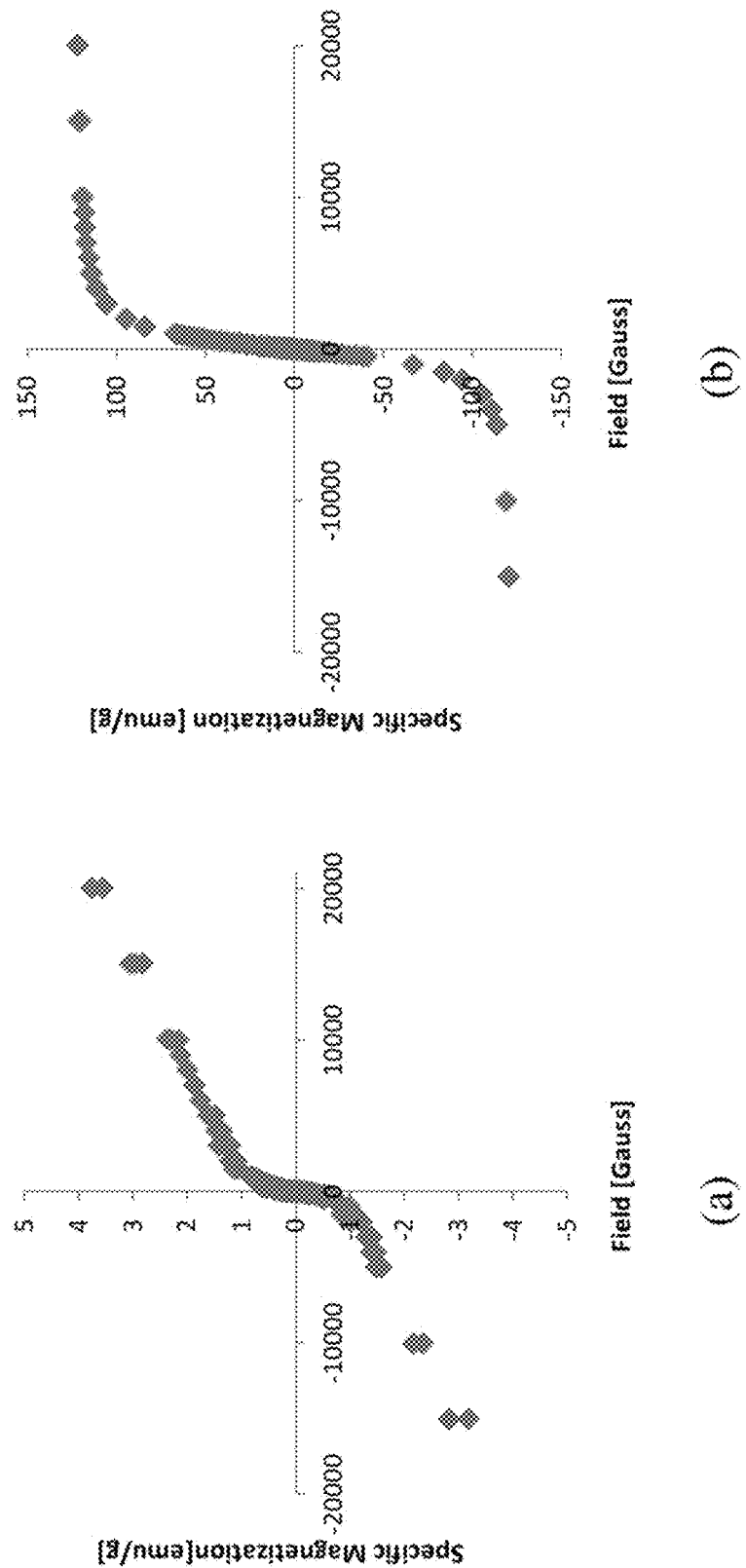
FIG. 6 shows specific magnetization showing the (a) linear dependence of the austenite based on $\chi_M$, and (b) change in behavior after the introduction of transformed martensite, according to one embodiment of the invention.

Shear yield stress was calculated by a 0.2% offset. Plastic strain was calculated both as a function of failure strain minus yield strain and by measurement of the grain shearing and distortion of the microstructure where the angle is directly related to the plastic strain. Good agreement was seen between these as differences were less than 0.1. The transformed martensite fraction was calculated via magnetometry. A parametric correction was made to the measurements to correct for the magnetic susceptibility, $\chi_M$, a dimensionless constant relating induced magnetization to an applied field. The magnetic susceptibility is measured as the slope of the linear dependence of a paramagnetic material [19]. FIG. 6(a) shows the linear dependence for a fully austenitic sample of TRIP-180 without tempering and FIG. 6(b) shows the resulting specific magnetization of the 0.83 hr tempered sample after quasi-static torsion deformation which has increased significantly with the presence of ferromagnetic martensite. The slope, and magnetic susceptibility, in FIG. 6(a) is measured to be $$1.39 * 10^{-4} \frac{emu}{gGauss}.$$

This correction allows for the saturation magnetization of a fully austenitic specimen to equal zero. The rate parameter is taken as the quotient of the fraction of transformed martensite and the plastic strain. It is a measure of the stability of austenite where higher values correspond to higher $M_s^\sigma$ temperatures and lower stability. Finally, the performance product, a product of the stress at failure and plastic strain, is reported as it is a first order approximation of fragment penetration resistance.

From Table 1 it is generally seen that with increasing austenite stability (i.e., lower $M_s^\sigma$ temperatures), the plastic strain and failure strain increase except for the 2.5 hr tempered sample. The strain levels increase from 0.789 to 2.96 and from 0.737 to 2.75 for failure strain and plastic strain, respectively. The 2.5 hour tempered sample exhibits lower shear stress and strain at failure than fit into the observed trends, as well as significantly less transformed martensite than the other samples. This leads to the belief that the wall thickness may be non-uniform throughout the specimen resulting in a decrease of mechanical properties and a non-uniform application of stress resulting in less transformed martensite. A peak in the shear yield stress occurs at the 5.25 hr tempered sample with a value of 637 MPa, although it could be closer to the 2.5 hr tempered sample due to the reasons just discussed. As the plastic strain weighs heavily in the performance product relationship, that quantity increases as well with austenite stability irrespective of the influence of shear yield stress.

Figure 7:
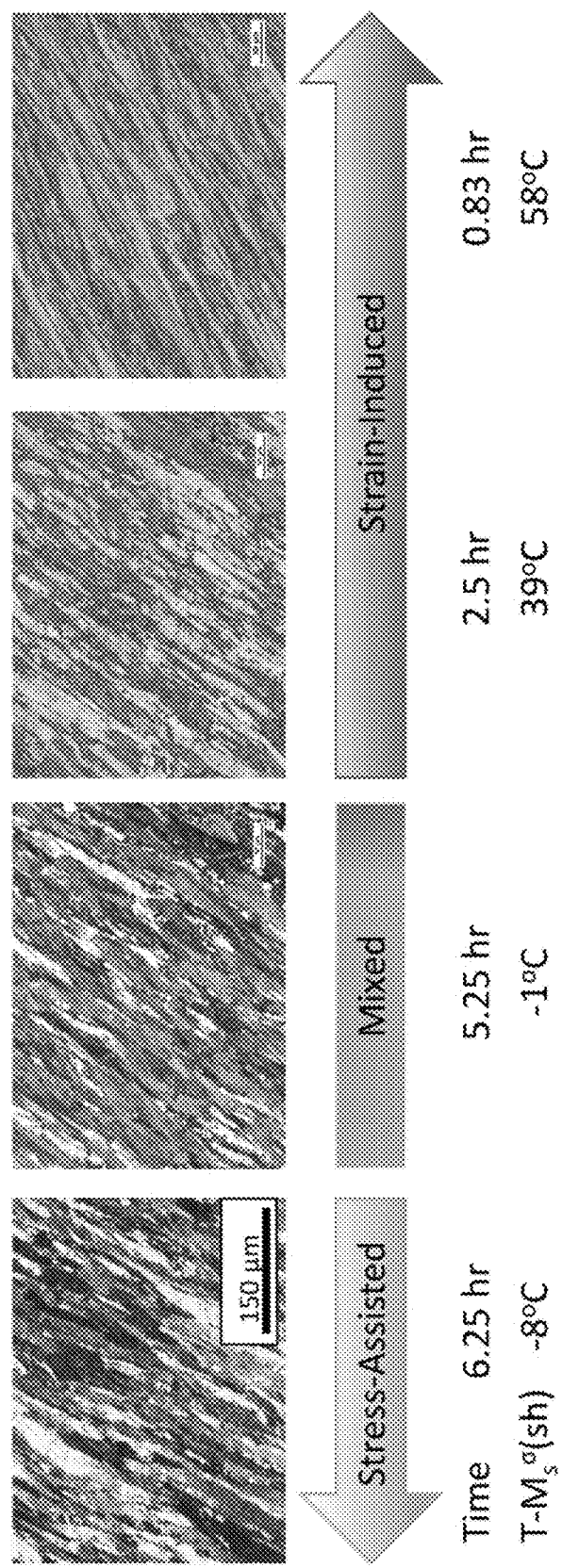
FIG. 7 shows microstructures of failed quasi-static torsion samples as a function of austenite stability. Tempering time at 700° C. and T−$M_s^o(sh)$ values are given to illustrate the transition of martensite from a stress-assisted, lenticular plate morphology, to a finely dispersed, strain-induced, product morphology, when T−$M_s^o(sh)$ passes through zero, according to one embodiment of the invention. Samples are etched with sodium metabisulfite.

With the exception of the 2.5 hr tempered sample, the quantity of martensite generally remains constant with a slight decrease from 0.655 to 0.528 with increased stability even as the amount of plastic strain greatly increases. This behavior is captured in the rate parameter which shows that with less stability, more martensite is transformed per unit strain. When the microstructure of the failed samples, perpendicular to the gauge section, is observed, the type of martensite seen corresponds to the stability as shown in FIG. 7. The martensite transitions from plate morphology in the stress-assisted regime to a finer, plastically deformed morphology where the boundaries are less defined in the strain-induced regime when the $M_s^\sigma$(sh) temperature passes through room temperature (i.e., $T-M_s^\sigma$(sh)=0 as the tests were performed at room temperature). To further investigate the effect of the martensite, it is shown in the stress-strain curves in FIG. 5 that transformation plasticity from the transforming martensite is delaying the onset of shear instability and producing upward curvature behavior of exponential strain hardening. This is echoed in Table 1 where the shear failure and instability strain are identical and with the lack of localized shear bands within the microstructures in FIG. 7. The criterion for necking instability given by Backofen [2] indicates that exponential strain hardening is optimal for extending uniform ductility, this is for uniaxial tension. Work by Staker, using a similar approach as Backofen has determined a criterion for imminent catastrophic shear [2]. Shown in Equation (1), this critical shear instability condition is met when the slope of the true stress-strain curve turns negative. Therefore the extension of uniform shear from strain hardening as seen in FIG. 5 indicates the presence of transformation plasticity.

$$\frac{d\tau}{d\gamma} = 0 \tag{1}$$

1.2 Dynamic HAT-Type Shear Testing

To build upon the results from the quasi-static tests where the loading conditions are isothermal, a dynamic test series was performed where the loading conditions are adiabatic. Dynamic shear tests provide quantitative information about adiabatic shear bands which form after the shear localization strain is surpassed. This information correlates more strongly to ballistic penetration resistance than quasi-static tests as the ballistic and dynamic tests both fall into the adiabatic regime. As with the quasi-static tests, the dynamic tests are performed at room temperature and therefore the stability of the austenite is varied by controlling tempering and not changing experimental conditions. For a separate analysis into these tests, see Wengrenovich and Olson [23].

The results of dynamic HAT testing are shown in Table 2 and follow the data that was presented for the quasi-static tests in Table 1.

the testing of the 6.25 hr tempered sample, the strain gauge on the input bar, which is set to trigger the data capture, delaminated upon impact from the striker bar and no data was captured. Postmortem analysis was performed to determine the shear instability strain and transformed martensite.

As in the case with the quasi-static tests, most of the quantities in Table 2 correlate with the austenite stability. The austenite stability is controlled by precipitation of the γ' strengthening phase. In TRIP-180 and other super-saturated nickel steels, tempering leads to rapid growth and coarsening of γ' precipitates which have the composition $Ni_3(Ti,Al)$. Their growth and coarsening depletes nickel from the aus-

TABLE 2

Results from dynamic HAT-type tests for TRIP-180 and HSLA-100.

|  | TRIP-180 | | | | | | HSLA-100 | |
| --- | --- | --- | --- | --- | --- | --- | --- | --- |
| Tempering Time at 700° C. | 6.25 | 5.25 | 4.67 | 2.5 | 0.83 | 0.25 | N/A | hr |
| $M_s^\sigma$ (sh) | 29 | 22 | 0 | −18 | −37 | −107 | N/A | ° C. |
| $T - M_s^\sigma$ (sh) | −8 | −1 | 21 | 39 | 58 | 128 | N/A | ° C. |
| Shear Failure Strain | — | 0.104 | 0.269 | 0.301 | 0.304 | 0.356 | 0.313 | mm/mm |
| Instability Strain | 0.205 | 0.0881 | 0.208 | 0.118 | 0.115 | 0.141 | 0.358 | mm/mm |
| Shear Ultimate Strength | — | 1080 | 1150 | 1290 | 1420 | 1080 | 970 | MPa |
| Shear Flow Strength | — | 1020 | 1140 | 1250 | 1390 | 1060 | 848 | MPa |
| Plastic Shear Strain | — | 0.0308 | 0.0698 | 0.101 | 0.103 | 0.156 | 0.0903 | mm/mm |
| Transformed Martensite | 0.060 | 0.041 | 0.054 | 0.036 | 0.025 | 0.016 | N/A | |
| Rate Parameter | — | 1.33 | 0.774 | 0.354 | 0.240 | 0.104 | N/A | |
| Performance Product | — | 33.2 | 77.2 | 138 | 205 | 173 | 87.7 | MPa |

Shear instability strain is calculated by measuring the angle of macroscopic deformation on micrograph of the cross section of gauge section. Under dynamic conditions, this is different from the shear failure strain as adiabatic shear bands developed during testing. Instead of shear yield strength, $\tau_y$, shear flow stress, $\tau_f$, is reported and is taken to be the strength at 0.2% strain except for the 5.25 hr tempered sample as the specimen failed before reaching this strain level. After reviewing the stress-strain plot, a 0.1% flow stress was reported. To accurately calculate the stresses and strains at each timestep and produce a stress-strain curve, the incident, transmitted, and reflected waves are aligned. This is done by implementing an underlying assumption in one-dimensional elastic-wave propagation theory that the generated waves must be equal [12] as given in Equation (2) and reproduced below for clarity.

$$\varepsilon_T = \varepsilon_I + \varepsilon_R \quad (2)$$

Figure 8:
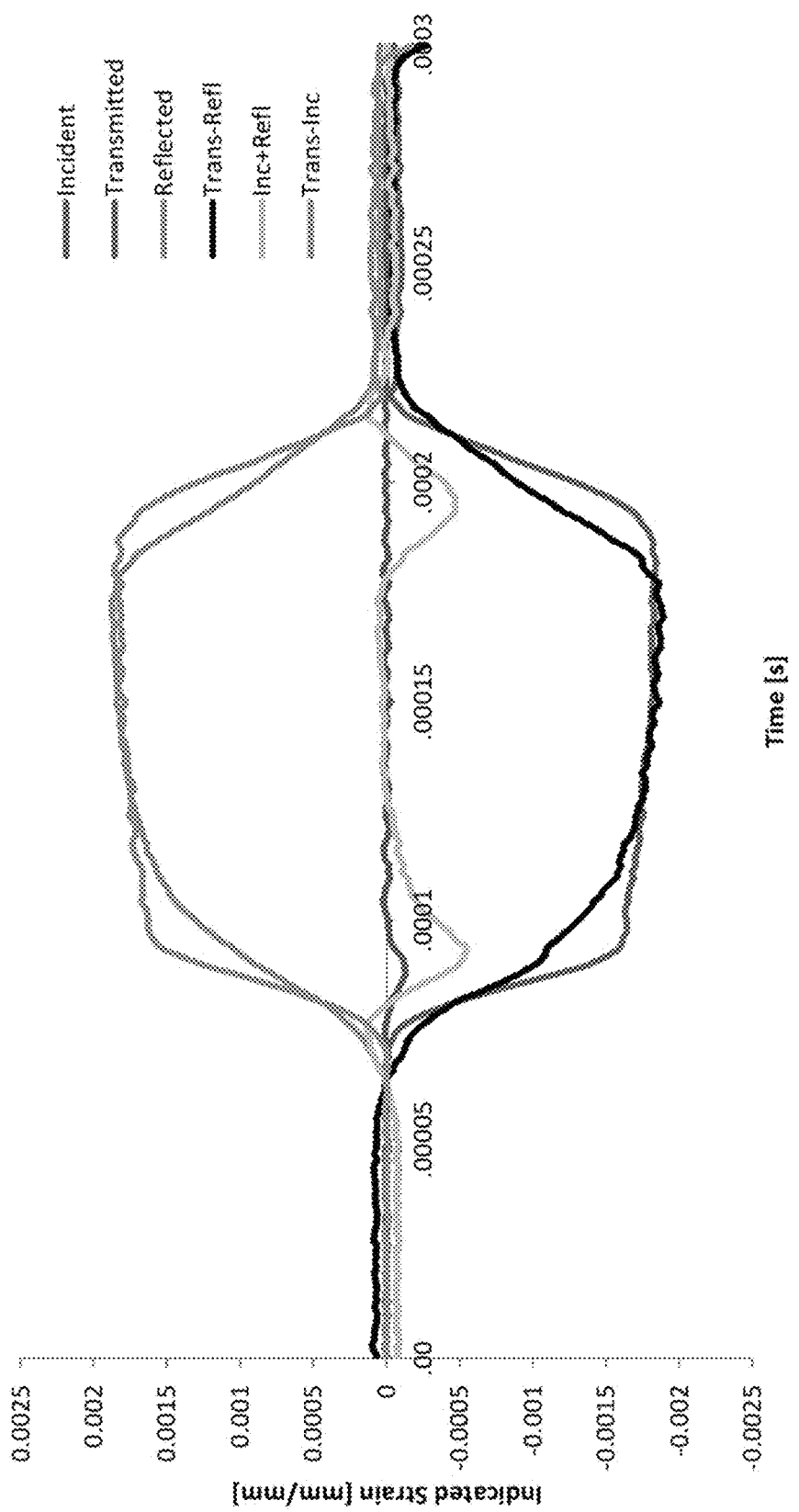
FIG. 8 shows indicated strains for the incident, transmitted, reflected waves and their equal counterparts for the 0.25 hr tempered sample, according to one embodiment of the invention.
Figure 9:
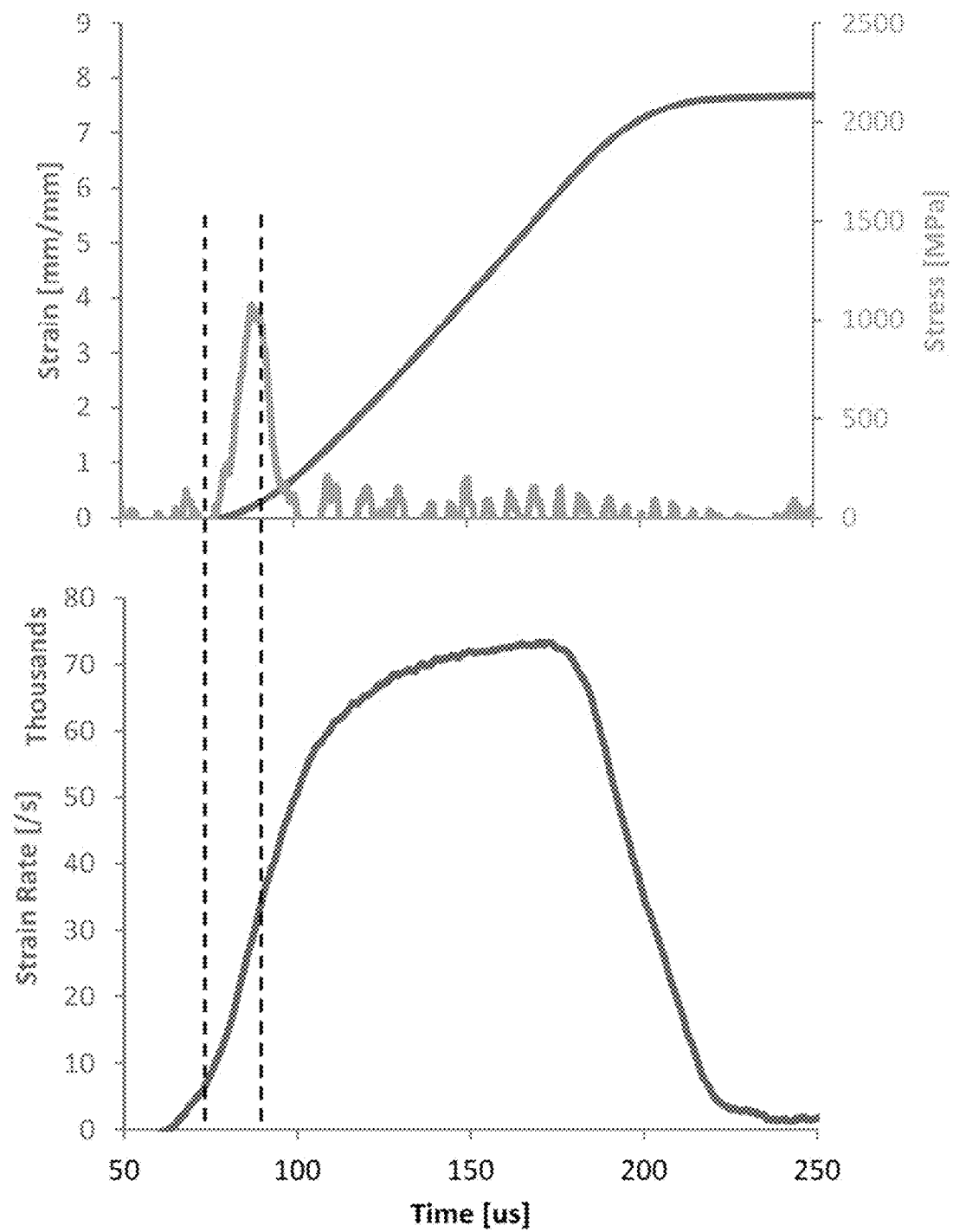
FIG. 9 shows stress, strain, and strain rate for the 0.25 hr tempered sample, according to one embodiment of the invention.
Figure 10:
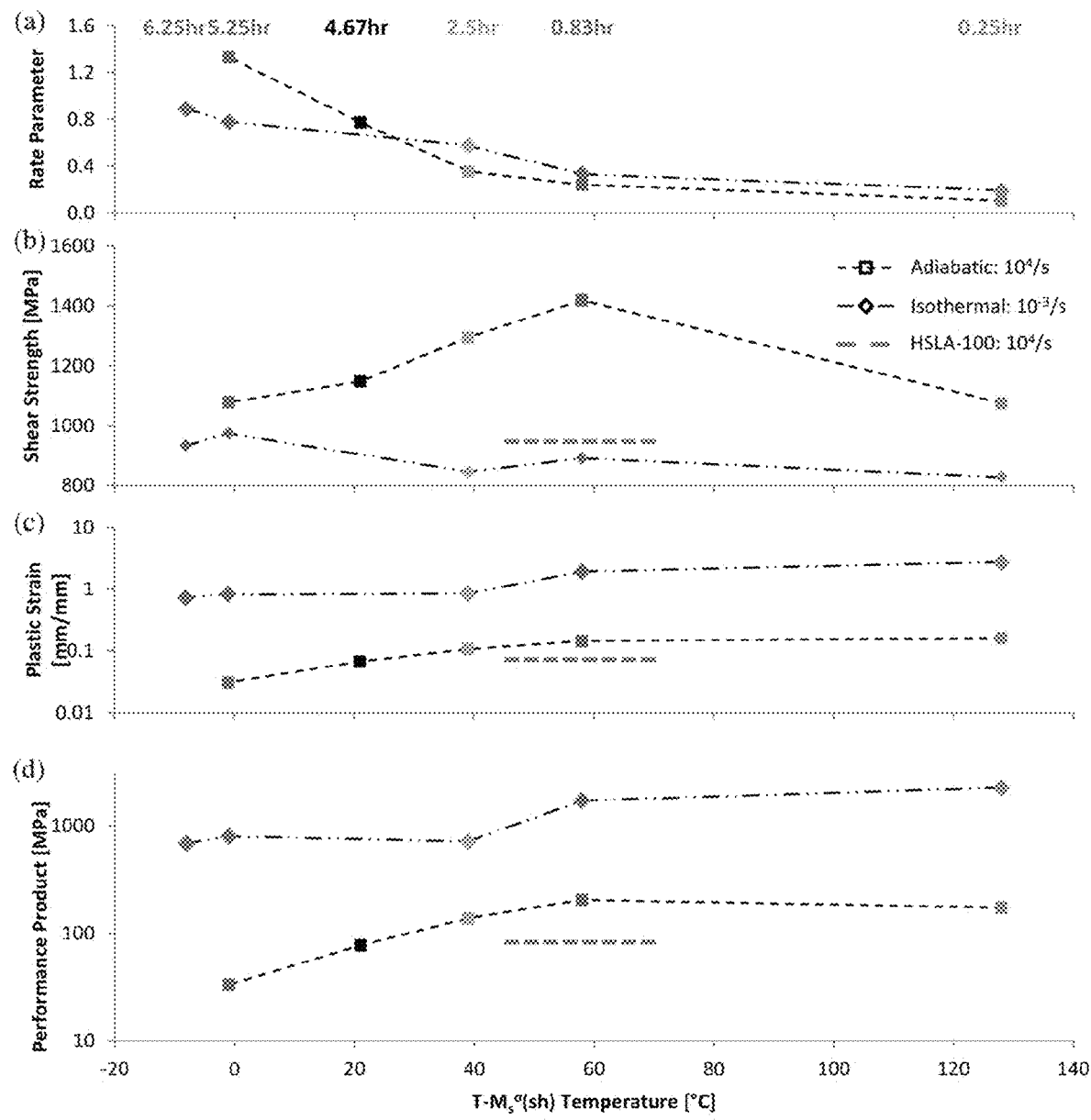
FIG. 10 shows rate parameter (a), shear ultimate strength (b), plastic strain (c), and performance product (d) for quasi-static/isothermal and dynamic/adiabatic TRIP-180 tests and dynamic/adiabatic HSLA-100 tests as a function of austenite stability, according to one embodiment of the invention.

FIG. 8 shows this process where the starts of each wave are aligned in time so that the wave and its expected counterpart (e.g., the incident wave and the transmitted wave minus the reflected wave) per Equation (2) are equal. In a perfect system, they would be exactly equal and the rise at the beginnings of the waves would be a step function. Between the tests, the strain rate varies from $9.4*10^3$ s$^{-1}$ to $3.2*10^4$ s$^{-1}$ with an average of $2.2*10^4$ s$^{-1}$. The strain rates are taken as an average during the entire loading of the sample as the rate changes with time. The evolution of stress, strain, and strain rate is shown in FIG. 9. The dashed lines indicate when the sample was being loaded to failure and represents the order of magnitude of 10 to 15 μs. During tenite matrix and thus decreases stability, raising the $M_s^\sigma$ temperatures and lowering $T-M_s^\sigma$. This decrease in stability leads to greater amounts of transformed martensite and a higher rate parameter. This trend is consistent with the trend in the quasi-static tests as seen in FIG. 10(a) where the square data points are dynamic/adiabatic results and the diamond data points are quasi-static/isothermal results. The amount of plastic strain increases with increasing austenite stability due to lower strength levels from less tempering as also seen in the quasi-static tests and shown in FIG. 10(c).

Figure 11:
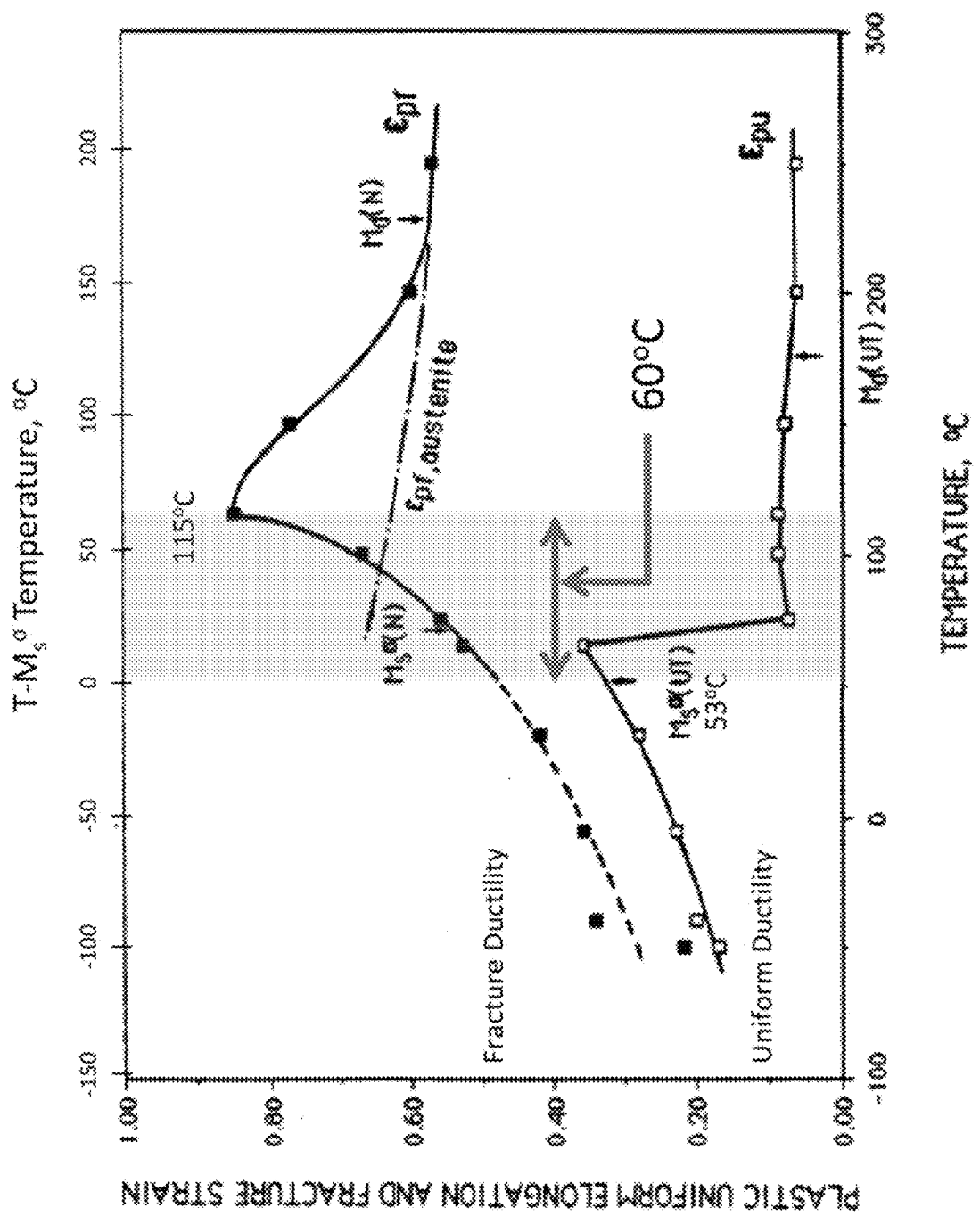
FIG. 11 shows uniform and fracture ductility for an overaged 0.5Mn steel in tension, according to one embodiment of the invention, showing an optimum at T−$M_s^o$(u.t.)=60° C. [24].

The peak in shear ultimate strength changes from the 5.25 hr tempered sample (where $T-M_s^\sigma(sh)\approx 0°$ C.) to the 0.83 hr tempered sample (where $T-M_s^\sigma(sh)\approx 60°$ C.). Seen without a significant drop in failure strain or plastic strain, this leads to a peak in the performance product with a broad optimum around $T-M_s^\sigma(sh)=60°$ C. This is shown in FIGS. 10(b) and 10(c) where the performance of dynamically tested HSLA-100 is also shown. The HSLA-100 data is displayed as a dashed line as it is fully martensitic and thus has no austenite stability to be plotted on the x-axis. It is shown that TRIP-180 at its optimal austenite stability has a 1.5 times greater strength, a 1.6 times greater amount of plastic strain, and a 2.3 higher performance product level than HSLA-100 [23]. As seen in FIG. 11, this fits well into research by Young which shows optimal fracture ductility for isothermal tension peaking 60° C. above the $M_s^\sigma$(u.t.) temperature [24].

Figure 12:
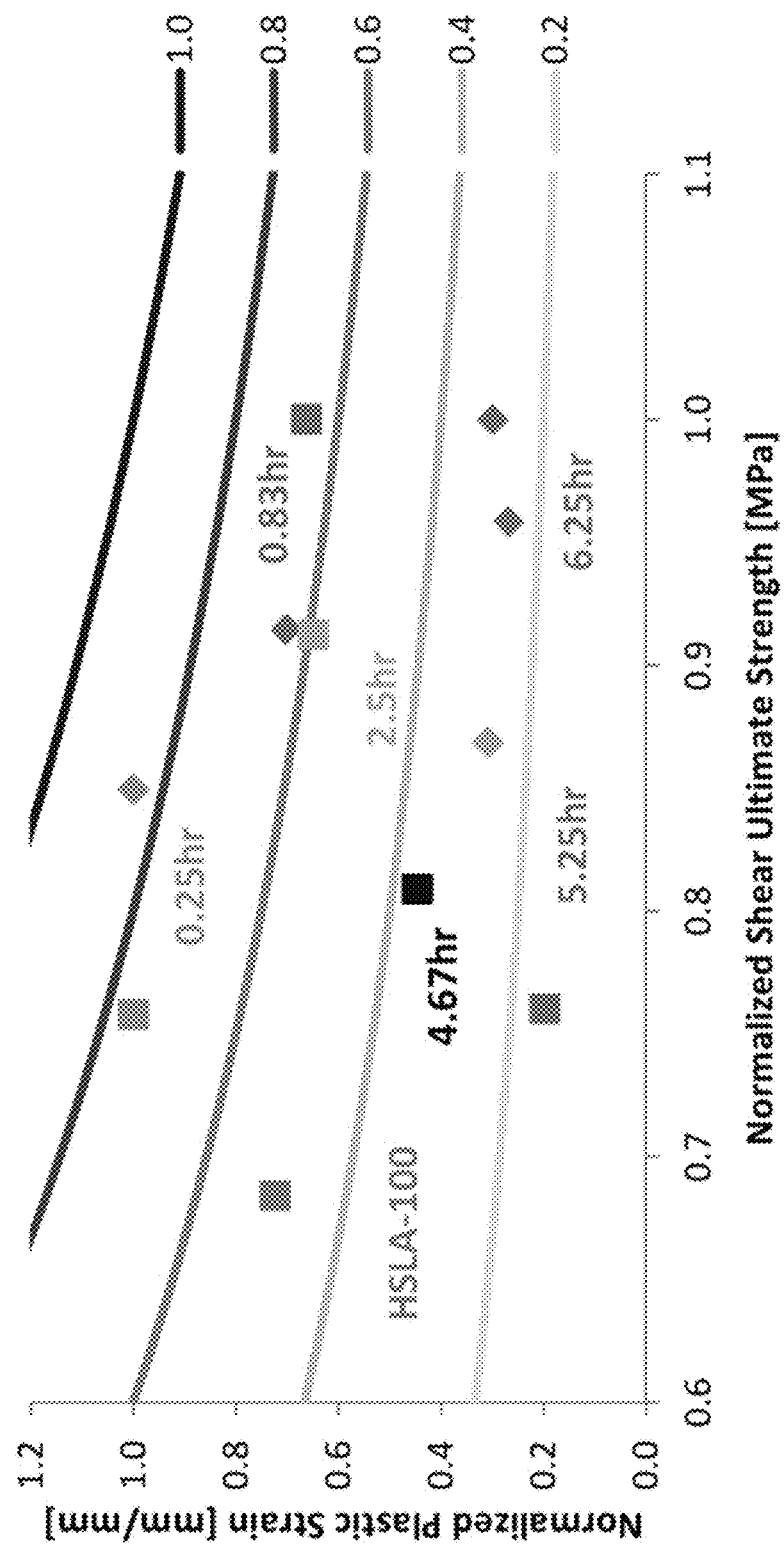
FIG. 12 shows construction of performance product using normalized values for plastic strain and shear ultimate strength for both isothermal and adiabatic conditions.
Figure 13:
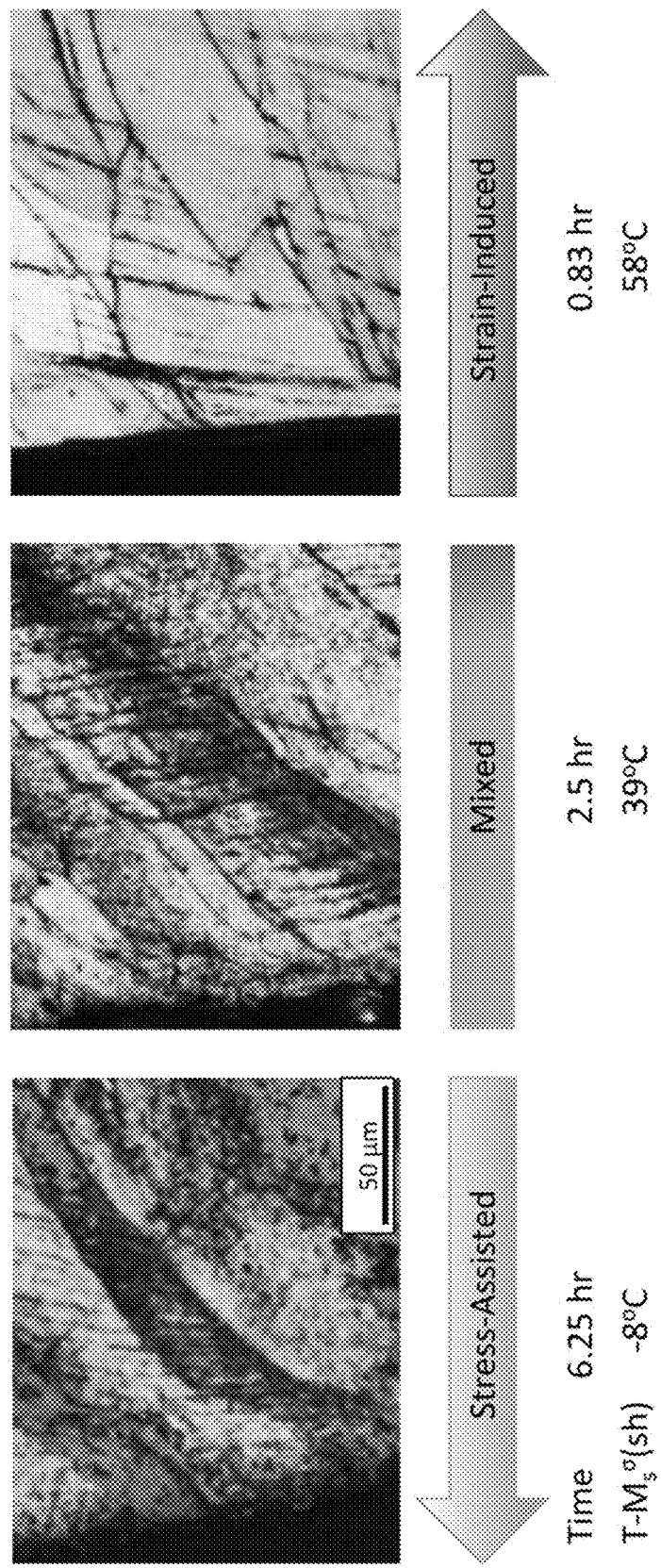
FIG. 13 shows microstructures of failed dynamic hat samples as a function of austenite stability. Tempering time at 700° C. and T−$M_s^o(sh)$ values are given to illustrate the transition from stress-assisted, plate morphology, martensite to strain-induced, lath morphology, when T−$M_s^o(sh)$ passes through zero. Samples are etched with sodium metabisulfite, according to one embodiment of the invention.

FIG. 12 shows a graphical representation of the performance product values with superimposed isocontours of performance product. The values are listed as normalized because the shear strength approaches a factor of two difference and the plastic strain is over an order of magnitude different between the isothermal and adiabatic conditions. Each value was normalized to the maximum value within each loading condition. When evaluating the performance of TRIP steels, examination of the microstructure can confirm austenite stability and help explain if the performance is related to transformation plasticity or another mechanism (e.g., γ' strengthening in this analysis). FIG. 13 shows the evolution of martensite morphology as a function of stability. In the least stable sample, the 6.25 hr tempered sample, the distinct stress-assisted plate type morphology can be seen even though some of the martensite boundaries are not clearly defined. This definition is clearly lost once the transition to temperatures above $M_s^o(sh)$ is made. In the most stable sample, the 0.83 hr tempered sample, clear evidence of the strain-induced, finely dispersed martensite product originating at shear band intersections is seen. At the 2.5 hr tempered sample, a mix of morphologies is seen where both plate-like and finely dispersed martensite products are present. At temperatures around the $M_s^o$ temperature, a mix of morphologies is present as shown in work by Olson [15]. This leads to the determination that strain rate effects are shifting the realized $M_s^o(sh)$ where the temperatures presented in FIG. 13 are calculated for quasi-static loading conditions. This shift could raise the $M_s^o(sh)$ to $M_s^o(sh^{dyn})$ by tens of degrees.

1.3 Fragment Simulating Projectile (FSP) $V_{50}$ Ballistic Testing

Following the conclusion and analysis of the HAT-type dynamic tests, preparation for the FSP $V_{50}$ ballistic penetration tests began. This required tempering the remaining sections of the two remaining 36% warm working reduction in area plates and grinding to a 12.7 mm (0.5 in) thickness to remove any oxide layer and ensure the faces are flat for testing. To prepare the HSLA-100 plate, it was first saw cut to 0.457 m (18 in) square and then ground to a final thickness of 12.7 mm (0.5 in) as it has already been optimally heat treated. As the HSLA-100 provided by Dr. Zhang at the Carderock Division of the Naval Surface Warfare Center was at a thickness of 44.45 mm (1.75 in), and a grinding to a 12.7 mm plate could alter the properties, a second 0.305 m (12 in) square HSLA-100 plate at a 19.05 mm (0.75 in) thickness was provided and ground to 12.7 mm by Jonathan Montgomery, formerly of the Army Research Laboratory at Aberdeen Proving Grounds in Aberdeen, Md. The heat treatment of the TRIP-180 plates was performed at FPM Heat Treating in Elk Grove Village, Ill. in vacuum with an air quench. The grinding of the TRIP-180 plates and the HSLA-100 plate from Dr. Zhang was performed at Precision Grinding also in Elk Grove Village, Ill. by a Blanchard grind removing similar thicknesses from the top and bottom. The tempering times for the TRIP-180 plates was selected by comparing the performance product and its components, plastic stain and shear ultimate strength, of the results from the HAT-type dynamic tests. FIGS. 10(b), 10(c), 10(d), and 12 were consulted. The 0.83 hr tempered condition provided the highest strength and greatest performance product and was selected for ballistic testing. The second condition selected was the 2.5 hr temper as it has a higher strength than the 0.25 hr temper (albeit a lower performance product) and a more easily obtained heat treatment time for industrial furnaces as the temper times are not including heat up time of the plate. Table 3 provides an overview of the four plates ballistically tested including sizes and notes.

TABLE 3

Plate descriptions for the FSP $V_{50}$ ballistic tests. Sizes are in meters (inches).

| | Material | Size | Notes |
|---|---|---|---|
| Plate 1 | TRIP-180 | 0.394 × 0.140 (15.5 × 5.5) | tempered for 2.5 hr at 700° C. |
| Plate 2 | TRIP-180 | 0.349 × 0.260 (13.75 × 10.25) | optimally tempered for 0.83 hr at 700° C. |
| Plate 3 | HSLA-100 | 0.457 sq. (18 sq.) | received from Zhang, starting thickness of 44.45 mm (1.75 in) |
| Plate 4 | HSLA-100 | 0.305 sq. (12 sq.) | received from Montgomery, starting thickness of 19.05 mm (0.75 in) |

1.3.1 Experimental Results

Figure 14:
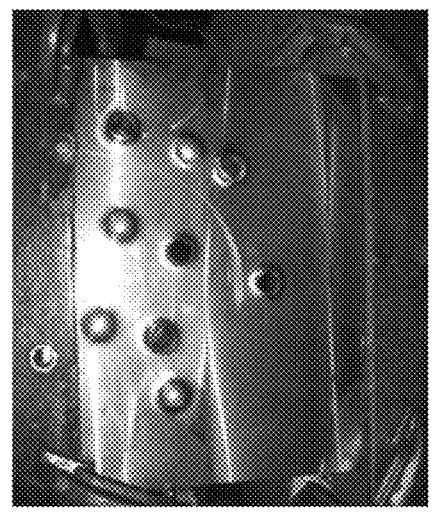
FIG. 14 shows images of Plate 4 during testing showing (a) the test setup with the plate clamped to the frame and the witness plate suspended behind, (b) the front of the plate after a series of shots, and (c) the back of the plate after a series of shots, according to one embodiment of the invention.
Figure 14:
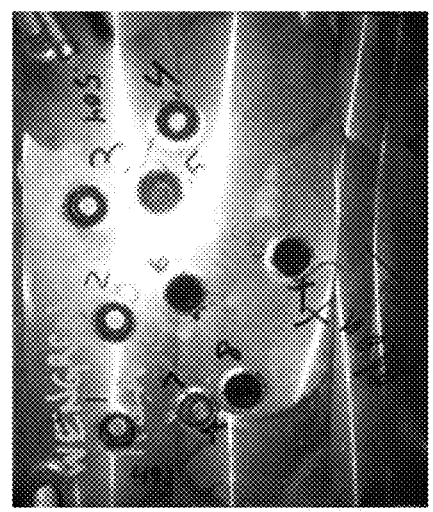
Figure 14:
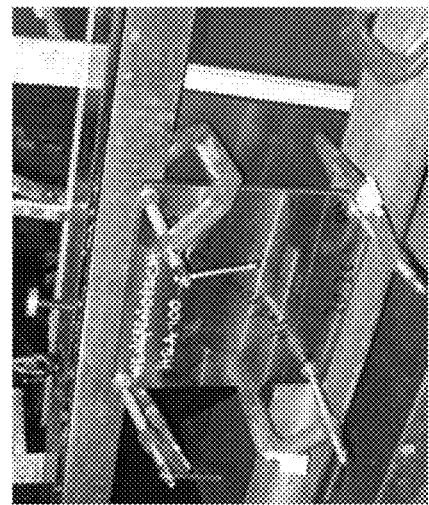

The four plates were tested in the following order: Plate 3, Plate 4, Plate 1, Plate 2. The HSLA-100 plates were tested first to give baseline on a starting velocity for the TRIP-180 plates. The HSLA-100 plates were shot until a six round (three highest partial and three lowest complete) ballistic limit was calculated. The TRIP-180 plates were shot until all usable space on the plate was utilized. FIG. 14 shows the testing of Plate 4. The testing fixture in FIG. 14(a) is moved to align each shot. When approaching edges or clamps, the clamps and the plate's position on the crossbars can easily move as to not interfere with the projectile and cause a bad hit causing that shot to be ignored.

Figure 15:
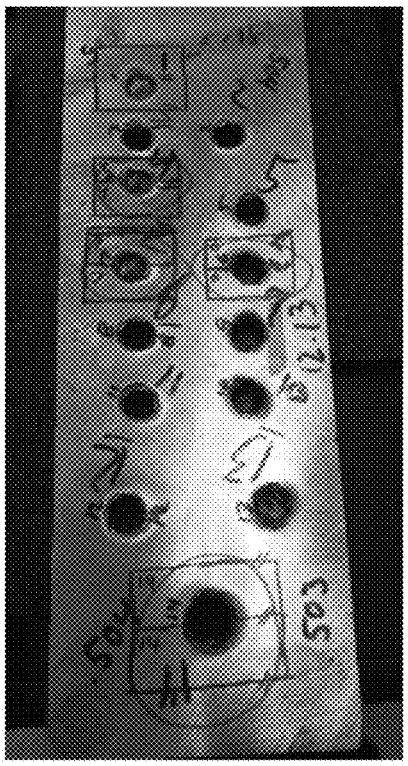
FIG. 15 shows fronts of plates showing shots and resulting impact sites for (a) Plate 1, (b) Plate 2, (c) Plate 3, and (d) Plate 4, according to one embodiment of the invention.
Figure 15:
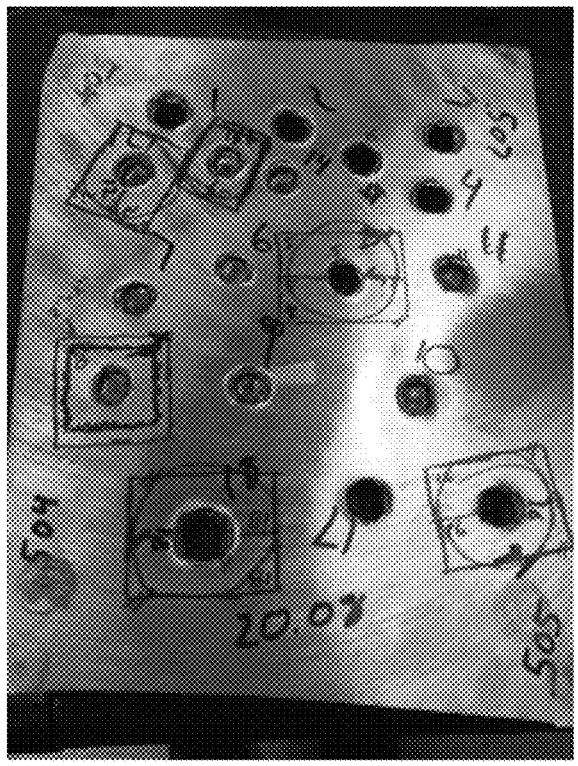
Figure 15:
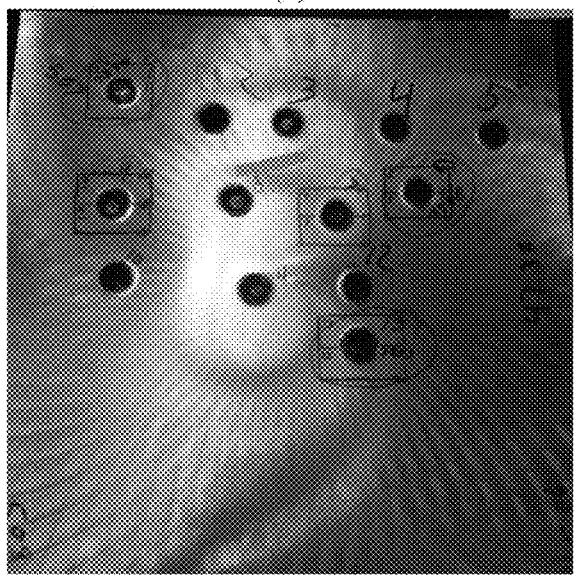
Figure 15:
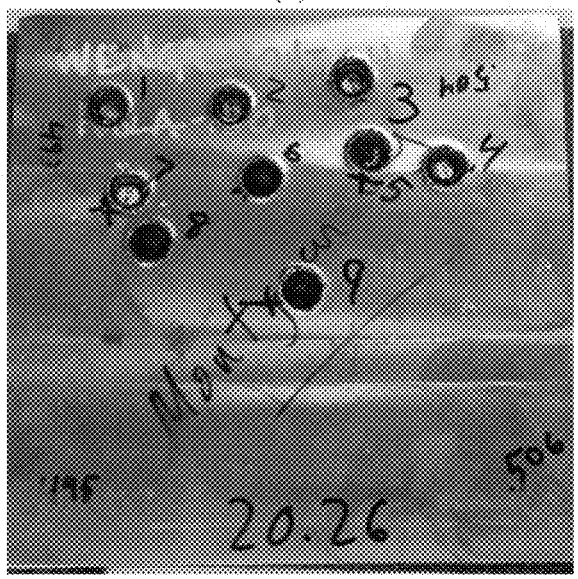
Figure 16:
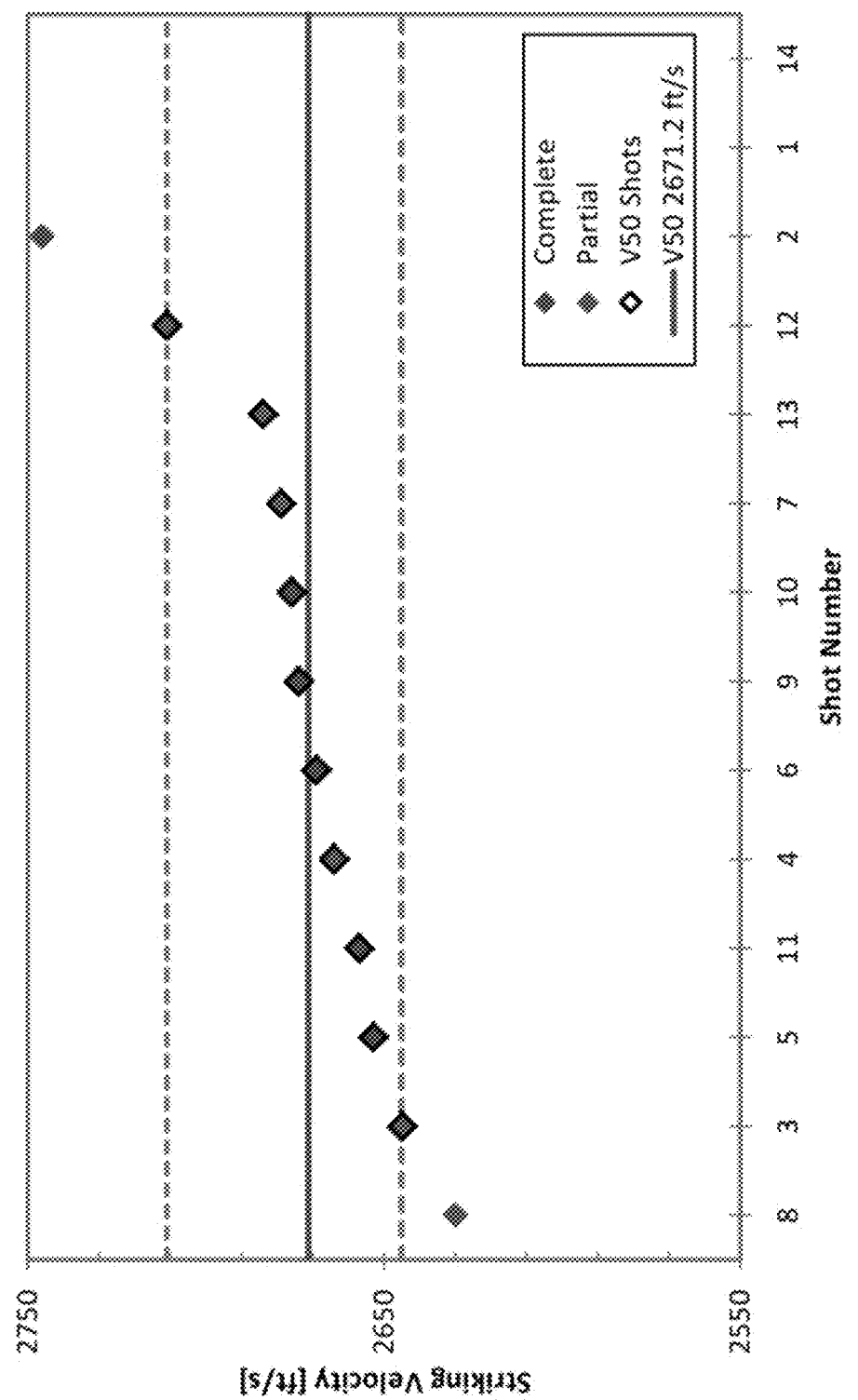
FIG. 16 shows results of fragment simulating projectile (FSP) V$_{50}$ test performed on Plate 1, sub-optimal tempered TRIP-180 for 2.5 hr at 700° C., according to one embodiment of the invention.
Figure 17:
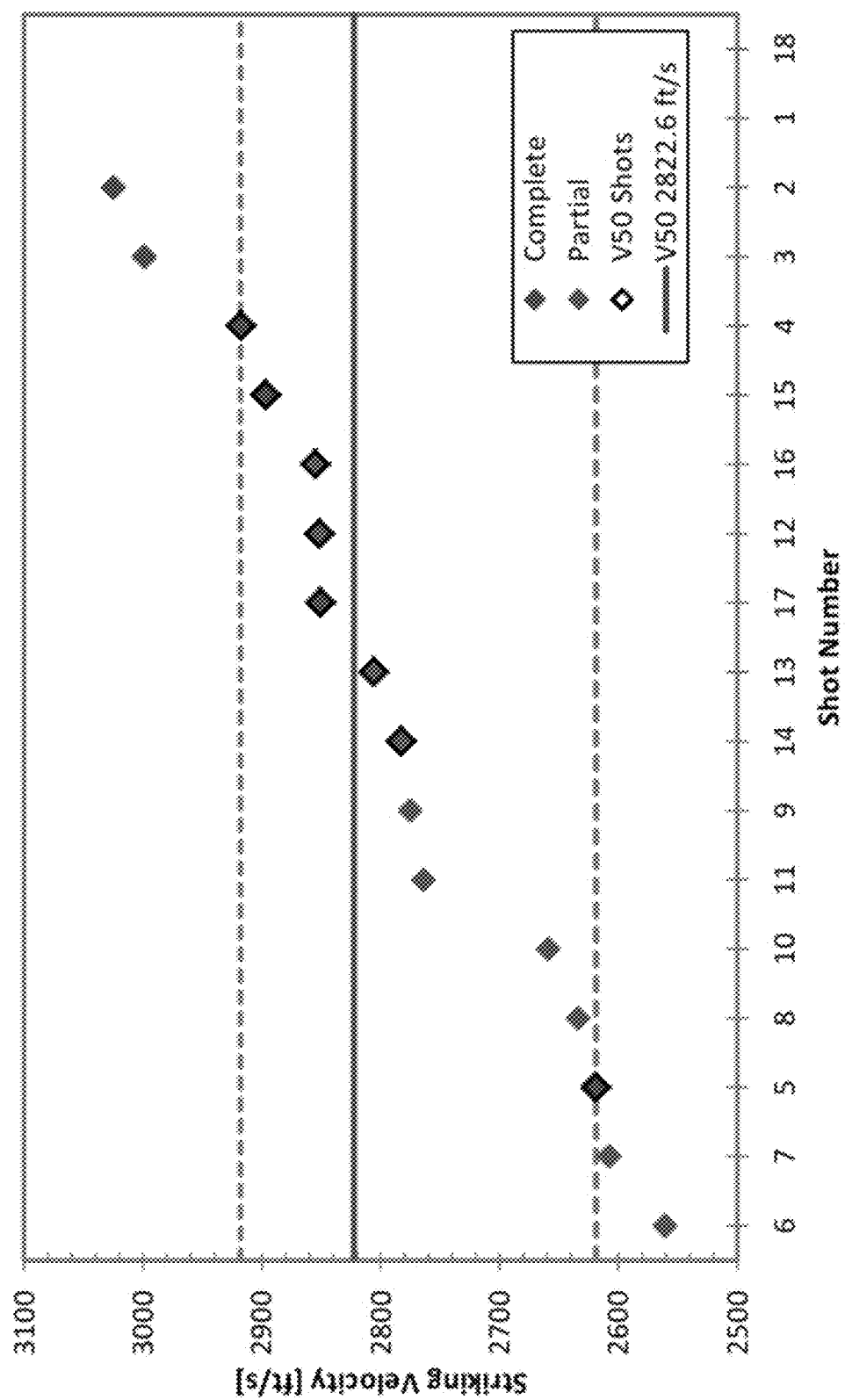
FIG. 17 shows results of FSP V$_{50}$ test performed on Plate 2, optimally tempered TRIP-180 for 0.83 hr at 700° C., according to one embodiment of the invention.
Figure 18:
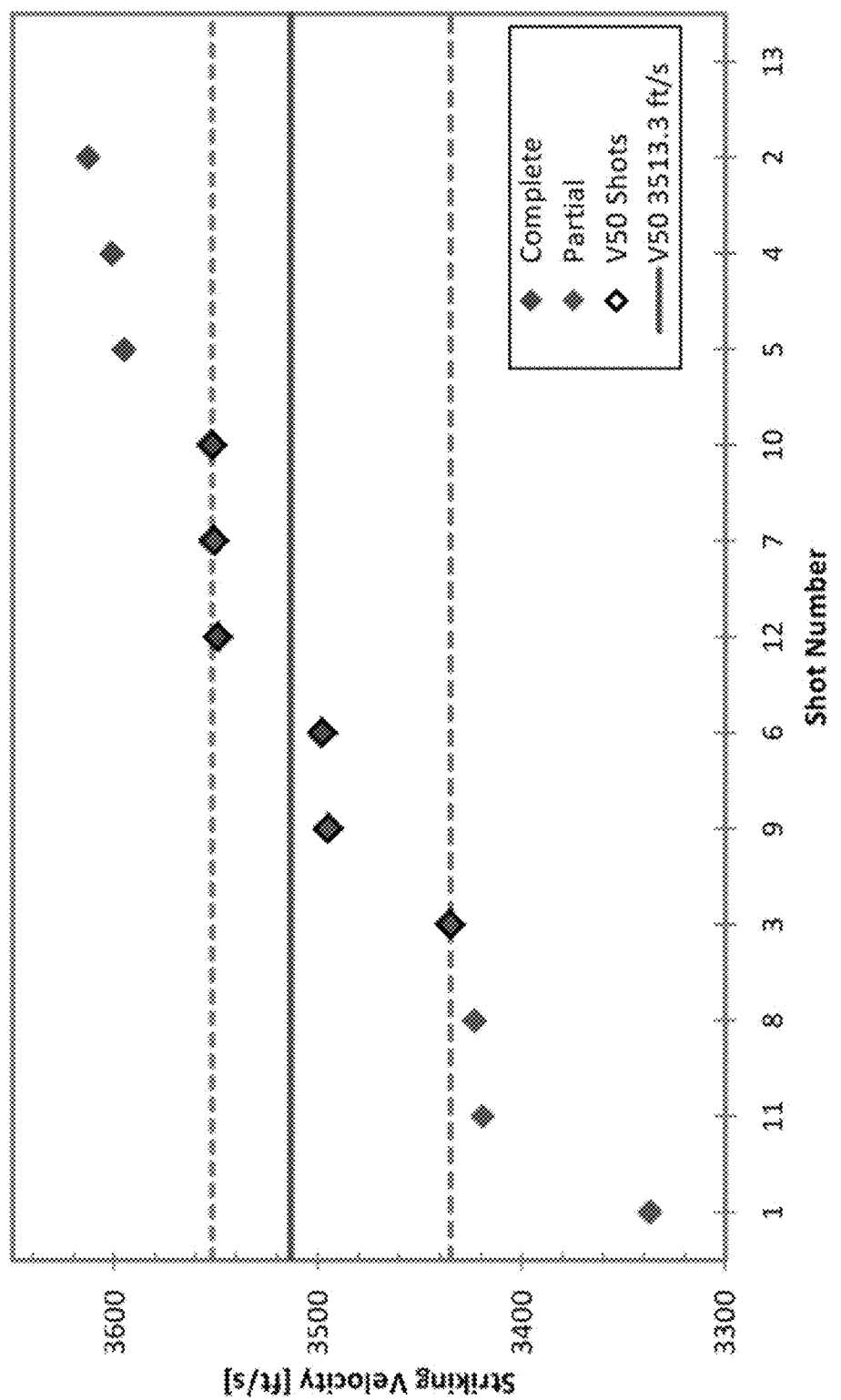
FIG. 18 shows results of FSP V$_{50}$ test performed on Plate 3, HSLA-100 received from Zhang originally 44.45 mm thick, according to one embodiment of the invention.

FIG. 15 shows the fronts of each plate after testing where it can been seen that Plate 1 had fourteen shots, with one being a bad hit (shot too close to frame), Plate 2 had eighteen shots, Plate 3 had thirteen shots, and Plate 4 had nine shots. The markings indicate thicknesses at the corners, overall weight, shot number, and shots to be cut out for analysis. For Plate 1 this includes shot number 1, 4, 6, 7, and 11. For Plate 2 this includes shot number 5, 8, 12, 13, 16, and 18. For Plate 3 this includes shot 1, 6, 7, 9, and 13. None were cut for Plate 4 as the performance was nearly identical to Plate 3.

Table 4 compiles the results of the tests. The $V_{50}$ speed is calculated as an average of an equal number of the highest speed partial penetrations and the lowest speed complete penetrations. The number of points used to calculate the $V_{50}$ speed is given in the following row where a value of 10 refers to 5 partial penetrations and 5 complete penetrations. The speed for the highest partial and lowest complete are listed. The range of results, ROR, is taken as the difference between the highest speed and lowest speed shot used in the calculation of the $V_{50}$ speed regardless of penetration type. The range of mixed results, MIR, is calculated as difference between the speeds of the highest partial penetration and lowest complete penetration. As the $V_{50}$ speed is a statistical representation of the speed at which 50% of the projectiles completely penetrate the material and not the $V_0$ speed, the speed at which 0% of projectiles penetrate, there can be higher partial penetration speed and a lower complete penetration than the $V_{50}$ giving rise to positive MIR values. By their definitions, the ROR is always greater than the MIR.

TABLE 4

Results for FSP $V_{50}$ ballistic tests for four plates. Speeds are given in ft/s, the standard reporting units in the field.

| | TRIP-180 | | HSLA-100 | |
|---|---|---|---|---|
| | Plate 1 | Plate 2 | Plate 3 | Plate 4 |
| Number of Shots | 14 | 18 | 13 | 9 |
| BL(P) $V_{50}$ | 2671 | 2823 | 3513 | 3524 |
| Number of Points for $V_{50}$ | 10 | 8 | 6 | 6 |

TABLE 4-continued

Results for FSP $V_{50}$ ballistic tests for four plates. Speeds are given in ft/s, the standard reporting units in the field.

|  | TRIP-180 | | HSLA-100 | |
| --- | --- | --- | --- | --- |
|  | Plate 1 | Plate 2 | Plate 3 | Plate 4 |
| High Partial | 2711 | 2855 | 3551 | 3559 |
| Low Complete | 2653 | 2619 | 3498 | 3430 |
| Range of Results | 66 | 299 | 117 | 142 |
| Range of Mixed Results | 58 | 236 | 53 | 129 |

These results are displayed graphically in FIGS. 16-19. The $V_{50}$ speed is given as the solid green line, the ROR indicated by the dashed green lines, the complete penetrations as red diamonds, partial penetrations as blue diamonds, and the shots used in the calculation of the $V_{50}$ speed outlined in black. The shots have been arranged in increasing striking velocity. Plates 1, 2, and 3 had a final shot taken at the maximum velocity possible given the barrel used at approximately 4000 ft/s. Plate 1 showed an excellent grouping of results for $V_{50}$ calculation. Plates 3 and 4 showed a decent grouping although with more shots fired, a narrower spread and a lower ROR might have been achieved. Plate 2 showed a significant outlier with shot number 5. If shot 5 is removed from the $V_{50}$ calculation, shot number 14 must also be removed to maintain equal partial and complete penetrations. This would result in a $V_{50}$ speed of 2863 ft/s, a ROR of 112 ft/s, and a RMR of 4 ft/s.

Figure 20:
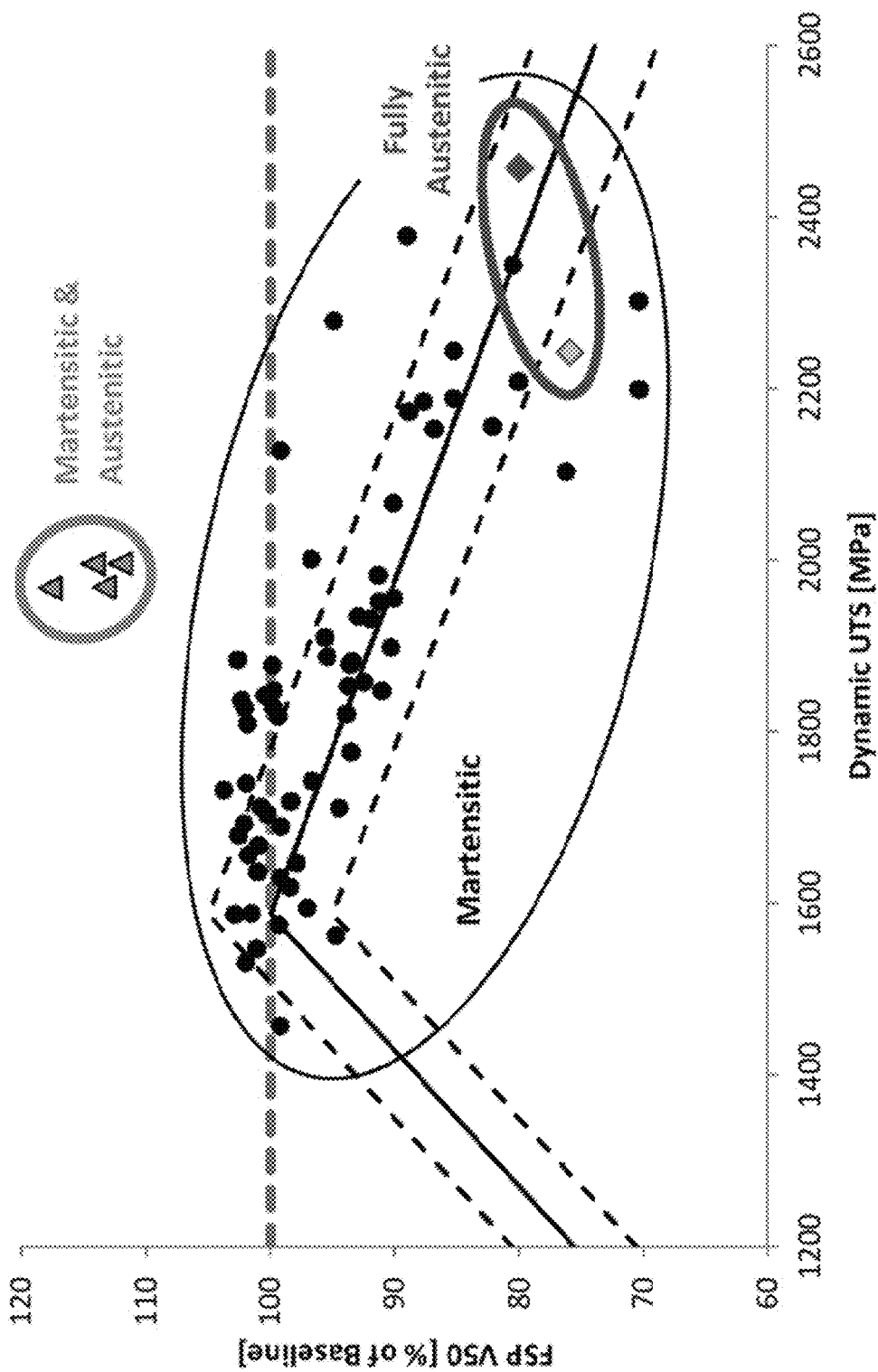
FIG. 20 shows ballistic testing trends showing classical martensitic steel behavior and enhanced martensite plus austenite performance [25] and fully austenitic TRIP-180, according to one embodiment of the invention. Optimal tempered TRIP-180 is shown in red, and sub-optimal in yellow.

The results of the ballistic tests show that TRIP-180, even with greater performance in strength and ductility in dynamic tests did not out perform HSLA-100. The two conditions of TRIP-180 at optimal and sub-optimal tempering performed at 80% and 76% of HSLA-100. The reason could be due to the excessive strength of TRIP-180, where higher strength is required to protect from armored piercing projectiles, but an optimum strength is required to prevent fragment penetration. The ballistic testing trends for martensitic steels, dual phase QLT steels, and fully austenitic steels is shown in FIG. 20 versus dynamic ultimate tensile strength. The conversion between dynamic ultimate shear strength and dynamic ultimate tensile strength for TRIP-180 is done mathematically using the von Mises yield criterion as shown in Equation (3) [13].

$$\tau_{max} = \frac{\sigma_{max}}{\sqrt{3}} \quad (3)$$

Even at higher strength levels, the 0.83 hr tempered TRIP-180 with optimized austenite stability outperformed the 2.5 hr tempered TRIP-180 with sub-optimum austenite stability. This shows that the martensitic transformation, even at low levels due to adiabatic heating, allows for control of ballistic performance. To evaluate the difference in the dynamic deformation and martensitic transformation of the plates, specific impact sites were removed and cross-sectioned. For analysis the impact sites near the $V_{50}$ speeds were investigated. For Plate 1 that includes the impact site shot number 4, 6, and 7. For Plate 2 that includes the impact site from shot number 5, 12, 13, and 16. For Plate 3 that includes shot 6, 7, and 9. To approximate the amount of dynamic deformation, global thickness reduction, $t_{red}^g$, is measured using the ImageJ software of area stitched images. It relates the minimum thickness, $t_{min}$, to initial plate thickness, $t_i$, as seen in Equation (4).

$$t_{red}^g = 1 - \frac{t_{min}}{t_i} \quad (4)$$

Figure 21:
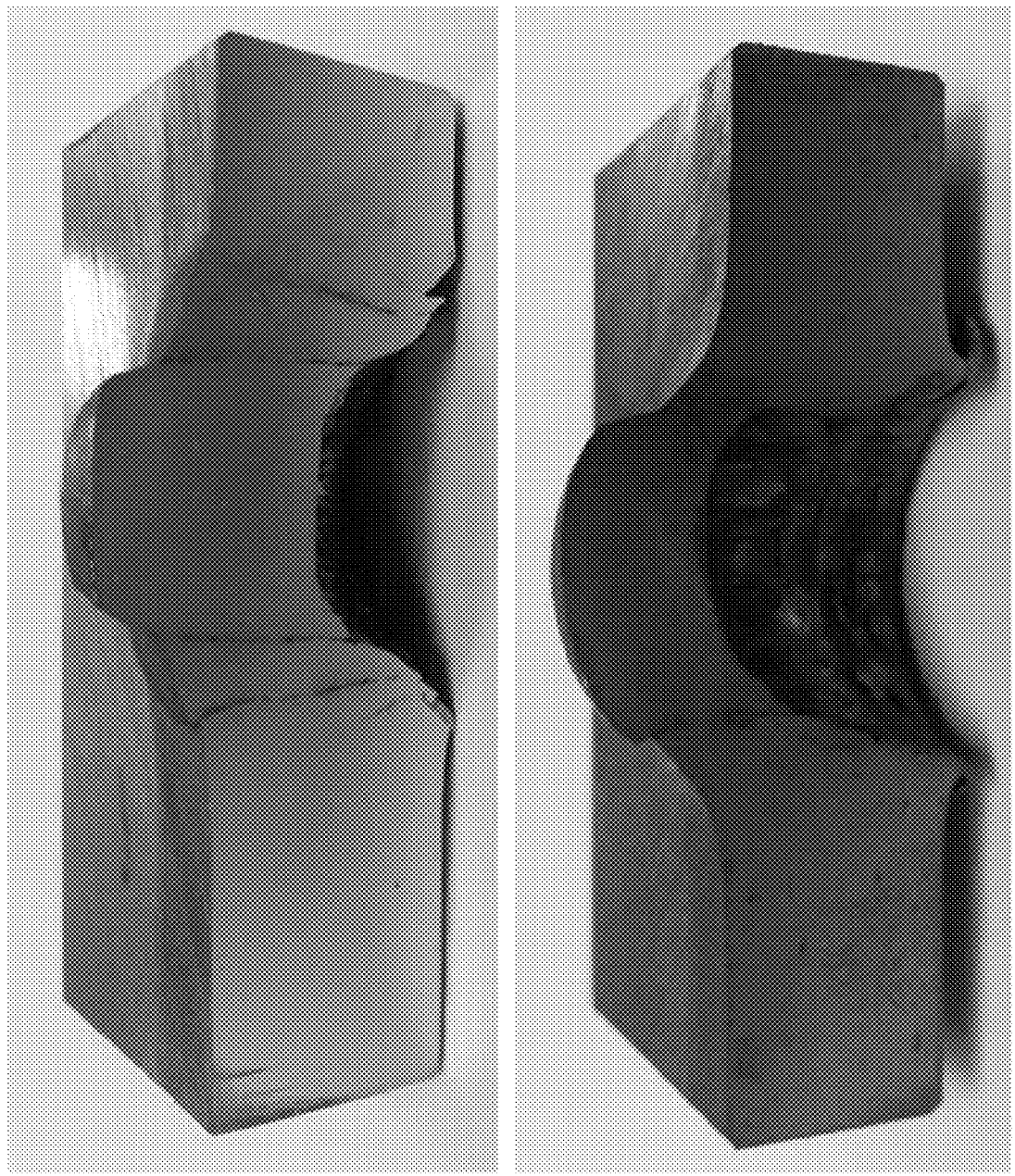
FIG. 21 shows cross-sections of impact sites for (a) TRIP-180 Plate 2 impact site 12 and (b) HSLA-100 Plate 3 impact site 7, according to one embodiment of the invention.

This analysis shows that the HSLA-100 plate (Plate 3) underwent the most dynamic deformation with a global thickness reduction of 39.7%. The optimum tempered TRIP-180 plate (Plate 2) sustained more dynamic deformation than the sub-optimum tempered TRIP-180 plate (Plate 1) with a global thickness reduction of 13.6% versus 6.79%. An representative overview between the deformation seen in the TRIP-180 plates versus the HSLA-100 plates for partial penetrations is shown in FIG. 21. Failures in the TRIP-180 plates tended to be from plugging with the generation of adiabatic shear bands, FIG. 21(a), as opposed to bulging seen in the HSLA-100 plates, FIG. 21(b), for impacts around the $V_{50}$ speed. At much higher velocities, both materials failed in plugging.

1.3.2 Arrested Shear Bands

Figure 22:
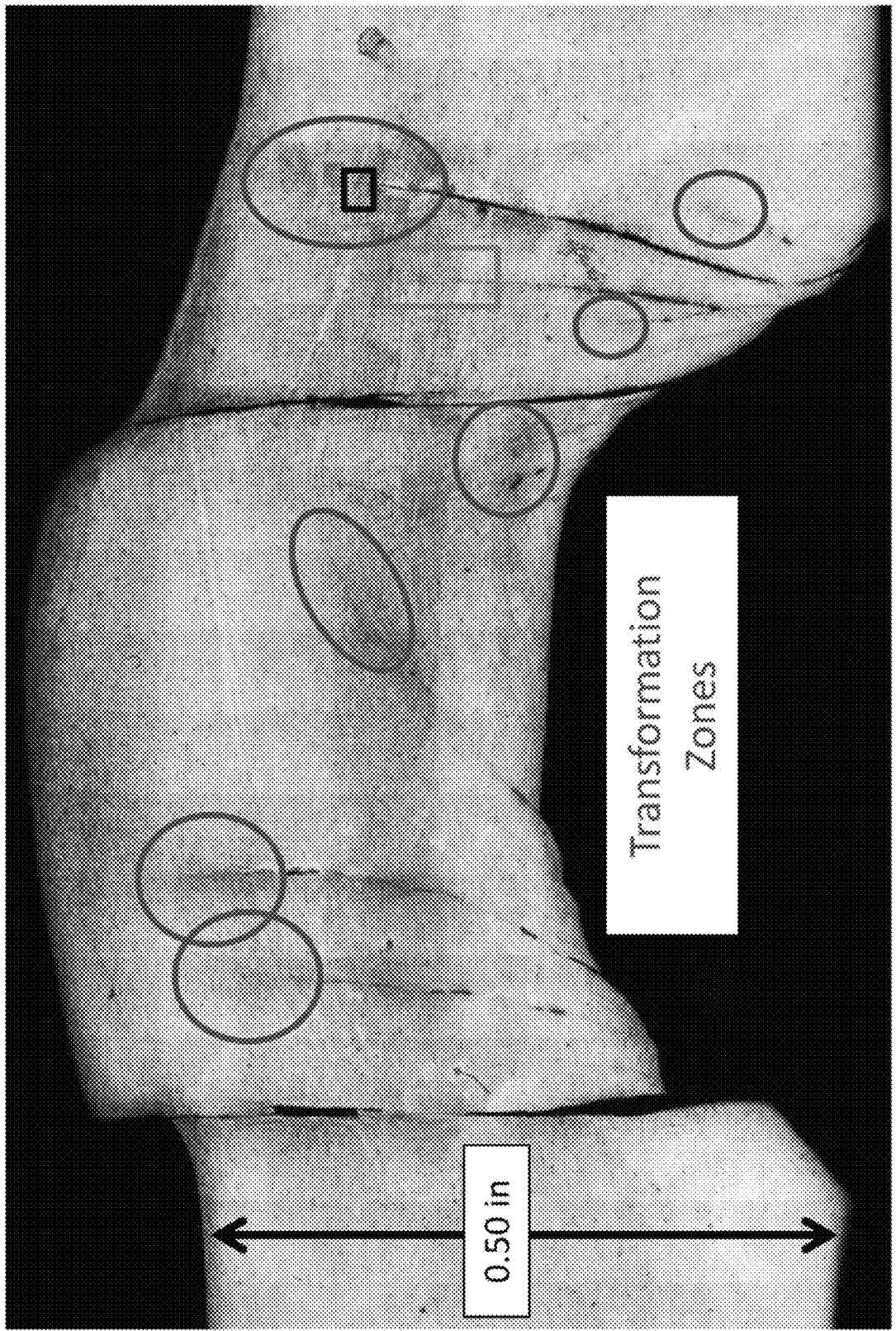
FIG. 22 shows adiabatic shear bands arrested by transforming martensite, highlighted in red, from optimally tempered TRIP-180, Plate 2 impact site number 13, according to one embodiment of the invention.

To investigate the impact of the martensitic transformation on the ballistic performance, optical micrographs of the microstructures of cross-sections of the TRIP-180 impact sites were taken. Within the TRIP-180 samples, it was found that there were multiple arrested adiabatic shear bands in addition to the band that resulted in plugging failure. Reviewing the areas where the adiabatic shear bands terminated, greater amounts of strain-induced martensite, with finely dispersed and plastically deformed morphology, is present. FIG. 22 shows the multiple adiabatic shear bands arrested by transformation zones around impact site number 13 of the optimally tempered TRIP-180, Plate 2.

Figure 23:
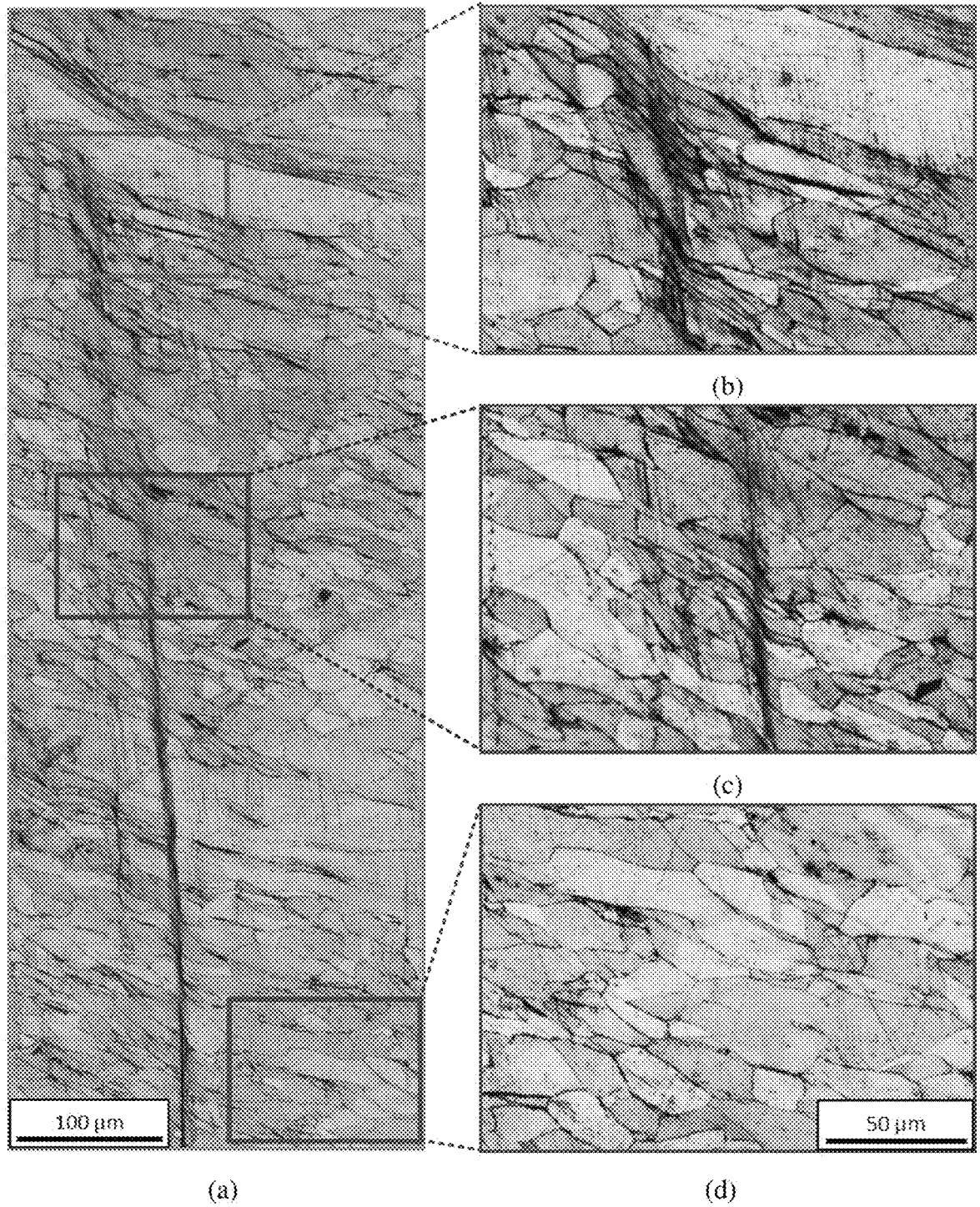
FIG. 23 shows microstructures around an arrested adiabatic shear band (blue rectangle in FIG. 21 in optimally tempered TRIP-180, according to one embodiment of the invention. Microstructure (a) of entire termination of band, (b) in front of termination, (c) at termination, and (d) away from termination.
Figure 24:
FIG. 24 shows microstructures (a) near and (b) at the termination of an arrested adiabatic shear band in optimally tempered TRIP-180, according to one embodiment of the invention. Locations are indicated by the orange and black rectangles in FIG. 21, respectively.
Figure 24:
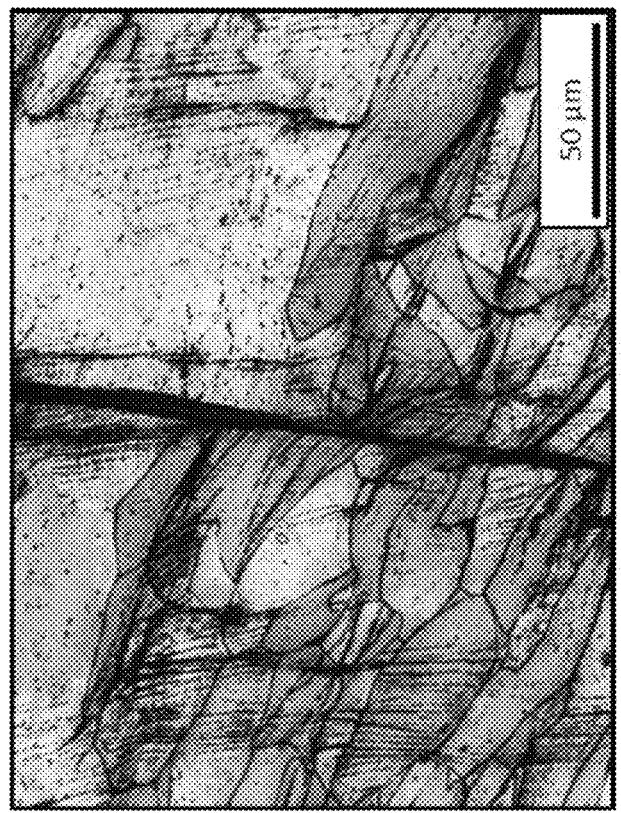

FIG. 23 shows a detailed view of the arrested adiabatic shear band, highlighted in a blue rectangle, developed at an impact speed of 99.4% of the $V_{50}$ velocity. FIG. 23(a) shows an overview of the area leading up to and in front of the termination of the adiabatic shear band while FIGS. 23(b)-23(d) show larger magnifications of specific areas. FIG. 23(d) shows an area with relatively little transformation that is away from the adiabatic shear band. At the termination of the band, FIG. 23(c) shows more transformation than in surrounding areas. The greatest amount of strain-induced transformation is seen in FIG. 23(b) in front of the adiabatic shear band. FIG. 24 emphasizes that same point on a different adiabatic shear band where the amount of strain-induced martensite increases when approaching the termination (FIG. 24(a)) and continuing in front (FIG. 24(b)) of the band. The strain hardening from the martensitic transformation (i.e., transformation plasticity) successfully countered the strain softening of the microvoid nucleation and coalescence seen in shear loading.

1.4 Atom Probe Tomography Analysis

Three-dimensional atom probe tomography was performed on nine different conditions of TRIP-180. All were tempered at 700° C. for a specified number of hours. The data generated was then used to calibrate interfacial energies of the γ' strengthening phase, strength models and matrix compositions for calculation of $M_s^o$ temperatures, and general precipitation kinetics through PrecipiCalc modeling.

1.4.1 Experimental Results

Figure 19:
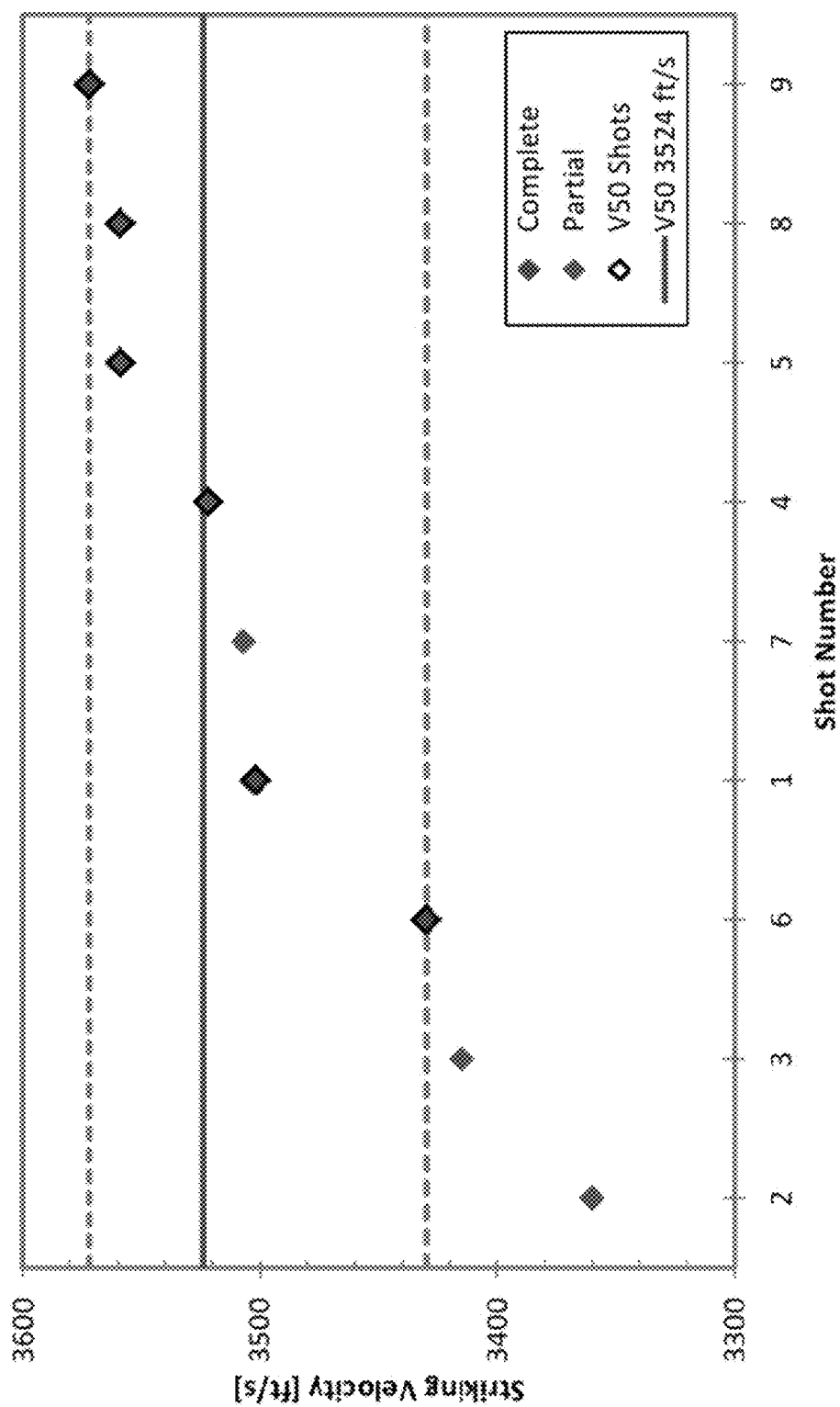
FIG. 19 shows results of FSP V$_{50}$ test performed on Plate 4, HSLA-100 received from Montgomery originally 19 mm thick, according to one embodiment of the invention.

The tempering times for the TRIP-180 samples studied in the LEAP are as follows: 0.125 hr (7.5 min), 0.25 hr (15 min), 0.5 hr (30 min), 0.83 hr (50 min), 1 hr, 2.5 hr, 5 hr, 8 hr, and 16 hr. A typical LEAP run gathered 25 to 75 million atoms that provide critical data to understanding the temporal evolution of the γ' precipitates. FIG. 19 shows an example of the 1 hr tempered TRIP-180 where 35.1 million atoms were collected and reconstructed using the Imago data analysis software. The reconstructed tip is approximately 110 nm long and 60 nm in diameter. All atoms are hidden for clarity except for iron atoms, shown as orange dots. A 45 at. % nickel isoconcentration surface is shown in purple to define the γ' precipitate boundaries. This indicates that the nickel concentration is greater than 45 at. % within the purple surfaces.

The atoms are identified by setting specific ranges on a mass-to-charge ratio spectrum by using isotopic masses and probable charge states of the atoms. These ranges generally fall over "peaks" in the spectrum at specific values that have been well tabulated. Peaks of impurities, such as iron oxides or copper can be discarded. Iron and other oxides are generally only found at the beginning of the LEAP run or near the edges of the tip. They are generally excluded by geometrically narrowing the diameter of the tip and ignoring the edge data and by excluding the first 8 to 10 million atoms as the LEAP run stabilizes. The selection of peaks can be seen in FIG. 26 where the ranges for each atom are highlighted by their color and extraneous peaks are ignored. The plot reads as the number of ions recorded (counts) at each mass-to-charge ratio. One artifact of having a large number of elements in TRIP-180 results in overlapping peaks as indicated by the gray ranges with arrows. The ions and their charge states at each peak are identified. For bulk composition analysis, the Imago software can decompose each peak of multiple ions into its proper ions. To produce accurate proximity histograms however, the ions in the reconstructed data file need to individually be identified to a specific ion, and not a set of possible ions. To do this, a python code was written to manually deconvolute each multiple peak and assign each ion to a different, individual peak. The code calculated expected counts for each ion in each multiple peak by evaluating the isotopic abundances of individual peaks for each ion. The code then calculates a probability for each type of ion and randomly associates all ions in the overlapping peaks to a specific ion given the probabilities and rewrites the mass-to-charge ratio within the reconstructed data file. An example of this is shown for a small range of mass-to-charge ratios in FIG. 11, the same mass-to-charge ratio spectrum in FIG. 26. FIG. 27(a) shows the initial spectrum, and FIG. 27(b) shows the deconvoluted spectrum where the ions in the peak around mass-to-charge ratio of 27 ($Fe^{2+}$, $Cr^{2+}$, and $Al^{1+}$) are sorted into peaks 28 for Fe, 26 for Cr, and 13.5 for Al.

Figure 26:
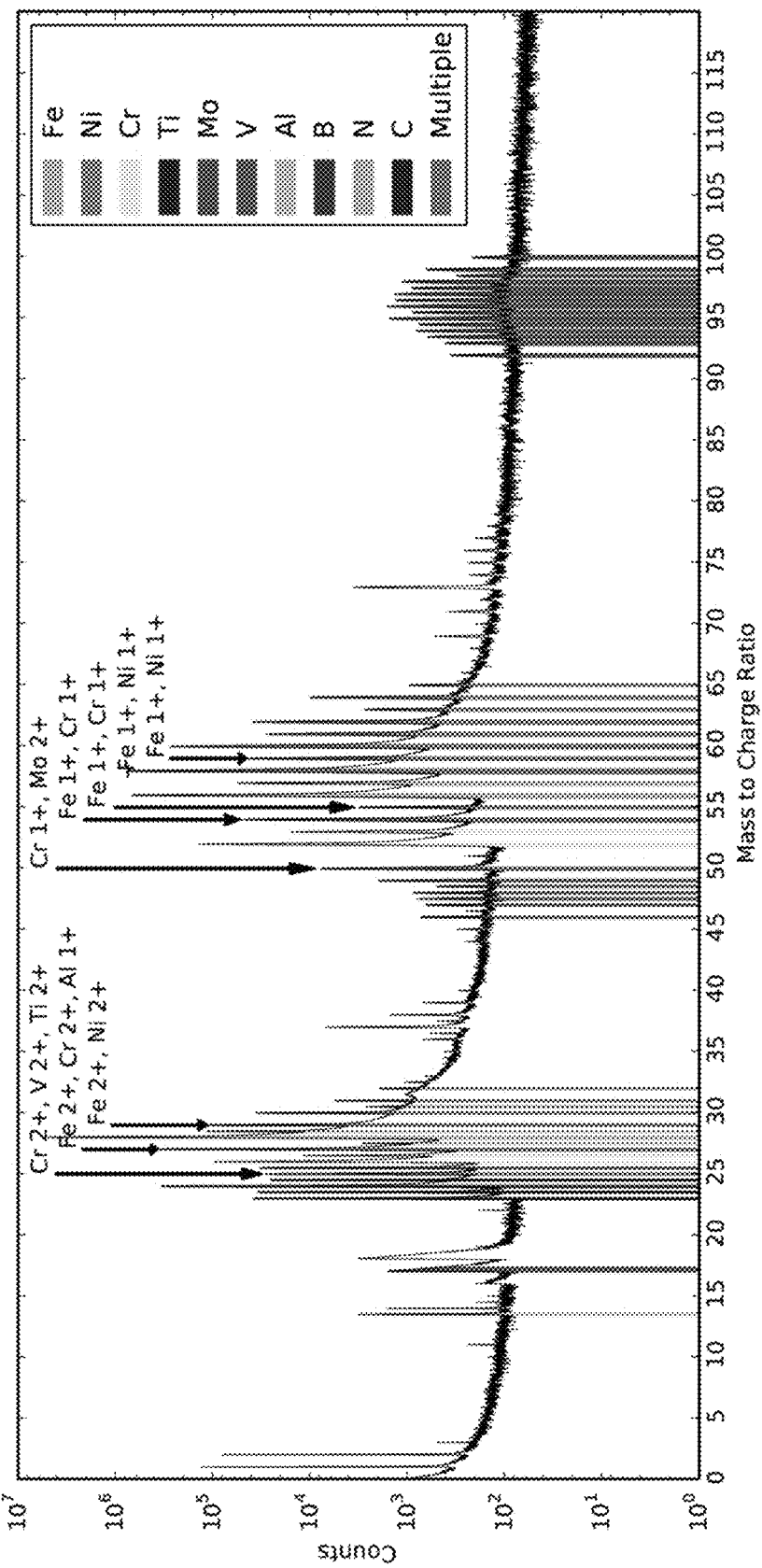
FIG. 26 shows a mass-to-charge spectrum of TRIP-180 tempered at 700° C. for 16 hr. Ranges with multiple possible ions are shown in gray with arrows, according to one embodiment of the invention.
Figure 27:
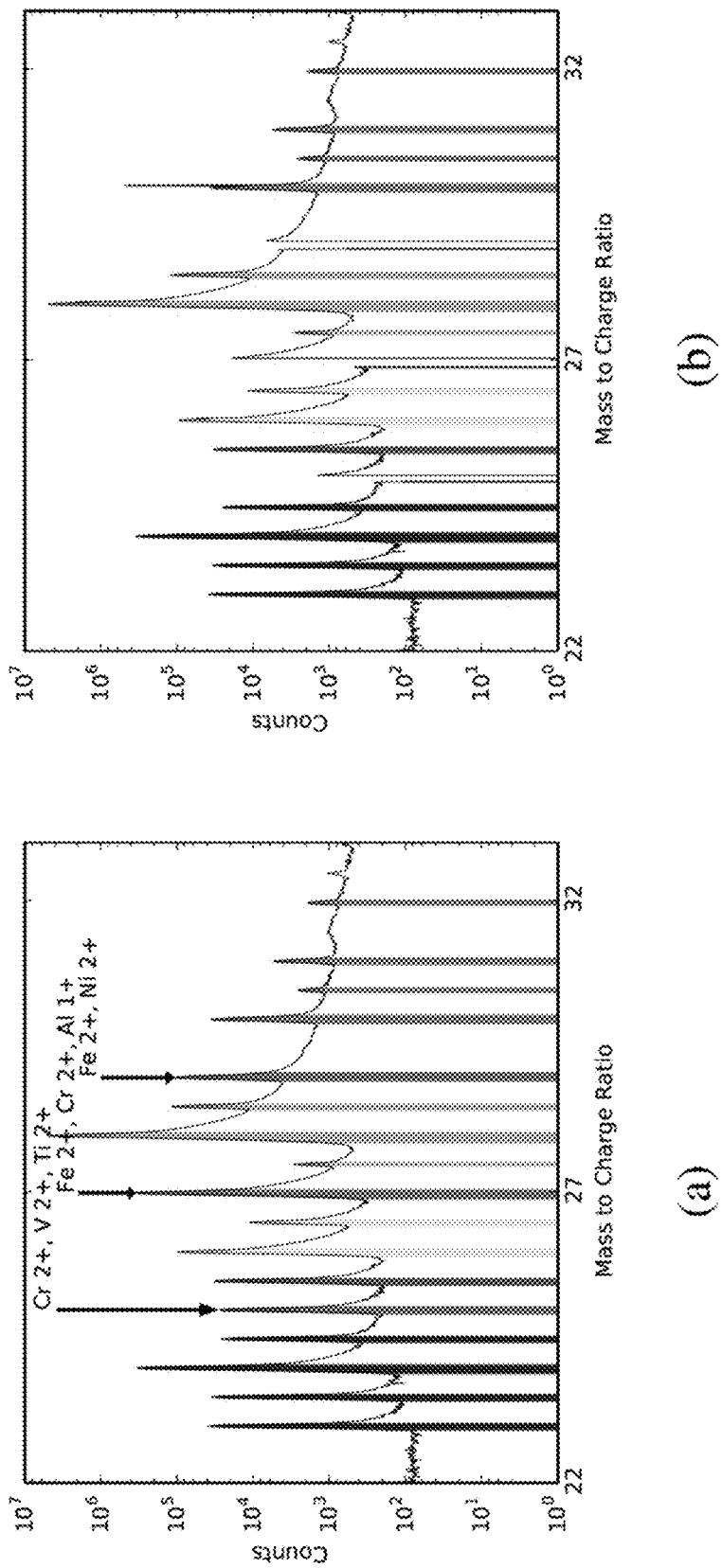
FIG. 27 shows mass-to-charge spectra of TRIP-180 tempered at 700° C. for 16 hr. Spectrum is shown (a) before and (b) afterwards, according to one embodiment of the invention.
Figure 28:
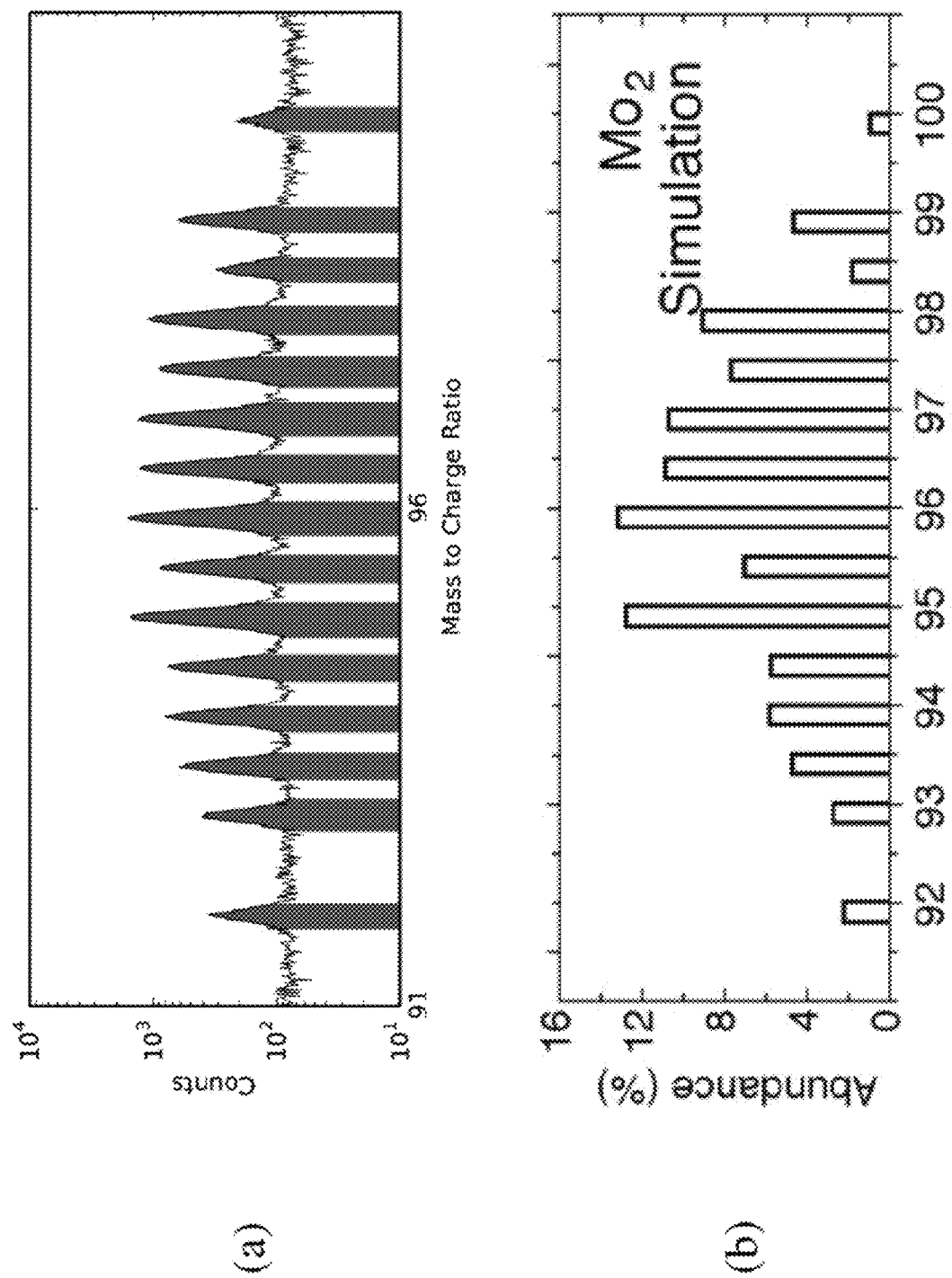
FIG. 28 shows mass-to-charge spectra of Mo$_2^{2+}$ diatomic clusters from (a) experiment, according to one embodiment of the invention, and (b) simulated abundances [10].
Figure 29:
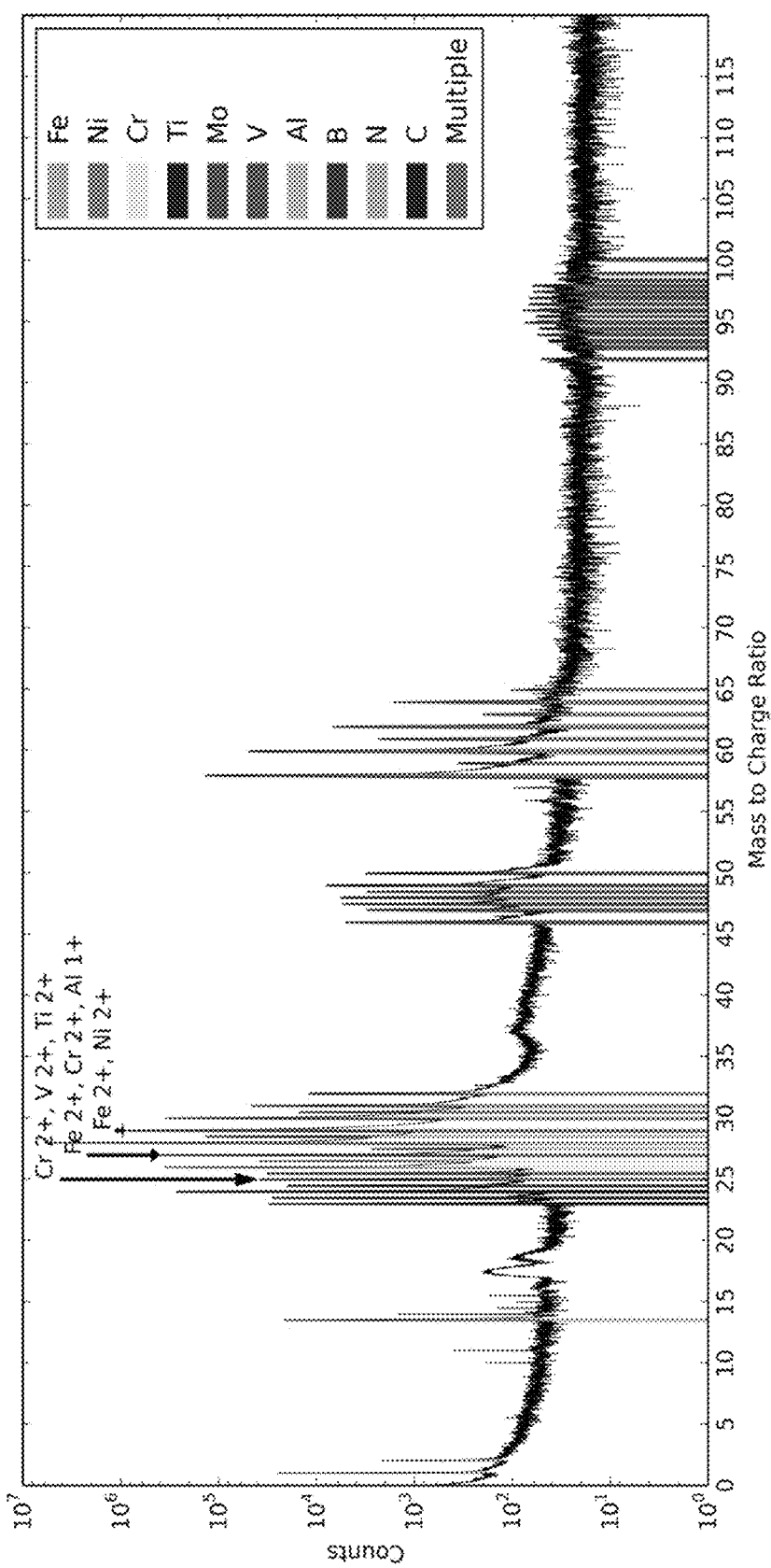
FIG. 29 shows mass-to-charge spectrum of TRIP-180 tempered at 700° C. for 2.5 hr at a lower pulsed laser energy, according to one embodiment of the invention.

As seen in FIG. 26 and scaled to view in FIG. 27(a), there exist multiple Mo peaks in the range of 92 to 100 mass-to-charge ratio. These are seen to be doubly charged diatomic Mo cluster ions, $Mo_2^{2+}$. Diatomic clusters are rarely formed by metal ions in LEAP experiments as they are unstable due to the strong repulsive Coulomb forces. Isheim et al. showed the existence of these by comparing spectra to simulations of the fifteen different cluster masses possible [10]. The results of these simulations are compared to the $Mo_2^{2+}$ clusters observed in the LEAP reconstructions in FIG. 28. It is seen that at lower laser energies, the abundance of the $Mo_2^{2+}$, as well as several other singly charged ion peaks between 45 and 65 mass-to-charge ratio, decreases as shown in FIG. 29. As the $Mo_2^{2+}$ clusters contain two Mo ions, the counts in these peaks must be doubled to accurately reflect composition.

Figure 25:
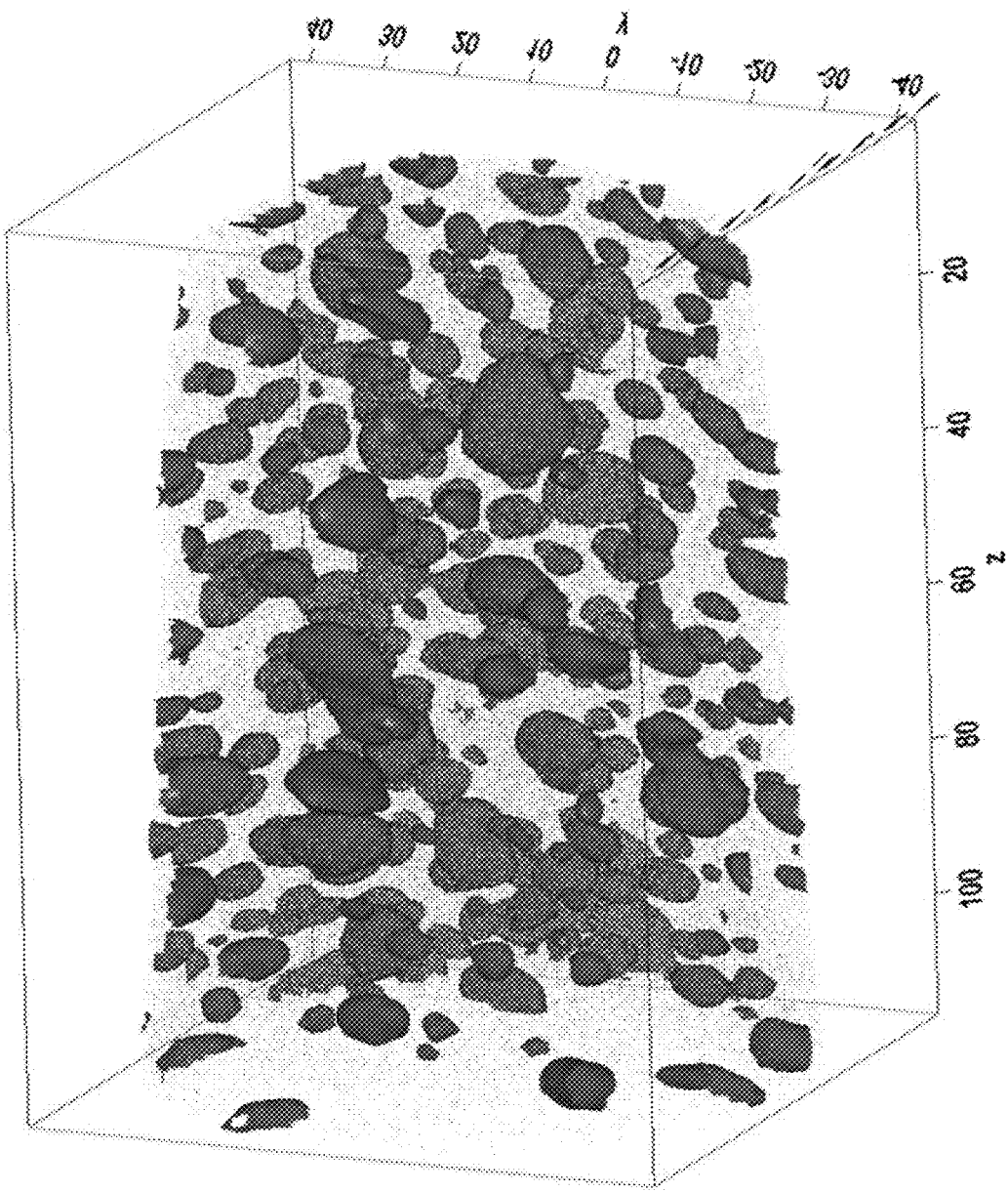
FIG. 25 shows LEAP reconstruction of TRIP-180 tempered at 700° C. for 1 hr. The γ' boundaries are shown by the purple surface and orange dots are iron atoms, according to one embodiment of the invention.
Figure 30:
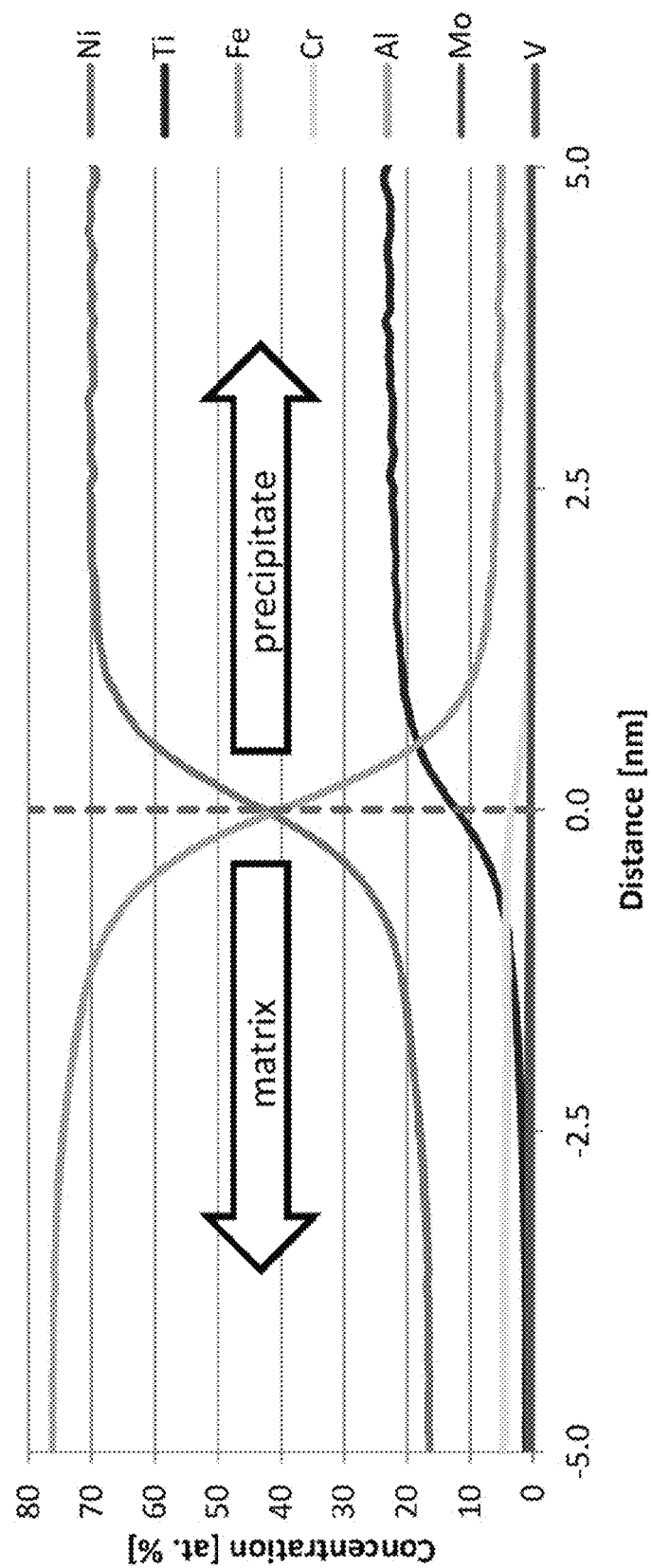
FIG. 30 shows proximity histogram of TRIP-180 tempered at 700° C. for 8 hr.
Figure 31:
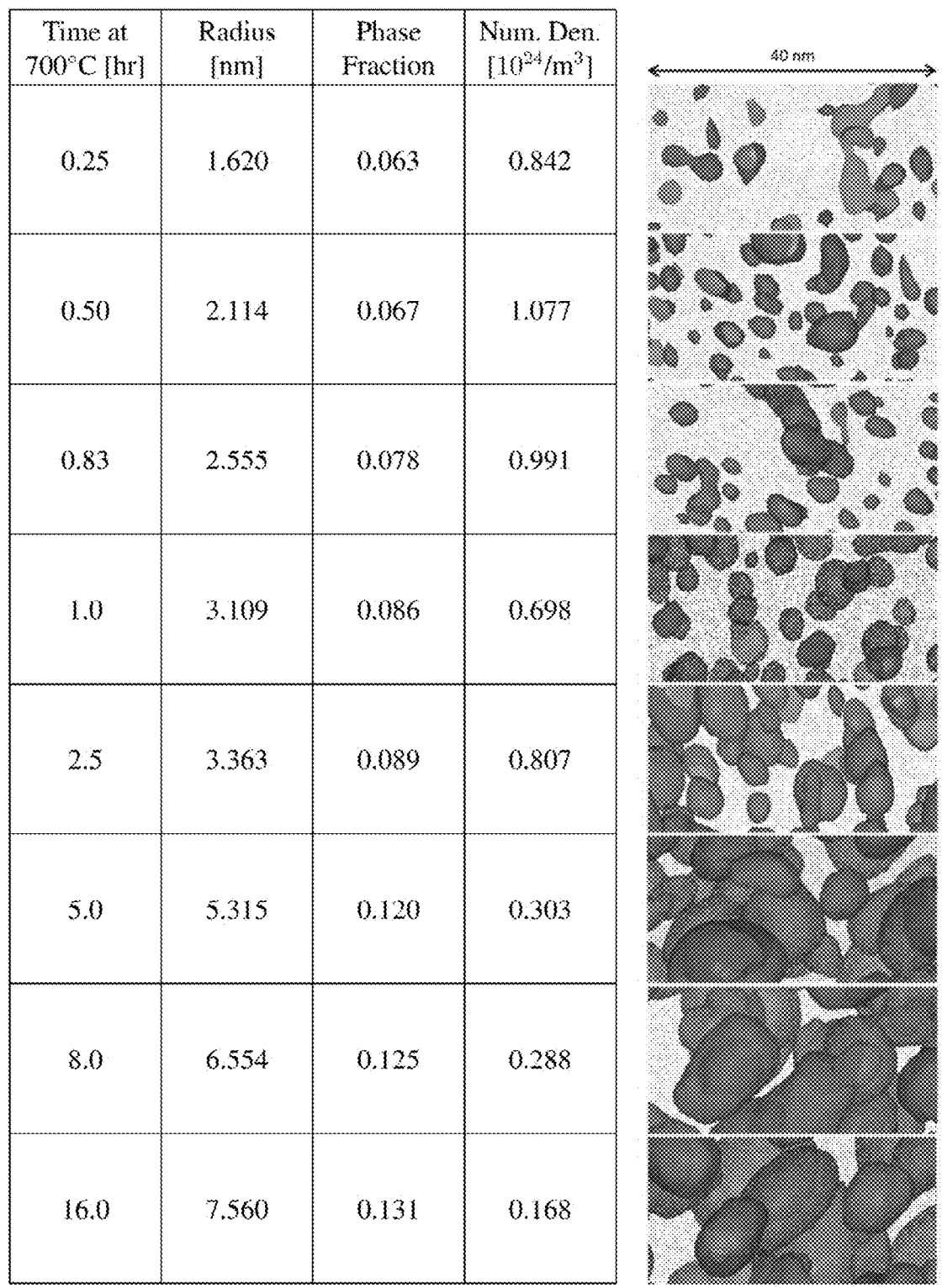
FIG. 31 shows LEAP γ' precipitate analysis results, according to one embodiment of the invention.

Once the overlapping peaks and $Mo_2^{2+}$ clusters were accounted for, a 45 at. % nickel isoconcentration surface was created in each reconstruction as seen in FIG. 25. Following this, proximity histograms across all interfaces were created as seen in FIG. 30, where the interface is defined at the inflection of the nickel and iron curves as these most distinctly partition to the γ' precipitates and austenite matrix, respectively. The radii, volume fractions, and number densities of the γ' precipitates in each sample were calculated. The results are tabulated in Table 5 and an image from each reconstruction is shown in FIG. 31 as it matches with the line of the table. The 0.125 hr tempered sample is not shown as no precipitates were found, and only slight fluctuations in composition were detected.

1.4.2 Calculation of Associated γ' Precipitation Constants

Figure 32:
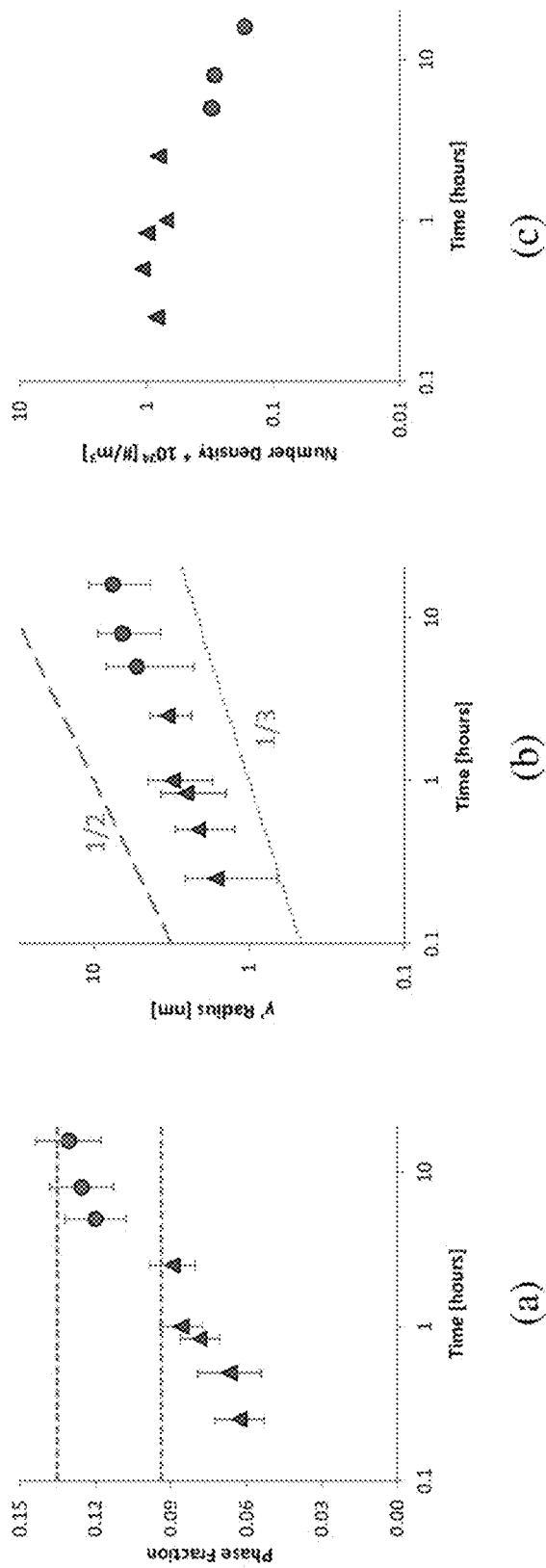
FIG. 32 shows (a) phase fraction, (b) γ' radius, and (c) number density versus tempering time at 700° C. in hours indicating points where the γ' is coherent with the matrix, blue triangles, and incoherent, red circles, according to one embodiment of the invention.

The results shown in Table 5 are plotted in FIG. 32.

TABLE 5

LEAP γ' precipitate analysis results.

| Time at 700° C. (hr) | Radius (nm) | Phase Fraction | Num. Den. ($10^{24}/m^3$) |
|---|---|---|---|
| 0.25 | 1.620 | 0.063 | 0.842 |
| 0.50 | 2.114 | 0.067 | 1.077 |
| 0.83 | 2.555 | 0.078 | 0.991 |
| 1.0 | 3.109 | 0.086 | 0.698 |
| 2.5 | 3.363 | 0.089 | 0.807 |
| 5.0 | 5.315 | 0.120 | 0.303 |
| 8.0 | 6.554 | 0.125 | 0.288 |
| 16.0 | 7.560 | 0.131 | 0.168 |

Figure 33:
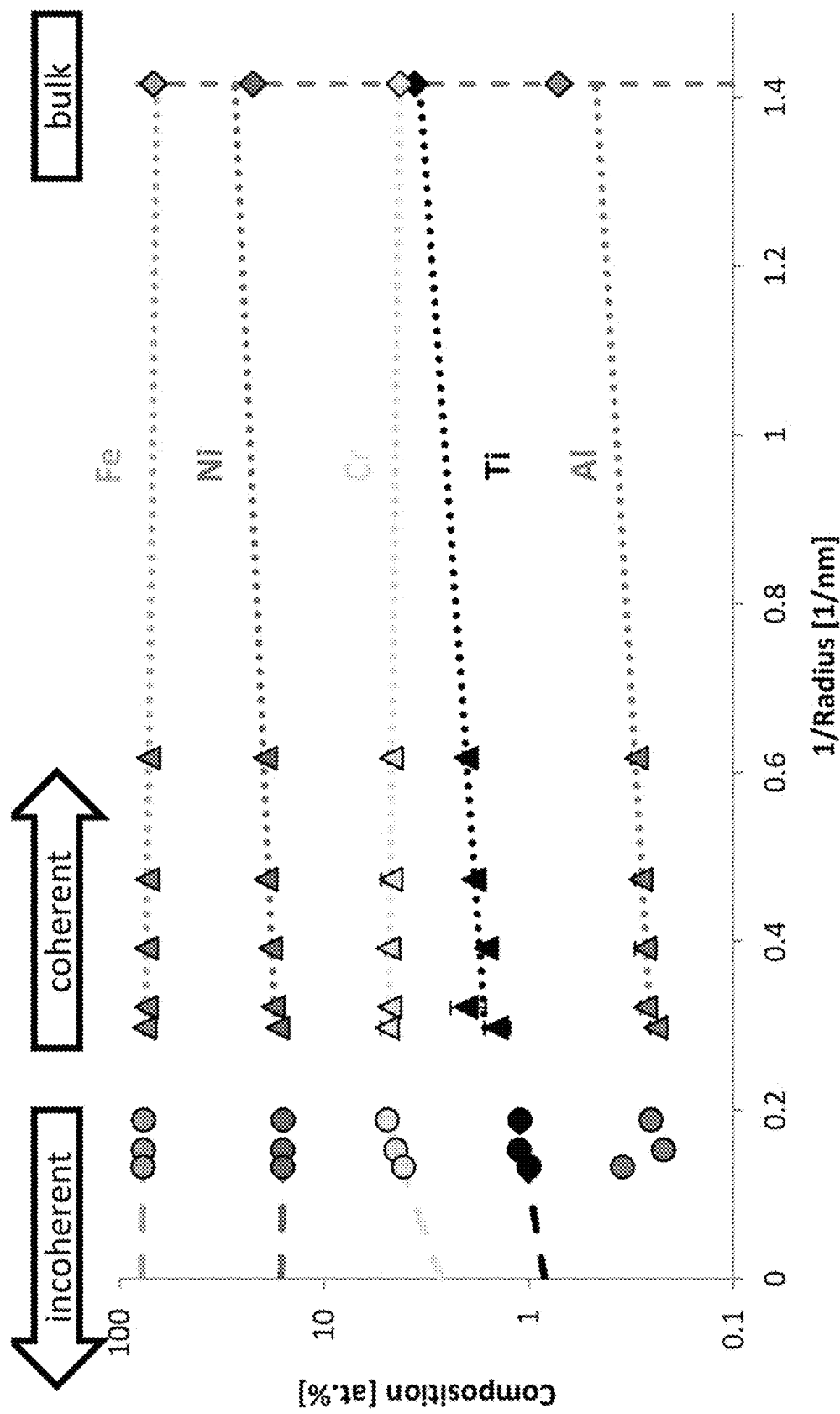
FIG. 33 shows a Gibbs-Thomson plot of the austenite matrix and bulk composition showing the transition from coherent to incoherent by a change in slope from right to left, according to one embodiment of the invention.
Figure 34:
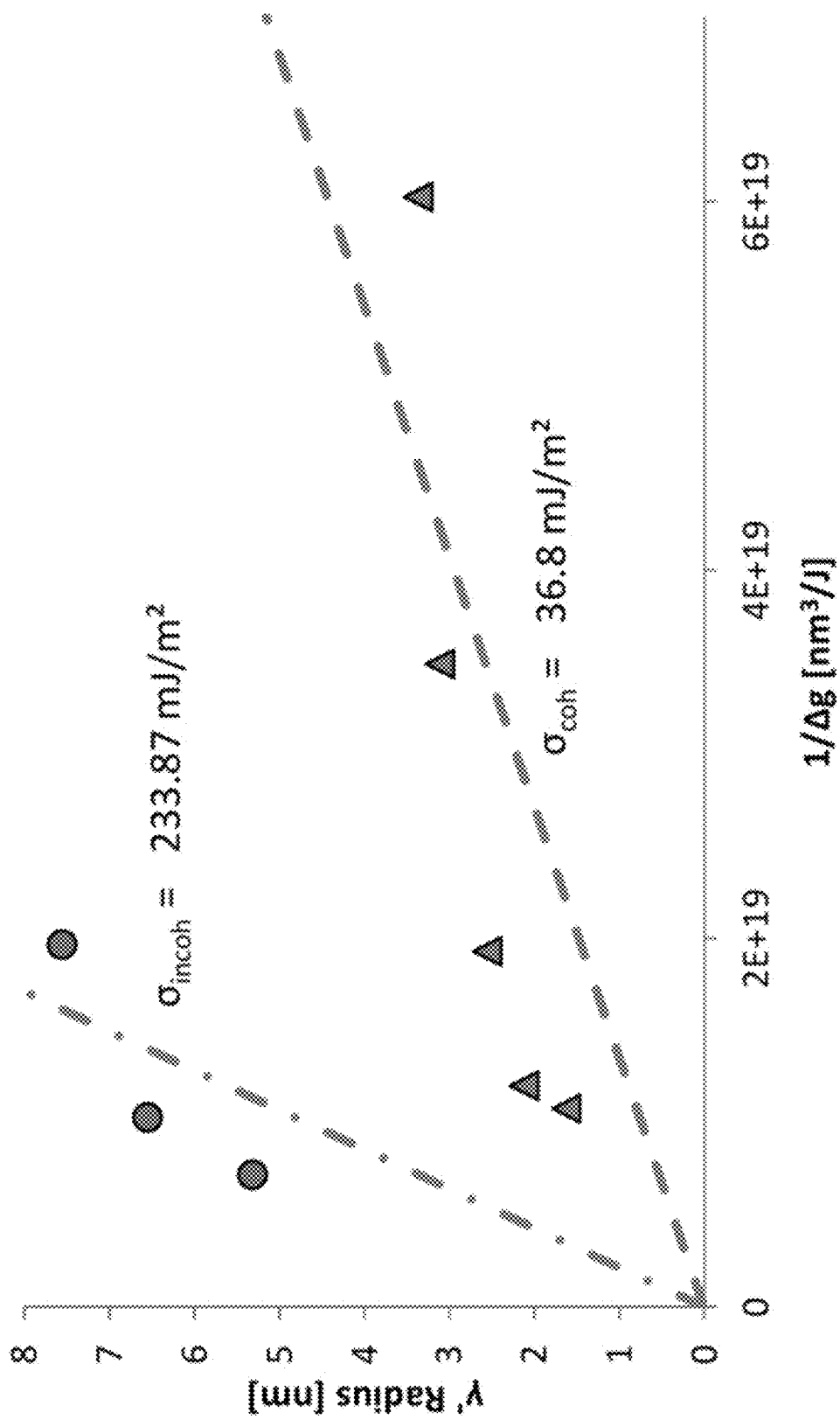
FIG. 34 shows γ' radius versus the inverse of volumetric capillary energy, 1/Δg, according to one embodiment of the invention. The slope is twice the interfacial energy.

The evolution of the radius in FIG. 32(b) indicates that the matrix is highly supersaturated and the evolution of the γ' radius is controlled by coarsening either directly from nucleation or with a very short growth regime in between. On a log-log plot, a slope of ½ indicates growth, a slope of ⅓ indicates coarsening, and smaller slopes indicated a transient region between growth and coarsening. The decreasing trend in number density, shown in FIG. 32(c), also confirms that the γ' quickly begins coarsening. In FIG. 32(a), the evolution of the phase fraction is displayed. The phase fraction is seen to approach an equilibrium value at 2.5 hours of tempering, shown as the blue dashed line. After this point, the γ' precipitates grow larger than a critical radius and lose coherency with the austenite matrix. This results in an abrupt jump in the phase fraction and it approaches a new equilibrium, shown as the red dashed line. This higher equilibrium, the incoherent equilibrium, is the true equilibrium phase fraction of γ' while the previous is a coherent equilibrium. The coherency transition is exemplified by the change in slope of composition versus inverse radii curves of the Gibbs-Thomson plot in FIG. 33. On the Gibbs-Thomson plot, the y-intercepts model the matrix composition (a similar plot can be constructed for the precipitate) when the γ' radius is infinite. This provides the equilibrium solubilities of all components of the matrix and precipitate and can be calculated from both the intercepts of the incoherent and coherent lines. By extending the coherent best fit lines back to the bulk composition, a critical radius for nucleation can be determined. This is shown graphically in FIG. 33 at a radius of 0.71 nm (1.42 nm). Combining this with the multi-dimensional lever rule, the equilibrium phase fractions are calculated to be 0.094 and 0.135 for coherent and incoherent equilibrium, respectively. These are shown as the dashed lines in FIG. 32(a). Once the equilibrium phase fractions are calculated, Thermo-Calc is used to calculate the energy needed to be added to the γ' phase to achieve the phase fraction. For coherent equilibrium, an addition of 507 J/mol is needed, while for incoherent equilibrium, an addition of −1456 J/mol is needed. Therefore a general correction to the database of −1456 J/mol for the γ' phase is needed as the equilibrium phase fraction originally calculated by Thermo-Calc is too low, and the coherent strain energy, $E^{st}$, added for coherent equilibrium is the difference of those values, 1963 J/mol. From that, volumetric capillary energies, 1/Δg, for each data point can be calculated by taking the molar capillary energy added to Thermo-Calc to achieve the desired phase fraction, adjusting with the appropriate energy shift as just mentioned, and dividing it by the molar volume, $V_m$. The radius can be plotted versus the inverse volumetric capillary energy, as in FIG. 34, to calculate the coherent and incoherent interfacial energies, $\sigma_{coh}$ and $\sigma_{incoh}$. The slope of the resulting best fit line is twice the interfacial energy, yielding a value of 36.80 mJ/m² and 233.87 mJ/m² for the coherent and incoherent interfacial energies, respectively.

To define the critical radius, $r_{crit}$, at which coherency transition occurs, the free energies of the coherent and incoherent precipitates must be analyzed. Coherent precipitates have a lower interfacial energy accompanied with a strain energy from the lattice misfit with the matrix. Eshelby performed a quantitative assessment of the elastic strain energy and determined that the free energy of a spherical, coherent precipitate, $\Delta G_{coh}$, was the sum of a volumetric strain energy and chemical interfacial energy term [7].

$$\Delta G_{coh} = 4\mu\delta^2 \cdot \tfrac{4}{3}\pi r^3 + 4\pi r^2 \sigma_{coh} \quad (5)$$

where μ is the matrix shear modulus and δ is the unconstrained misfit, calculated as the difference between the molar volumes, $V_m$, of the austenite and γ' phases. After surpassing the critical radius, an incoherent interface relieves the coherent strain energy but adds a structural contribution to the interfacial energy and gives the free energy of a spherical, incoherent precipitate, $\Delta G_{incoh}$, as a chemical interfacial energy term.

$$\Delta G_{incoh} = 4\pi r^2 \pi r^2 \sigma_{incoh} \quad (6)$$

By setting Equations (5) and (6) equal to each other, a critical radius can be solved for where the free energies of coherent and incoherent precipitates are equal [4].

$$r_{crit} = \frac{3(\sigma_{incoh} - \sigma_{coh})}{4\mu\delta^2} \quad (7)$$

Solving for Equation (7), $r_{crit}$ is found to be 3.47 nm by using a calculated δ of 2.36% using the TCNI8 database in Thermo-Calc where the $V_m$ of the austenite and γ' phases are 7.225379*10⁻⁶ m³/mol and 7.4002985*10⁻⁶ m³/mol. The TCNI8 database is very similar to Ni-Data 7, but it includes lattice parameter data as Ni-Data 7 does not. The results of this analysis are given in Table 6.

TABLE 6

Results of γ' precipitation analysis. $r_{crit}$ is solved as 3.47 nm.

| Precipitate Type | Equilibrium Phase Fraction | Coherent Strain Energy (J/mol) | Energy Added in Thermo-Calc (J/mol) | Interfacial Energy (mJ/m²) |
|---|---|---|---|---|
| Coherent | 0.094 | 1963 | 507 | 36.80 |
| Incoherent | 0.135 | — | −1456 | 233.87 |

1.5 $M_s^\sigma$(u.t.) Testing

Austenite stability of TRIP steels, both fully austenitic and those dual or multi phase steels with retained austenite, is quantified by the $M_s^\sigma$ temperature. The $M_s^\sigma$ temperature is different because the transformation stress depends on the loading conditions and can be more specifically $M_s^\sigma$(u.t.), $M_s^\sigma$(sh), and $M_s^\sigma$(c.t.) temperatures for uniform tension, shear, and crack tip, respectively. This disclosure focuses on $M_s^\sigma$(sh), with the measurement of the $M_s^\sigma$(u.t.) temperature to calibrate stability. Generally, the $M_s^\sigma$(sh) temperature is approximately 20° C. less than the $M_s^\sigma$(u.t.) temperature based on the ΔG, term. The austenite stability is most affected by the fraction of nickel and chromium remaining in solution after precipitation of the γ'. Given the composition of the γ' phase, nominally $Ni_3(Ti,Al)$, where nickel is primarily on the first sublattice, substituting with iron, and titanium and aluminum on the second sublattice, the nickel content in the matrix is dependent on the precipitation of the γ' while all of the chromium in the alloy remains in the matrix.

Figure 35:
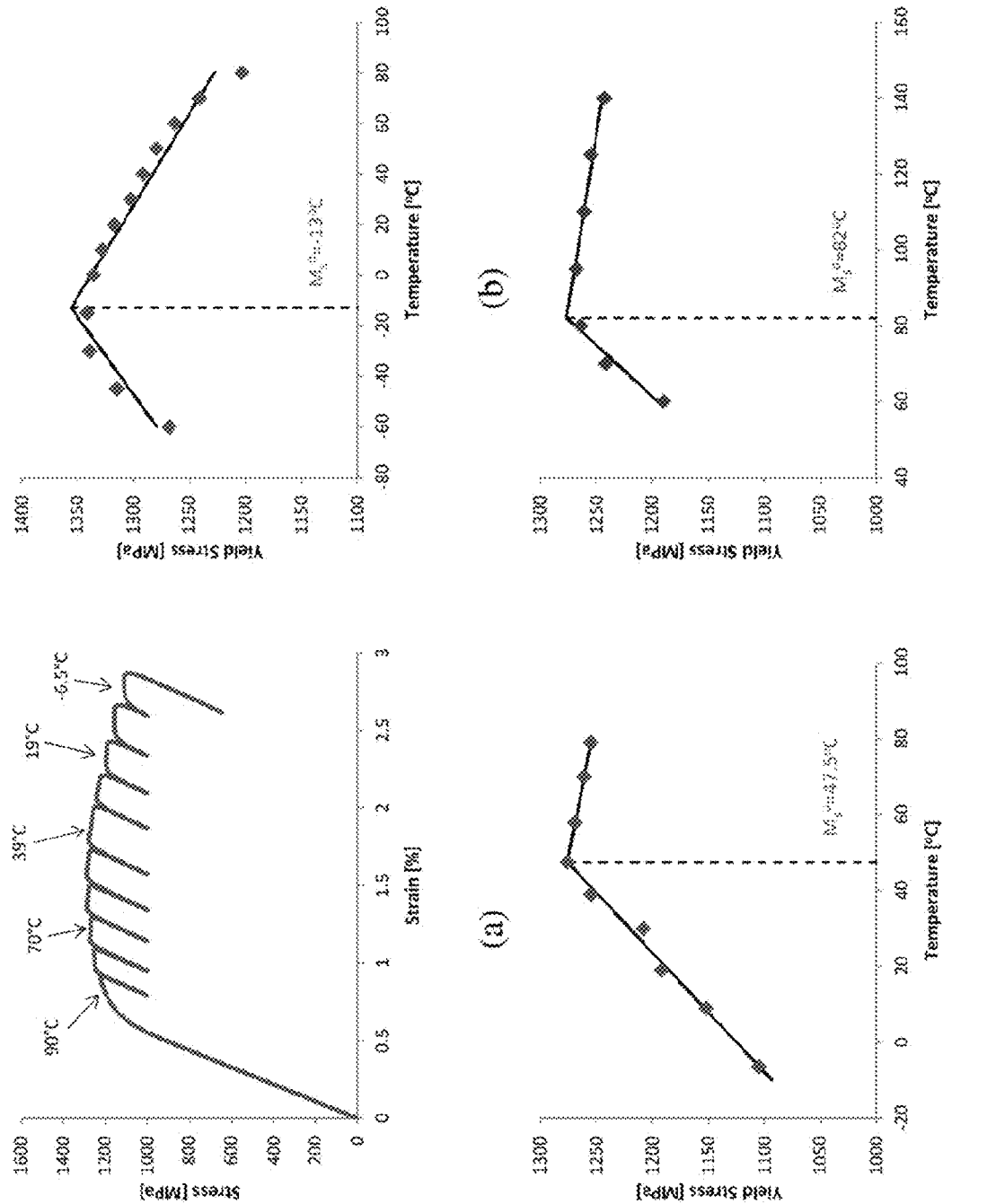
FIG. 35 shows (a) single specimen M$_s^\sigma$(u.t.) temperature test for TRIP-180 tempered at 700° C. for 5 hr and M$_s^\sigma$(u.t.) temperature measurements for TRIP-180 at 700° C. for (b) 1 hr, (c) 5 hr, according to one embodiment of the invention, and (d) 16.5 hr [8].

Experimental data for $M_s^\sigma$(u.t.) temperature tests was gathered from Feinberg in his work on this project [8] and in collaboration with Fraley in his work on analysis of TRIP steels in passive damping applications. Three separate tests were performed on TRIP-180 samples tempered at 700° C. for 1 hr, 5 hr, and 16.5 hr. FIG. 35 shows an example of a multiple cycle, single specimen $M_s^\sigma$(u.t.) temperature test in FIG. 35(*a*) and the yield points plotted versus temperature showing the $M_s^\sigma$(u.t.) temperature for the three tempering conditions in FIGS. 35(*b*)-35(*d*) [8]. The measured $M_s^\sigma$(u.t.) temperatures are −13° C., 47.5° C., and 82° C. for the 1 hr, 5 hr, and 16.5 hr tempered sample, respectively.

To calibrate the $M_s^\sigma$ model for the TRIP-180 composition space, the eight experimental LEAP points were simulated in Thermo-Calc calculations where the precipitate radius is related to volumetric capillary energy through a Gibbs-Thomson effect in Equation (8).

$$\Delta g = \frac{2\sigma}{r} \quad (8)$$

With the Thermo-Calc output at each given radius and phase fraction, the chemical driving force for the martensitic transformation, $\Delta G_{ch}$, of matrix composition is calculated in Thermo-Calc. Also using the matrix compositions, the frictional work term, $W_f^{sol}$, and mechanical driving force term, $\Delta G_\sigma$, are calculated as a function of temperature. Solving the Olson-Cohen model, reproduced below in Equation (9), by incorporating the three measured $M_s^\sigma$(u.t.) temperatures and the calculated $\Delta G_{ch}$, $\Delta G_\sigma$, and $W_f^{sol}$ terms allows for determination of the $g_n$ term.

$$\Delta G_{ch} + \Delta G_\sigma = -G_n - W_f^{sol}$$

when σ=$\sigma_y$ and T=$M_s^\sigma$ (9)

Figure 36:
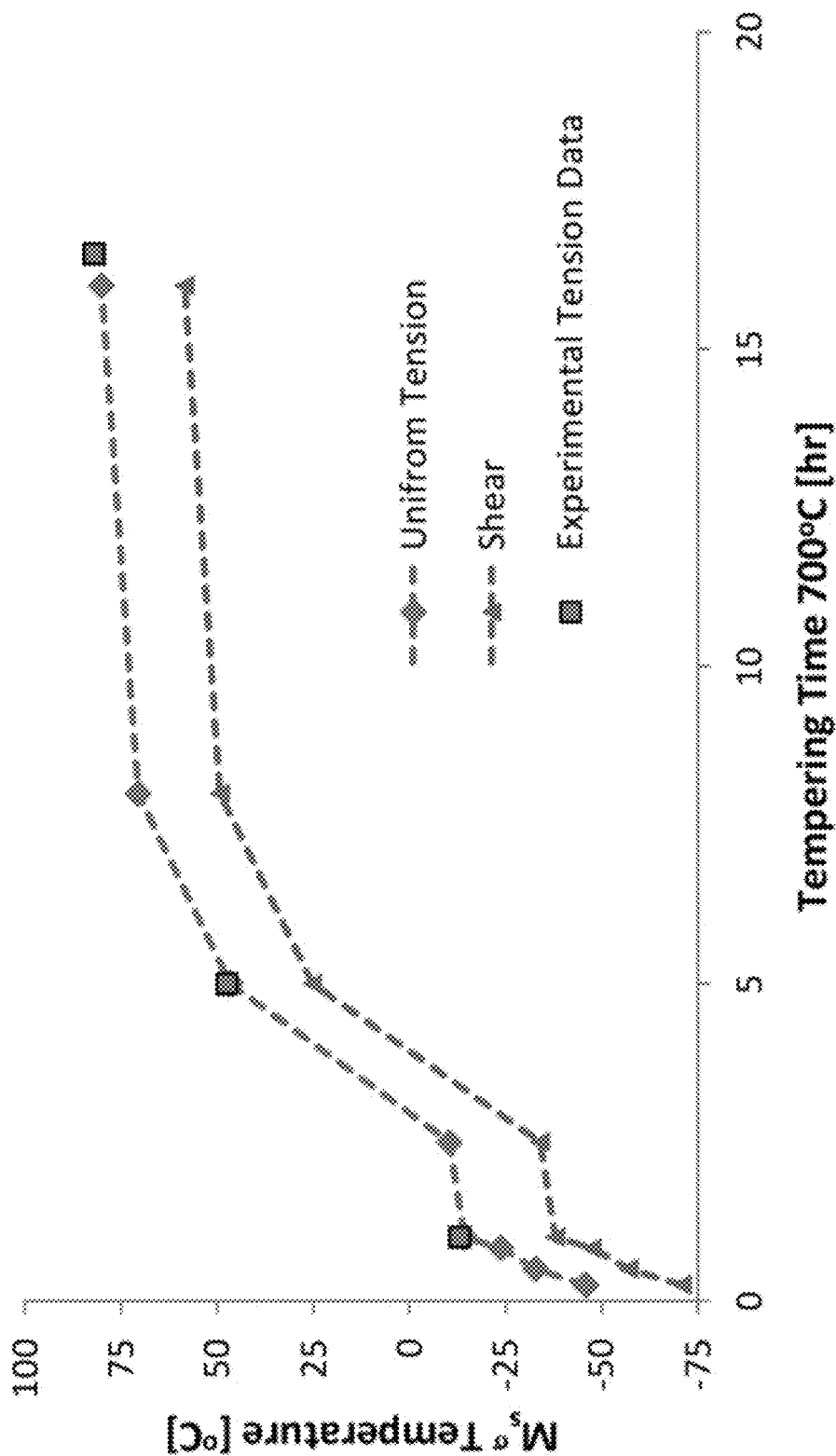
FIG. 36 shows M$_s^\sigma$ temperature model fitting modeled temperatures from experimental LEAP data to experimentally measured M$_s^\sigma$(u.t) temperatures to calculate G$_n$, according to one embodiment of the invention.

$G_n$ is solved to be 837.5 J/mol. With this calibrated $G_n$ term, the Olson-Cohen model can be used to predict the $M_s^\sigma$(u.t.) and $M_s^\sigma$(sh) temperatures. The result of these predictions is shown in FIG. 36 where the measured $M_s^\sigma$(u.t.) temperatures, blue squares with black outlines, show excellent agreement with the predicted $M_s^\sigma$(u.t.) temperatures from the experimental LEAP data, blue diamonds.

1.6 PrecipiCalc Modeling

Figure 37:
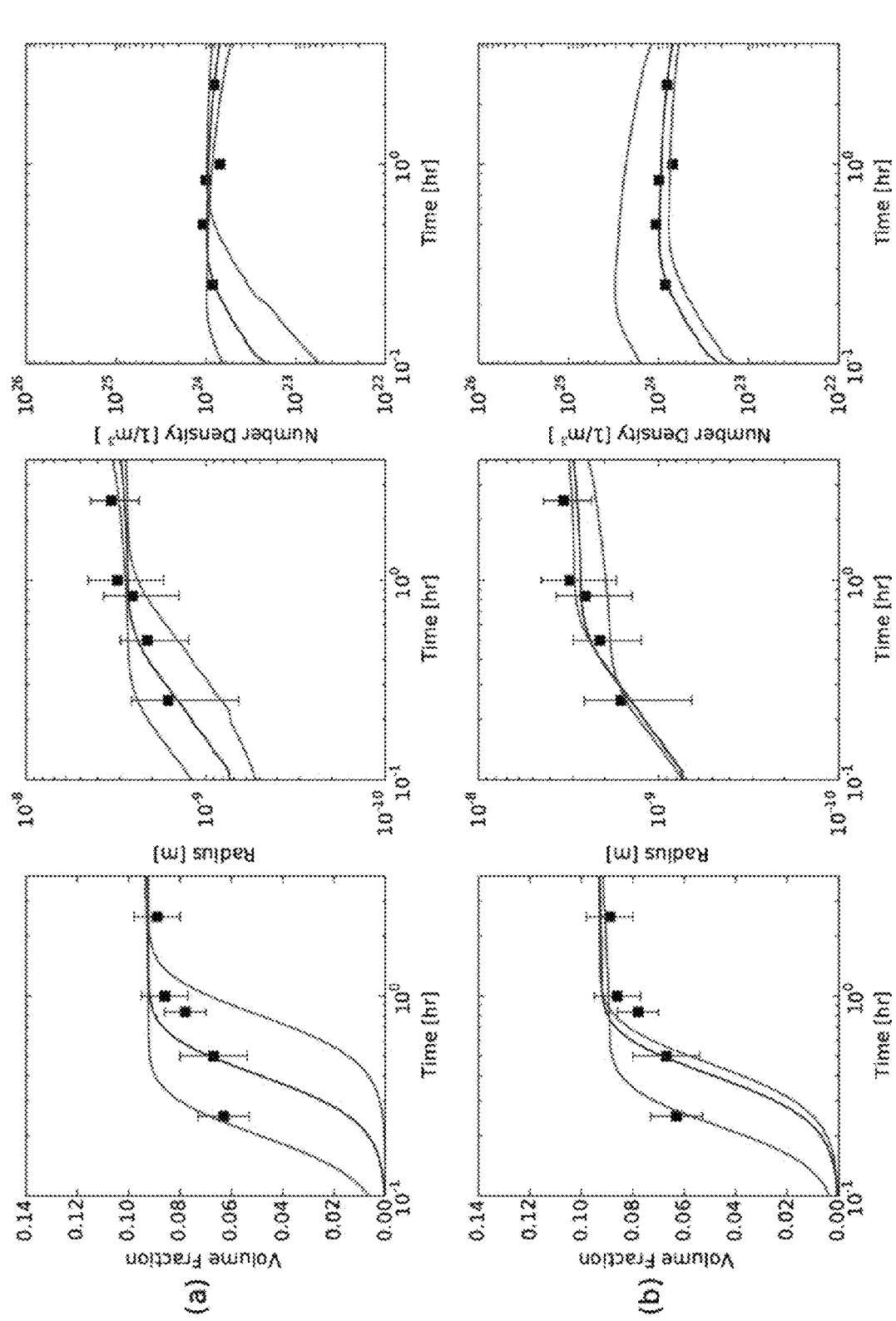
FIG. 37 shows several PrecipiCalc simulations for the evolution of coherent γ' precipitates in TRIP-180 with (a) varied diffusivity factors, and (b) varied number of nucleation sites, according to one embodiment of the invention.

To calibrate the precipitation kinetics of the γ' in TRIP-180, the coherent and incoherent interfacial energies and Thermo-Calc added energies from Table 6 are incorporated into the precipitation framework within the PrecipiCalc software. From this, the default values adding the time dependency to the precipitation are varied in an effort to match the simulation to the experimentally determined γ' values as given in Table 5. To successfully match the simulation to experimental results, the coherency transition at the $r_{crit}$ of 3.47 nm as discussed in Section 1.4.2 must be accounted for. PrecipiCalc does not directly have the ability to simulate a coherency transition, so the simulation is therefore initially run using coherent precipitation values. At the $r_{crit}$, the simulation is halted and a particle size distribution (PSD) file is generated. The PSD file is then loaded into a second simulation with the incoherent precipitation values. This allows for calibration of the coherent and incoherent simulations separately. FIG. 37 shows select simulations run to calibrate the coherent simulations. The diffusivity matrix scaling factor with, DIFF_FAC1, and without, DIFF_FAC2, linear temperature dependency can be varied up to about a factor of three to scale the entire diffusivity matrix from the mobility database, $D_{ij}$, via Equation (10). As tempering temperature is not changed, only DIFF_FAC1 is calibrated where values 0.5, green line, 1.0, blue line, and 2.0, red line are seen in FIG. 37(a). As the diffusivity scaling factor increases, the radius and volume fraction increase with time and the number density peaks earlier.

$$D_{ij}^{new} = (|DIFF_FAC1| + |DIFF_FAC2|*T)*D_{ij}^{org} \quad (10)$$

In addition to adjusting the diffusivity factor, the number of nucleation sites for the precipitate phase can be varied. The value, P_NUC_HOM_NUM_SITES can take the value of zero, where $N_a/V_m$ is used for the number of sites, or any positive value. More nucleation sites increases the volume fraction and number density and speeds up the transition from growth to coarsening in radius evolution. The number of nucleation sites affects the steady state nucleation rate, $J_{ss}$, as shown in Equation (11) where P_NUC_HOM_NUM_SITES replaces $N_a/V_m$ if it is a positive value. FIG. 37(b) shows the change in P_NUC_HOM_NUM_SITES where the green line is $1*10^{24}$, the blue line is $1.5*10^{24}$, and the red line is $1*10^{25}$ number of nucleation sites.

$$J_{ss} = Z\beta^* \frac{N_a}{V_m} \exp\left(\frac{-W_R^*}{k_b T}\right) \quad (11)$$

Figure 38:
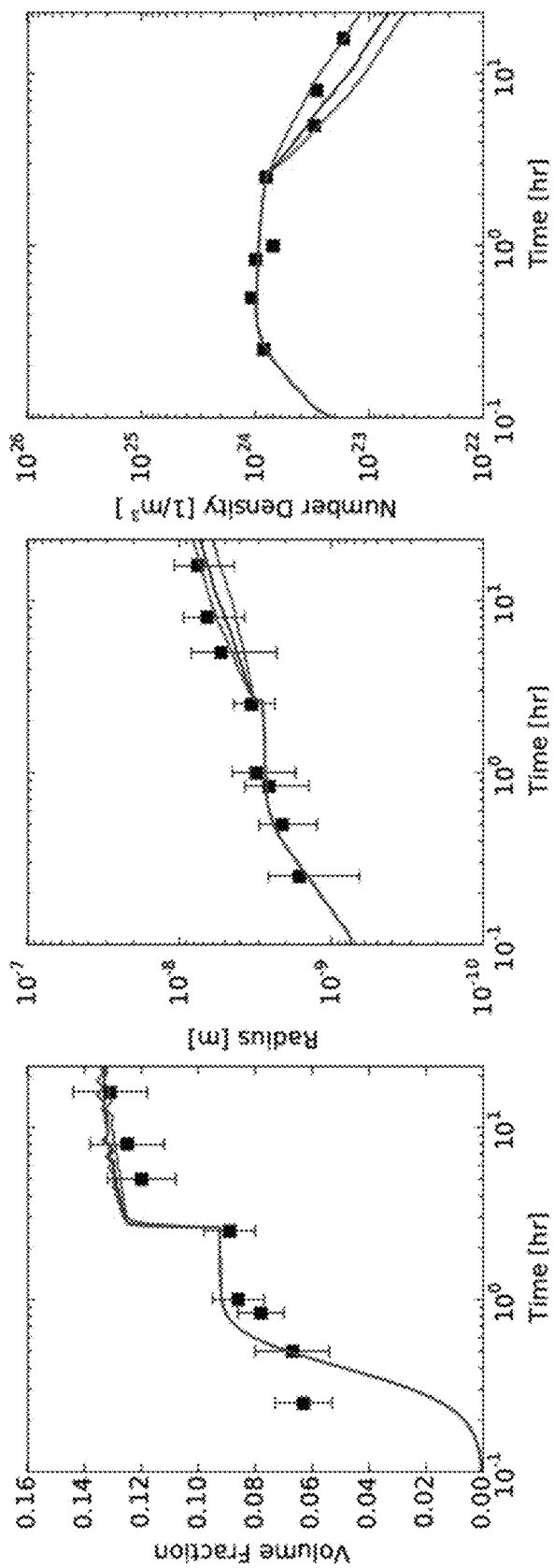
FIG. 38 shows several PrecipiCalc simulations for the evolution of incoherent γ' precipitates in TRIP-180 with varied diffusivity factors, according to one embodiment of the invention.
Figure 39:
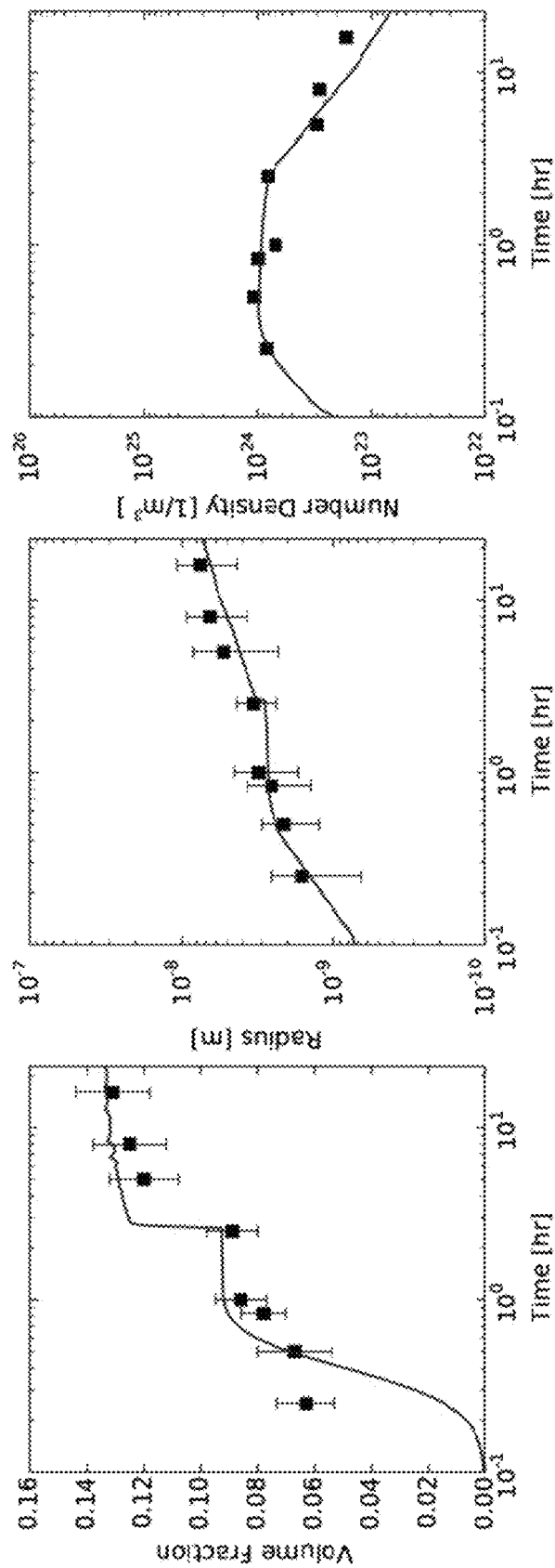
FIG. 39 shows a calibrated PrecipiCalc simulation for the evolution of γ' precipitates in TRIP-180, according to one embodiment of the invention.

The calibrated values for DIFF_FAC1 and P_NUC_HOM_NUM_SITES for the coherent simulation are 1.0 and $1.5*10^{24}$, respectively. To calibrate the incoherent simulation, the PSD output from the calibrated coherent simulation is used. As the particles have already nucleated and are entering the coarsening regime, only the diffusivity scaling factor was calibrated. Shown in FIG. 38, the values of DIFF_FAC1 for the green, blue, and red lines are 1.0, 2.0, and 3.0. The calibrated value for the incoherent simulation is 2.0. These values, for both the coherent and incoherent simulations are found in Table 7 and the calibrated simulation, with both the coherent, and the following incoherent simulation are shown in FIG. 39.

TABLE 7

Values used for calibration of the PrecipiCalc simulations for TRIP-180.

| Precipitation Type | DIFF_FAC1 | P_NUC_HOM_NUM_SITES |
|---|---|---|
| Coherent | 1.0 | $1.5*10^{24}$ |
| Incoherent | 2.0 | — |

2 Blastalloy TRIP 130 Design

The following description details the parametric computational design of Blastalloy TRIP 130. The property objectives detailed in Section 2.1 are based off of the objectives of TRIP-180 and the knowledge gained through the experimental work of Section 1 to further bolster performance against fragment penetration. Section 2.2 overviews the process in which Blastalloy TRIP 130 was designed. Section 2.3 details the thermodynamic approach to eliminating the η cellular precipitation without adding a warm working processing step. Sections 2.4, 3.5, and 2.6 explore the goals and process to meet them through the design. To conclude, Sections 2.7 and 2.8 detail the final design composition, properties, and precipitation simulation of Blastalloy TRIP 130 which allow for strength and austenite precipitation predictions versus tempering time.

2.1 Property Objectives

Building upon the experimental knowledge, computational predictions, and empirical data from various alloys including the designs of EX-425, BA-160, and TRIP-180, the property objectives of Blastalloy TRIP 130 are detailed in Table 8. The focus on preventing the plugging phenomenon by extending shear localization resistance is evidenced by reducing the strength goal to 896 MPa (130 ksi), setting the austenite stability to a $M_s^\sigma$(sh) of −40° C., increasing the shear instability resistance to 75%, and adding a FSP ballistic limit objective.

TABLE 8

Property objectives for Blastalloy TRIP 130.

| Primary Objectives | Secondary Objectives |
|---|---|
| Yield Strength: MPa (130 ksi) | Nonmagnetic: $T_{curie} < 0°$ C. |
| Optimized Austenite Stability: $M_s^\sigma$ (sh) = −40° C. | Weldable |
| FSP Ballistic Limit: $V_{50} > 1.2*V_{50}^{baseline}$ | Corrosion Resistant |
| Shear Instability Resistance: $\eta_i^a > 75\%$ | Hydrogen Resistant: $K_{ISCC}/K_{IC} > 0.5$ |
| Uniform Tensile Ductility: $\varepsilon_u > 30\%$ | Fatigue Cracking Resistant |
| Sufficient Fracture Toughness: $K_{IC} \geq 90$ MPa/m$^{0.5}$ | Limited Cost |

The austenite stability was determined to be a $M_s^\sigma$(sh) temperature of approximately 60° C. below the use temperature, which is taken to be room temperature, as detailed through the HAT-type tests and FSP $V_{50}$ ballistic tests in Sections 1.2 and 1.3. This changes from the design of TRIP-180 where the $M_s^\sigma$(u.t.) was designed to be 5° C. The yield strength goal was determined to be 896 MPa (130 ksi) as this is the strength level of the QLT 10 wt. % Ni steel developed by Zhang which shows exceptional ballistic performance at that strength level [25]. Blastalloy TRIP 130 is designed to have superior ballistic performance without sacrificing any strength. This strength level is an increase from the 827 MPa (120 ksi) designed yield strength of TRIP-180, but lower than the 1241 MPa (180 ksi) realized yield strength of that alloy [8]. In addition, to save on processing costs, the warm working step was removed and therefore the elimination of the η phase must be achieved with compositional changes or standard heat treating processes.

2.2 Design Approach

With quantified and defined property objectives, the composition of Blastalloy TRIP 130 must be designed to meet these objectives in order to deliver the desired performance.

The austenite stability is controlled to ensure the minimum values for shear instability strain and uniform tensile resistance. The yield strength objective is achieved by the γ' precipitation. This lower strength and optimized austenite stability provide the maximum FSP ballistic limit achievable by exploiting the transformation hardening of the TRIP effect. To reduce the processing costs, the η grain boundary cellular precipitation is designed to be thermodynamically eliminated. The new design composition starts with the composition of TRIP-180 [8].

To begin the design process, the interrelation between the processing, structure, properties, and performance need to be understood in order to attack this design with a systems approach as discussed in Section 1.3. The design of Blastalloy TRIP 130 is mapped out in a systems design chart which visually represents the connections and interrelations between all the subsystems as seen in FIG. 40.

With the systems design chart in mind, a methodology for the parametric computational design was developed in order to achieve the strength goal, austenite stability goal, and the thermodynamic suppression of the η grain boundary cellular reaction. This overview is mapped in FIG. 41. The three main areas of design concern, highlighted in red, define the design pathways. The first is the thermodynamic suppression of the η phase to prevent the grain boundary cellular precipitation. This step involves Thermo-Calc calculations of the driving forces for the γ' and η phases. The second, precipitation strengthening, builds off of the output from the thermodynamic calculations to provide a range of radii and volume fractions of γ' that satisfy the strengthening goal. The third and final design focus is the austenite stability, where the evolution of the matrix composition with the γ' precipitation is quantified, and constrained equilibrium calculations within Thermo-Calc are made possible. The first part of this analysis was covered in Section 1.4.2 and the results in Table 6 provide the values that enable calculation of the matrix composition. Finally, bulk compositions are examined to ensure that all three main requirements have been successfully achieved.

The first main area, the thermodynamic suppression of the η phase is discussed in Section 2.3, where a quantified thermodynamic goal is calculated and implemented. The second area, the strengthening goal, is explained in Sections 2.4 and 2.5, where updates to the strengthening model used in the design of TRIP-180 are discussed and the method of reaching the strength goal is detailed by incorporating constrained equilibrium Thermo-Calc calculations that associate radius and phase fraction. The third focus, achieving the austenite stability, is discussed while maintaining the thermodynamic suppression of the η phase and the γ' precipitation required to obtain the strength goal. The composition space that is explored for this design is based on the composition of TRIP-180 and has the same additions of chromium, vanadium, molybdenum, carbon, and boron. The nickel, aluminum, and titanium additions are varied to achieve these goals.

2.3 Thermodynamic Suppression of the η Phase

The first phase of the design process involves preventing the grain boundary cellular precipitation by thermodynamically suppressing the η phase. This not only improves strength and ductility, but it also reduces processing costs by removing the need for the warm working step. The challenge is to either provide a strong enough driving force for the precipitation of metastable γ' or move into a composition space where the γ' phase is the stable phase in equilibrium with the austenite γ phase.

To acquire an understanding of the thermodynamic stability of the γ' phase as compared to the η phase, a thermodynamic value expressing the increment in a driving force, ΔDF, is used where ΔDF is the difference between the driving force of the γ' phase and the η phase at the tempering temperature. Therefore, greater values of ΔDF indicate that the γ' phase is more thermodynamically stable. As a baseline, the ΔDF value is calculated for both TRIP-180 and for A-286, a commercially available, fully austenitic, γ' strengthened steel which exhibits no η phase. The composition of A-286 is given in Table 9.

TABLE 9

Composition of A-286.

| wt. % | Ni | Cr | Ti | Mn | Mo | V | Al | Si | C | B | Fe |
|---|---|---|---|---|---|---|---|---|---|---|---|
| min. | 24.0 | 13.5 | 1.90 | 0 | 1.0 | 0.1 | 0 | 0 | 0 | 0.001 | Bal. |
| max. | 27.0 | 16.0 | 2.35 | 2.0 | 1.5 | 0.5 | 0.35 | 1.0 | 0.08 | 0.010 | |

The ΔDF values for TRIP-180 and A-286 are −1107.33 J/mol and −830.43 J/mol as calculated in Thermo-Calc. As is seen, the η phase is thermodynamically more favorable in TRIP-180 than in A-286. These values also indicate that the γ' phase does not have to be the equilibrium precipitate phase during tempering which means that the γ' phase must be kinetically favored during normal heat treating conditions. To ensure the η phase is thermodynamically suppressed, Blastalloy TRIP-130 is designed to have a ΔDF of at least −415 J/mol.

Figure 42:
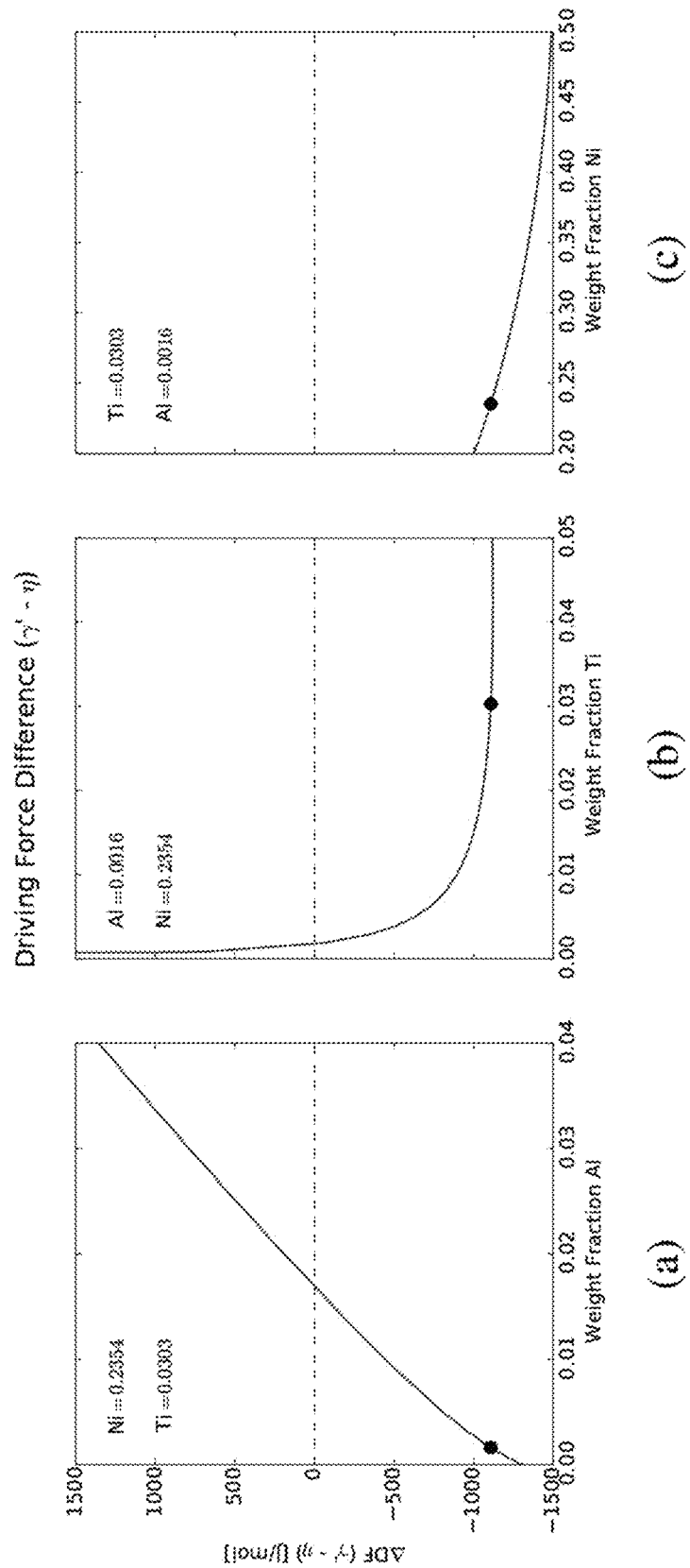
FIG. 42 shows ΔDF values versus weight fraction (a) aluminum, (b) titanium, and (c) nickel where the black dots indicate the ΔDF value and composition of TRIP-180, according to one embodiment of the invention.
Figure 43:
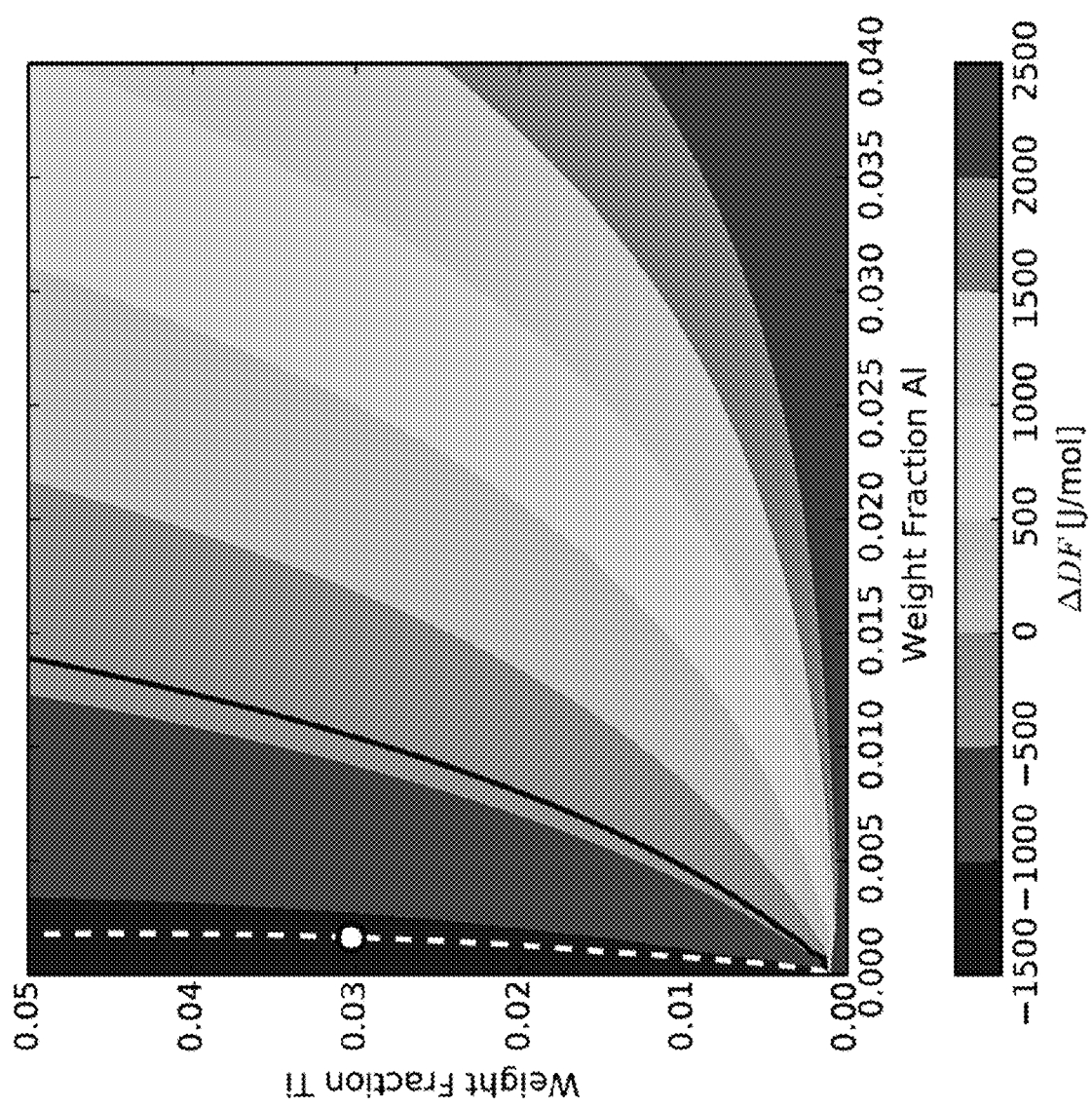
FIG. 43 shows ΔDF values versus weight fraction aluminum and titanium, according to one embodiment of the invention. The solid black line indicates the critical value of ΔDF of −415 J/mol and the white black line indicates the TRIP-180 ΔDF of −1107 J/mol with the composition indicated by the white dot.

To check the effect of changing the composition on the driving force difference, several Thermo-Calc calculations were performed and summarized in FIG. 42 for varying aluminum in FIG. 42(*a*), titanium in FIG. 42(*b*), and nickel in FIG. 42(*c*) relative to the levels in TRIP-180. As shown in FIG. 42, the driving force difference is changed most drastically by varying the weight fraction aluminum, and by increasing the aluminum, the γ' phase becomes much more thermodynamically stable than the η phase. The inverse is true with the additions of titanium and nickel. This follows given the compositions of γ' and η which are $Ni_3(Ti,Al)$ and $Ni_3Ti$, respectively. Greater additions of aluminum yield a larger driving force for aluminum to be on the second sublattice and thus precipitate γ' rather than η. As nickel content is primarily controlled to adjust austenite stability, aluminum and titanium are used to control the suppression of the η phase. FIG. 43 shows the combined effects of aluminum and titanium on the driving force difference. The black line indicates the critical ΔDF value of −415 J/mol where the composition space to the right of the line meets the condition set above based on the thermodynamics of A-286. Similar trends are seen in both FIGS. 42 and 43 where the addition of aluminum heavily affects the ΔDF and the effect of titanium decreases at higher weight fractions.

Figure 44:
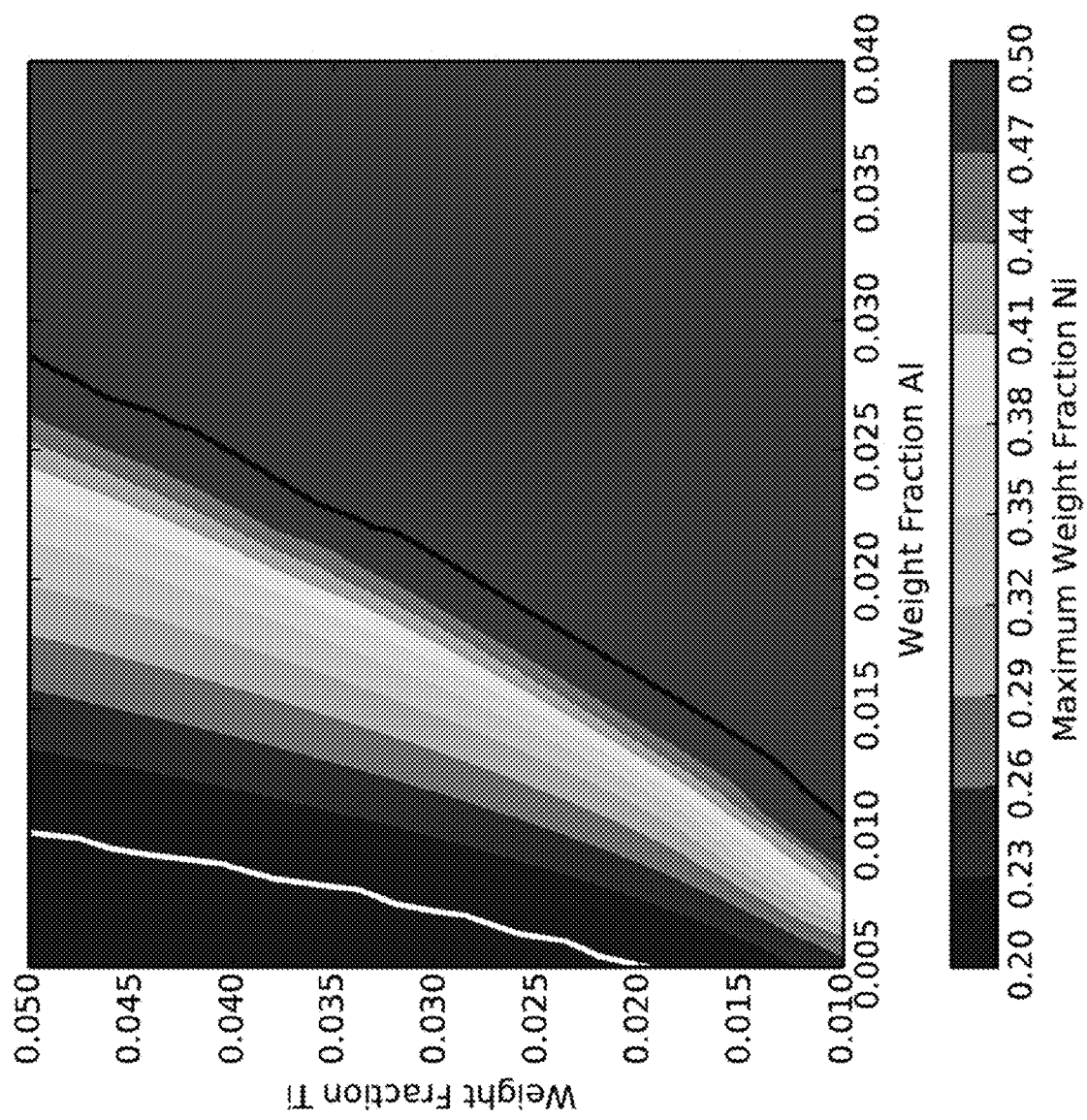
FIG. 44 shows a maximum weight fraction nickel as calculated at the ΔDF critical value of −415 J/mol, according to one embodiment of the invention.

Using the trend in FIG. 42(*c*), where decreasing weight fraction nickel leads to thermodynamically favoring of the γ' phase, a maximum weight fraction nickel can be identified to meet the thermodynamic stability goal. As FIG. 43 has calculated the driving force difference at constant weight fraction nickel, 0.235, this plot can be regenerated to incorporate changing nickel content. FIG. 44 shows the results of this analysis where at each weight fraction aluminum and titanium, the weight fraction nickel is varied and the value which yields a ΔDF of −415 J/mol is selected, which is the maximum weight fraction nickel. A minimum value of 0.20 weight fraction nickel was used as a lower bound to ensure enough nickel is present for control of the austenite stability. As seen in FIG. 44, the white line gives this bound where all the composition space to the left of that line would require less nickel to obtain a ΔDF of −415 J/mol. A maximum value of 0.50 weight fraction nickel was chosen as the design is for a high strength steel alloy, not a nickel based superalloy. Therefore all the composition space to the right of the black line can have even higher nickel contents and still thermodynamically suppress the η phase. This is a result of the drastic effect aluminum has on the driving force difference. Calculation of the maximum weight fraction nickel provides the maximum stability for given weight fractions of aluminum and titanium and when the austenite stability is lowered, γ' becomes more thermodynamically favored. FIG. 44 shows that there is a fairly large composition space for which the η phase can be thermodynamically suppressed to allow for γ' precipitation.

2.4 Strengthening Model Update

In exploring a larger composition space for the γ' precipitates than was used in the design of TRIP-180, a more complete approach to the strength modeling is adapted. This incorporates both the single (Ham) and paired dislocation strengthening. The single and paired dislocation strength models are shown below [5, 9, 17]. The shear stress increase, Δτ, is related to the tensile strength increase, Δσ, by a Taylor Factor, M.

$$\Delta \tau = \frac{\gamma_0}{2b}\left[\left(\frac{8\gamma_0 rf}{\pi G b^2}\right)^{1/2} - f\right] \quad (12)$$

$$\Delta \tau = \frac{2T_L f^{1/2}}{\pi^{3/2} br} * \sqrt{\frac{\pi r \gamma_0}{T_L} - 1} \quad (13)$$

where:
  f, r: volume fraction and average radius of γ',
  b: matrix Burger's vector (2.5 Å),
  $\gamma_0$: antiphase boundary energy (APBE) of the γ' phase,
  G: matrix shear modulus (76.54 GPa), and
  $T_L$: line tension ($\approx Gb^2/2$).

Figure 45:
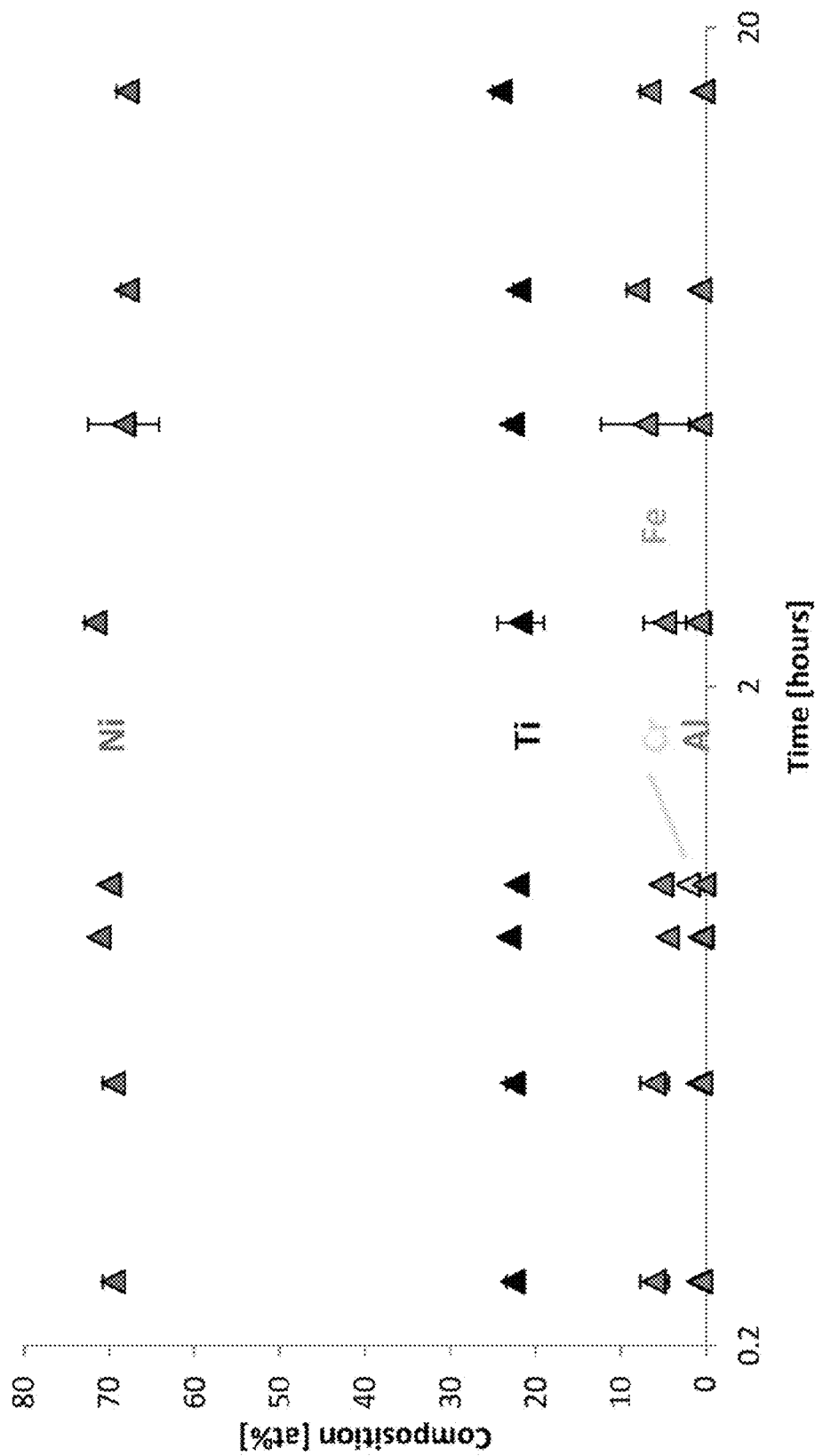
FIG. 45 shows a temporal evolution of the γ' composition in TRIP-180 from LEAP data, according to one embodiment of the invention.

These equations show that if the change in solid solution strengthening is negligible, the strength increase is based on three variables, the fraction, radius, and APBE of the γ' phase. The volume fraction and radius of the γ' precipitates are controlled by tempering times and temperatures while the APBE is a function of the composition of the γ' precipitates. In the analysis of Section 1.4, the matrix composition was shown to evolve with tempering time for TRIP-180, but the γ' composition remained constant as seen in FIG. 45. This allows for a model to be created for APBE that does not evolve with tempering but is based on the equilibrium composition of the γ' phase, which is discussed in Section 2.4.1.

Figure 46:
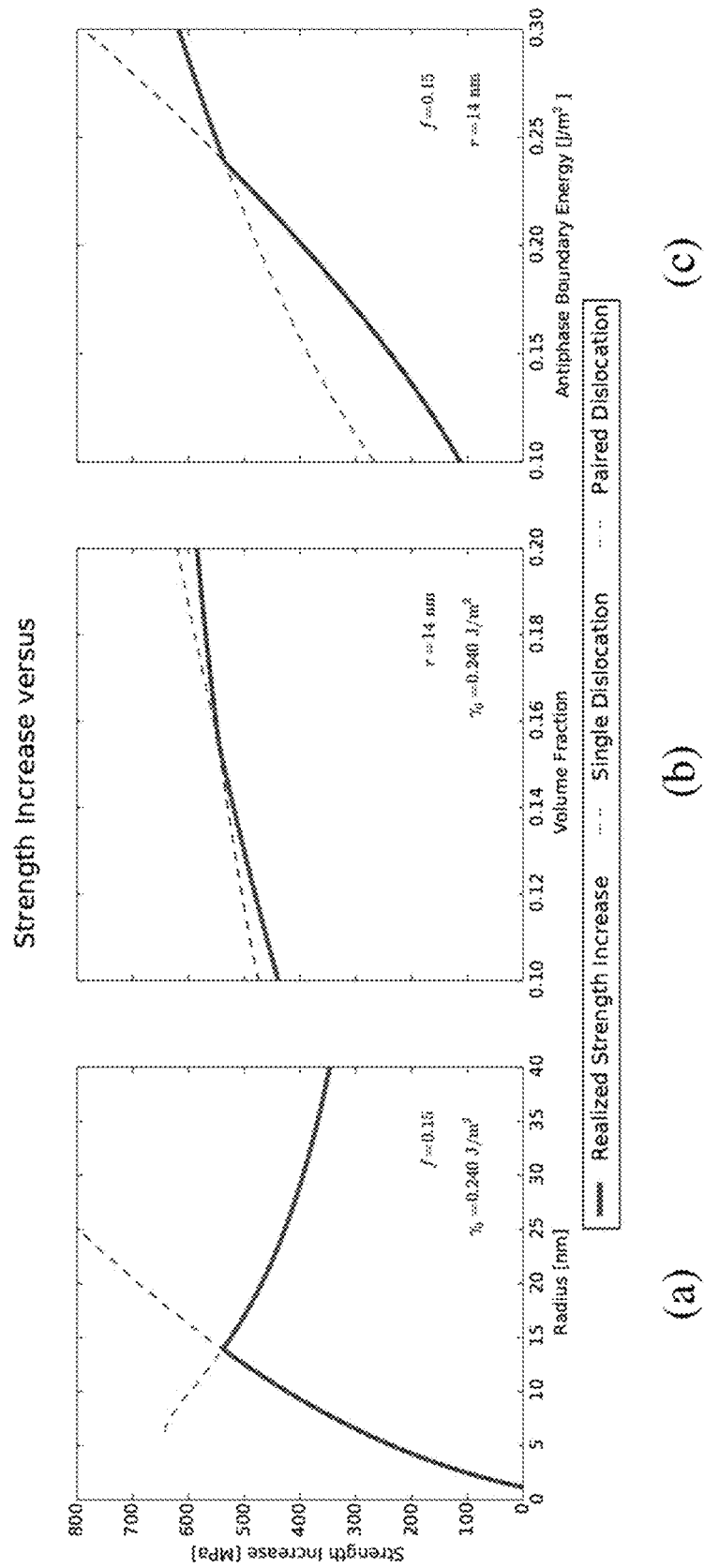
FIG. 46 shows strength increase versus (a) radius, (b) volume fraction, and (c) APBE as a function of single and paired dislocation strengthening mechanisms, according to one embodiment of the invention.

The behavior of the strength increase as a function of radius, volume fraction, and APBE is examined in FIG. 46. In FIG. 46(*a*), the relationship of strength increase with precipitation stage is large for changing radius and indicates there is a peak strengthening at an optimal radius. This shows that with radius evolution at constant volume faction and APBE, the strength increase transitions from a single to paired dislocation strengthening mechanism. In FIG. 46(*b*), the opposite is seen for volume fraction at constant radius and APBE, where the dependency on precipitation stage and changing volume fraction is small. The APBE, as seen in FIG. 46(*c*) has a large effect on the strengthening efficiency of the precipitates and has a direct correlation where a greater APBE yields a larger strength increase. The combination of Equations (12) and (13) allows for calculation of the peak strengthening of the γ' precipitates.

2.4.1 Creation of Antiphase Boundary Energy Model

Figure 47:
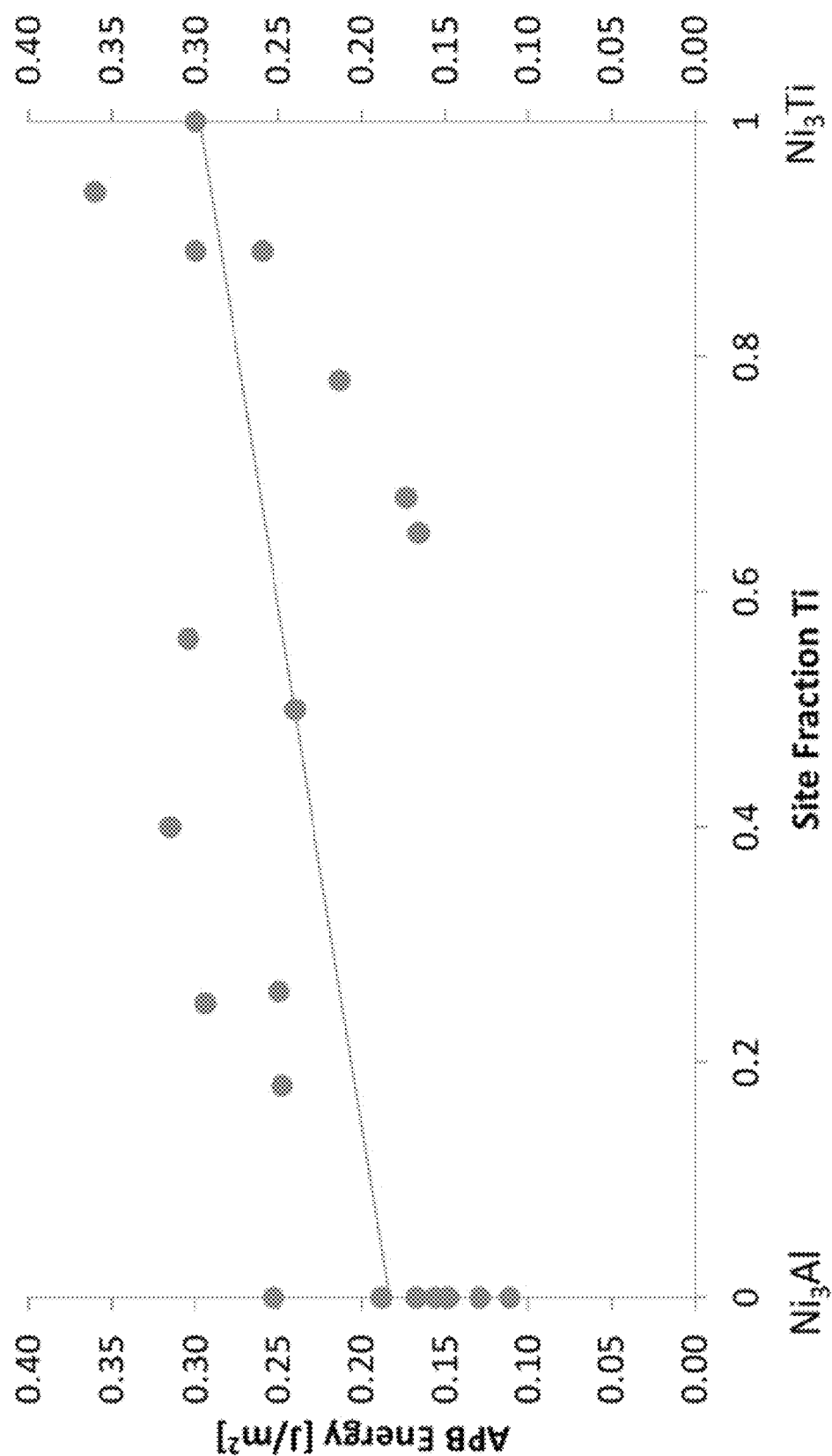
FIG. 47 shows an antiphase boundary energy model developed, according to one embodiment of the invention, showing antiphase boundary energy versus site fraction titanium [1, 3, 8, 11, 14, 17, 21].

TRIP-180 is based on the composition of EX-425 and maintains the bulk composition aluminum/titanium ratio of EX-425 to maintain the same APBE and strengthening efficiency. By changing this ratio, the site fraction of titanium on the second sublattice of the γ' Ni$_3$(Al,Ti) changes and thus the APBE changes as well. Through the course of a Materials Design Class Project at Northwestern University, a linear APBE model was developed to model the dependence of APBE on the site fraction titanium through a literature search of calculated and measured APBEs versus composition. FIG. 47 shows the results of the APBE model where Ni$_3$Al is on the left, and Ni$_3$Ti is on the right (i.e., the site fraction of titanium on the second sublattice, $Y_{Ti\,\#2}^{\gamma'}$, is zero on the left and one on the right) [1, 3, 8, 11, 14, 17, 22]. The model corresponds to the following equation where APBE is a function of site fraction titanium.

$$\gamma_0 = 0.1135 * Y_{Ti\,\#2}^{\gamma'} + 0.1834 \quad (14)$$

Figure 48:
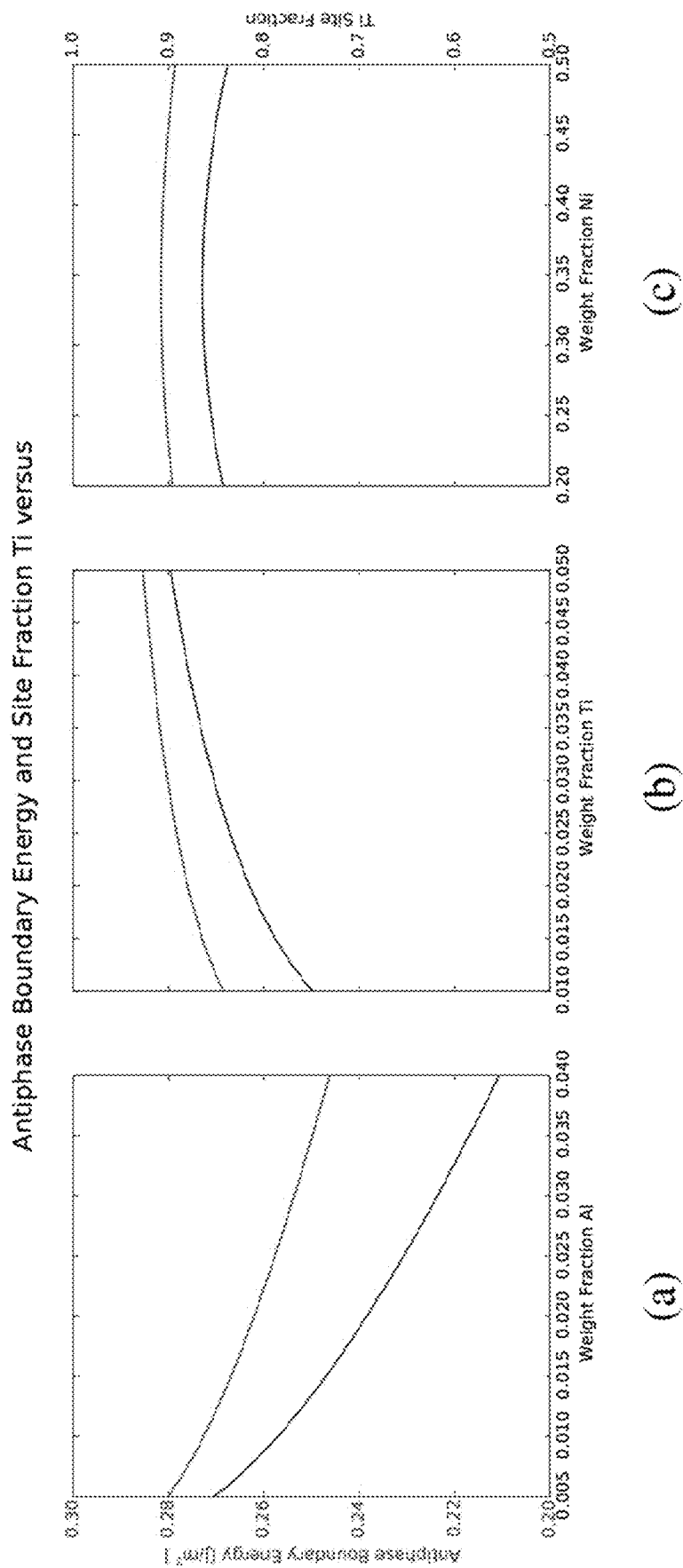
FIG. 48 shows antiphase boundary energy and titanium site fraction versus weight fraction (a) aluminum, (b) titanium, and (c) nickel. Antiphase boundary energy shown in red and titanium site fraction in blue, according to one embodiment of the invention.
Figure 49:
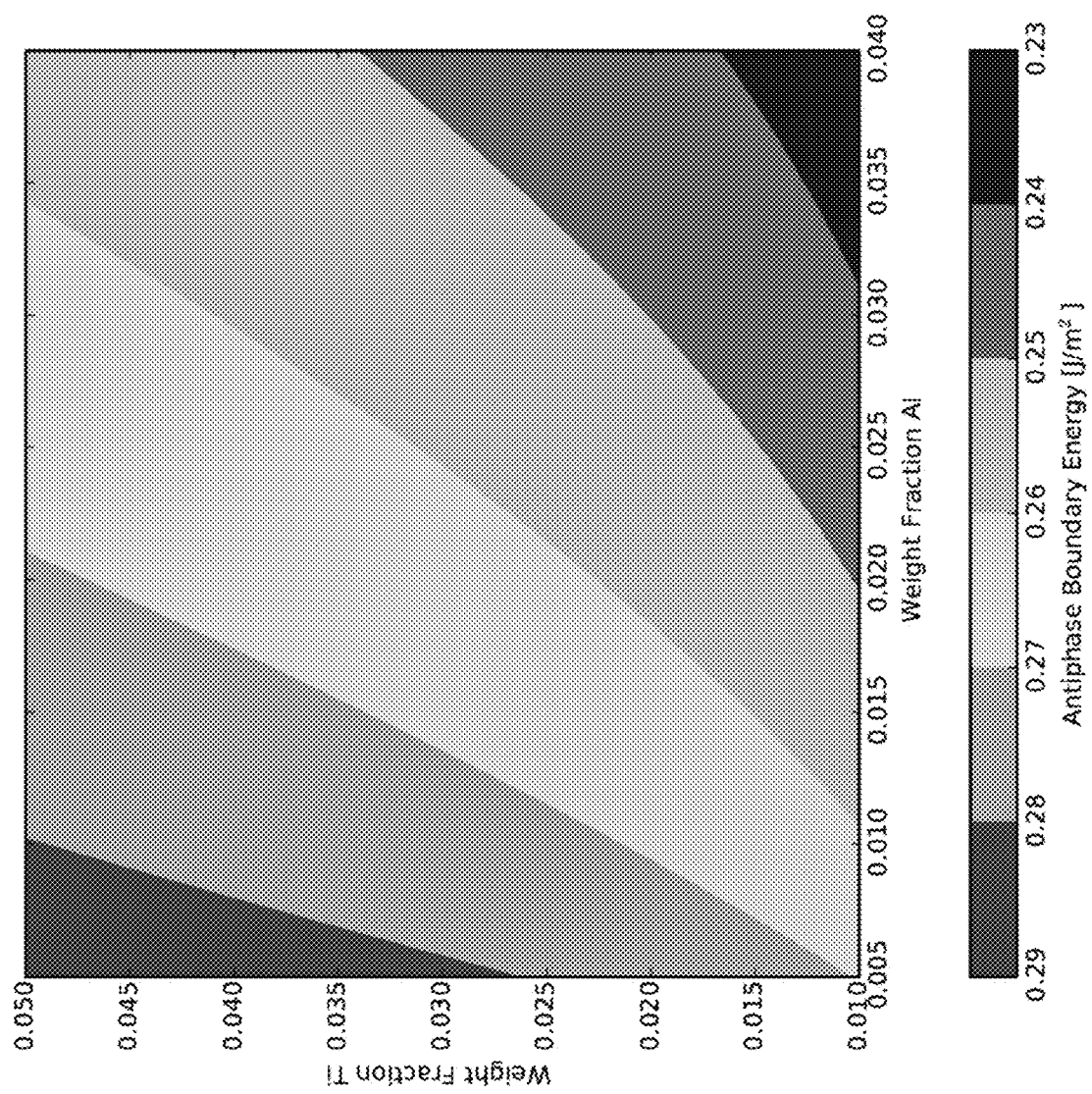
FIG. 49 shows antiphase boundary energy versus weight fraction aluminum and titanium, according to one embodiment of the invention.

FIG. 48 shows the effects of site fraction titanium and APBE energy as a function of composition. These plots indicate that the strengthening efficiency of the γ' moves in the opposite direction of thermodynamically suppressing the η phase as discussed in Section 2.3. With increasing aluminum, the strengthening of the γ' decreases but the thermodynamics favor γ'. With increasing titanium, the opposite occurs, the strengthening of the γ' increases but the thermodynamics favor η. FIG. 48(*c*) shows that the weight fraction nickel does not affect the APBE greatly, which allows for continued treatment of nickel as controlling the austenite stability and not having a large impact on strengthening. FIG. 49 shows the effect of initial bulk composition and varying aluminum and titanium contents on APBE. Higher strengthening efficiency is seen at high titanium and low aluminum, the opposite of the thermodynamic stability in FIG. 43 where greater thermodynamic stability of the γ' phase is at high aluminum and low titanium.

2.5 Achieving the Strength Goal

In order to achieve the strength goal of 896 MPa (130 ksi) as well as prevent the grain boundary cellular precipitation of η at grain boundaries, the precipitation of γ' needs to be controlled. Given the base strength of the austenite without γ' strengthening is 341 MPa as measured in TRIP-180 [8], the required strength increase from the γ' precipitates must be 554 MPa. As seen in FIG. 46, the strengthening peaks at the intersection of the single and paired dislocation strengthening models for increasing radius, but continues to increase with increasing volume fraction and APBE. Thus, to achieve the strength goal, the precipitation must be controlled to obtain the radius at peak strengthening with a larger volume fraction if the APBE is decreased from the design of TRIP-180, as it is to satisfy the thermodynamic criterion discussed in Section 2.3. The effect of aluminum, titanium, and nickel additions on the APBE energy is shown in FIG.

48. The γ' radius is the result of nucleation and coarsening during tempering and can be utilized in Thermo-Calc calculations by the addition of capillary energy to the thermodynamic description of the γ' phase. The capillary energy and radius are related through a Gibbs-Thomson effect as discussed in Section 1.4.2 and shown below in Equation (15).

$$\Delta g = \frac{2\sigma}{r} \quad (15)$$

Figure 50:
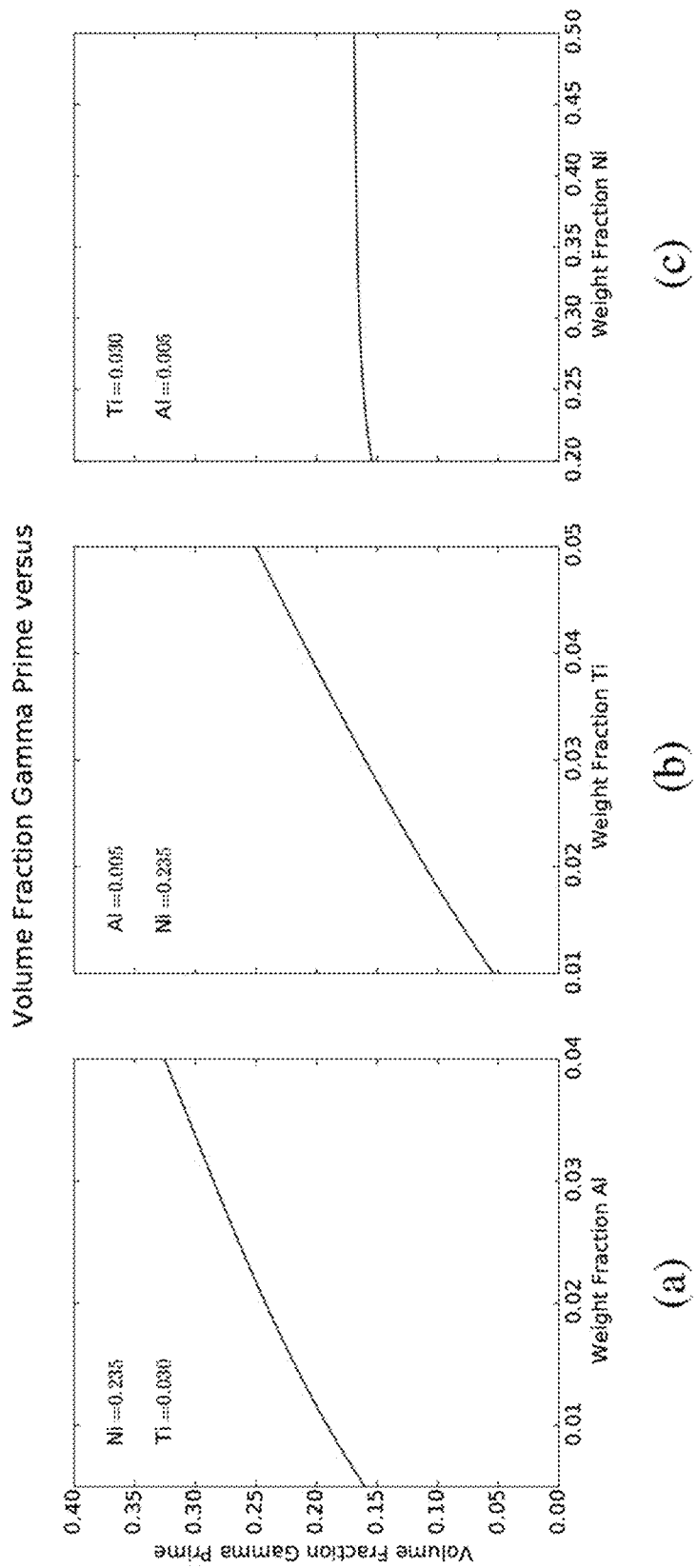
FIG. 50 shows volume fraction γ' values versus weight fraction (a) aluminum, (b) titanium, and (c) nickel, according to one embodiment of the invention.

The composition dependence of the equilibrium, and thus maximum, volume fraction is investigated in FIG. 50. This figure shows that the quantity of γ' is directly controlled by the additions of aluminum and titanium, as the atomic fraction of nickel is much larger than three times the sum of the atomic fractions of aluminum and titanium to be stoichiometric in composition ($Ni_3$ (Al,Ti)). The additions of aluminum and titanium contribute to the volume fraction γ' if they are above their equilibrium solubilities in the FCC austenite matrix.

Figure 51:
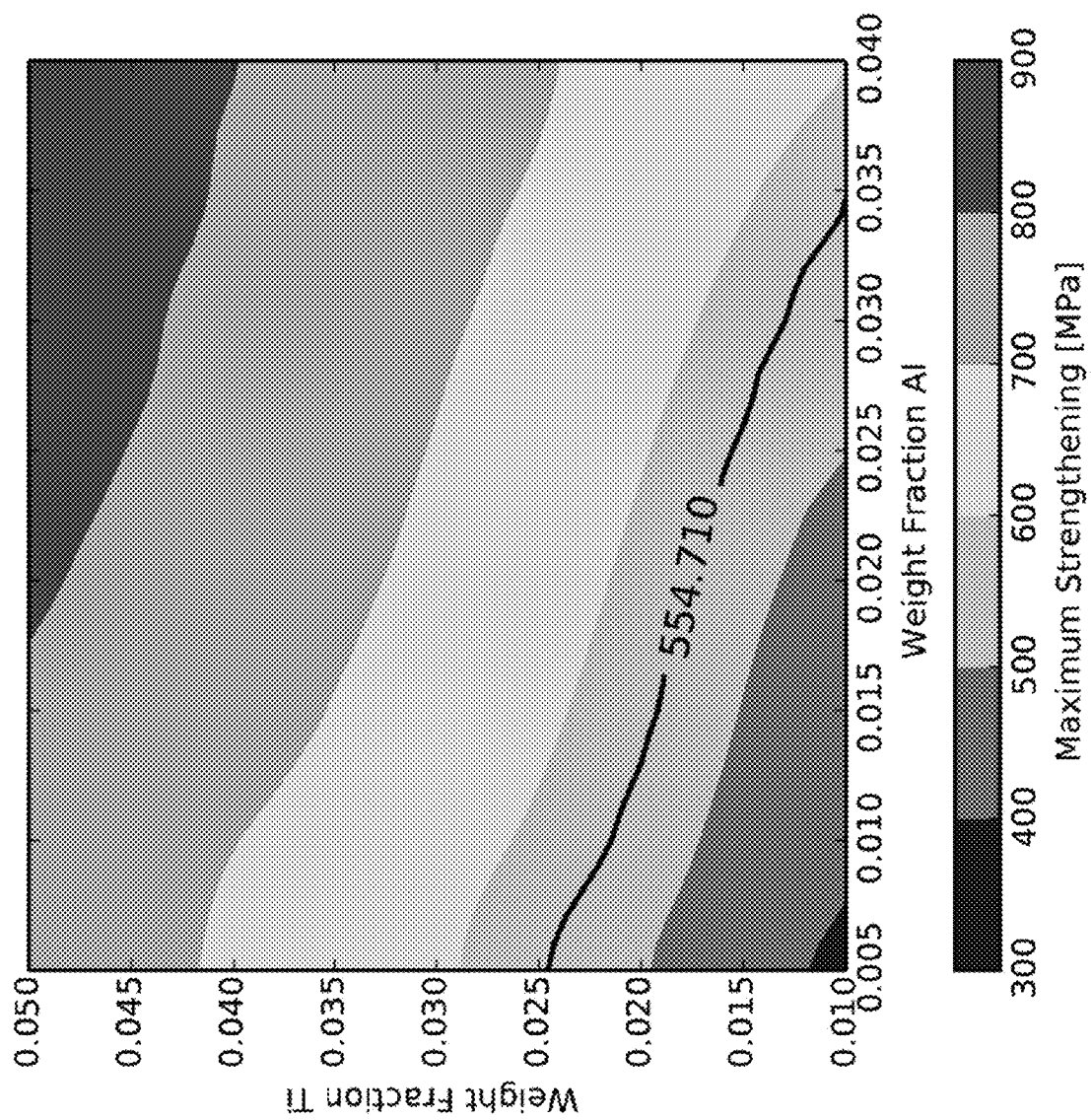
FIG. 51 shows a maximum strengthening with goal strengthening indicated, 554.71 MPa, as a function of weight fraction aluminum and titanium, according to one embodiment of the invention.
Figure 52:
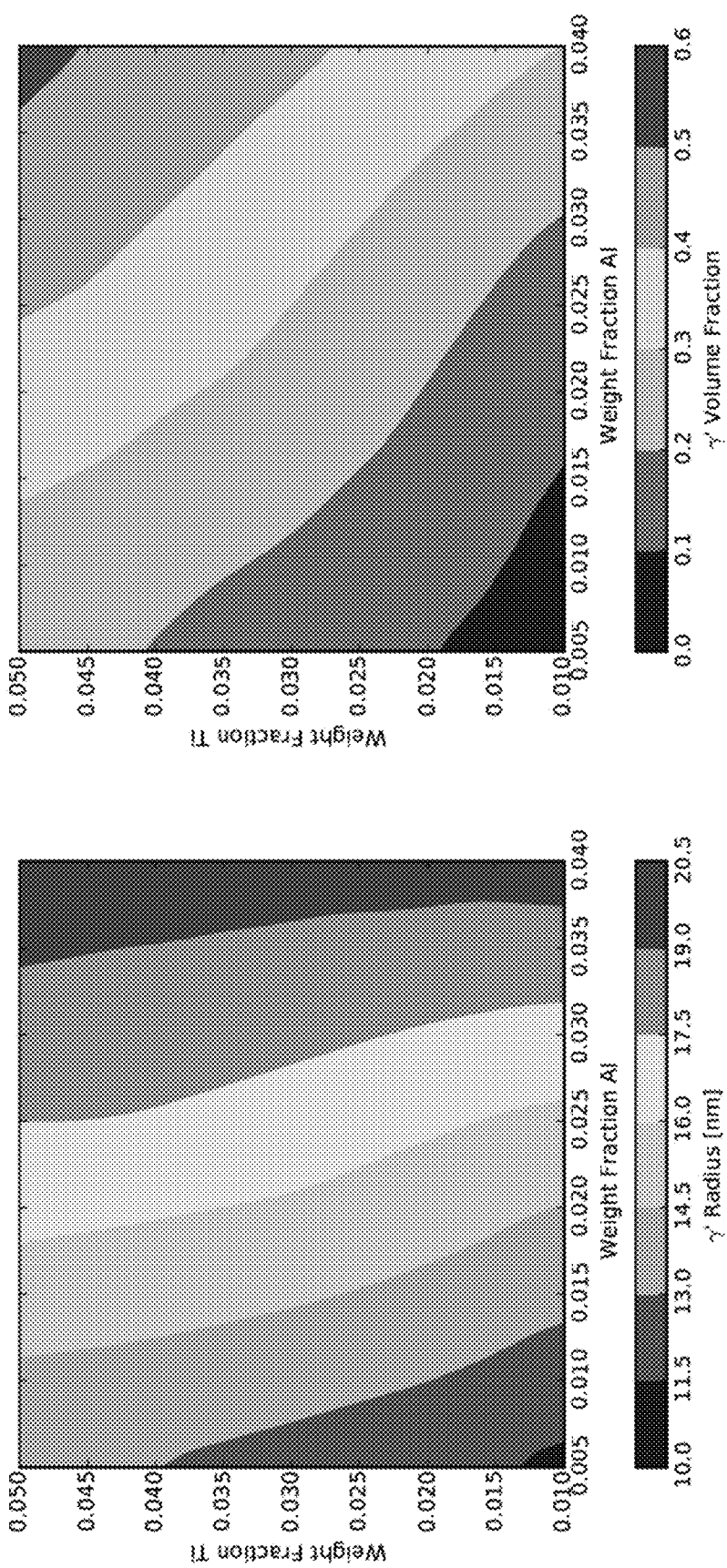
FIG. 52 shows (a) radius and (b) volume fraction at peak strengthening as a function of weight fraction aluminum and titanium, according to one embodiment of the invention.

To calculate the strengthening addition of the γ' phase, the values of radius, volume fraction, and APBE must be calculated at each composition. APBE remains constant at each composition as discussed in Section 2.4 and is easily calculated using Thermo-Calc and the model in Equation (14). Using Equation (15), the capillary energy at each γ' radius (at each composition) can be evaluated and performing a Thermo-Calc constrained equilibrium calculation with the added energy yields the γ' volume fraction. At small radii, the capillary energy is large and the resulting volume fraction is small. As the precipitate radii grow (i.e., r→∞), the capillary energy reduces to zero, and the equilibrium volume fraction is reached. Thus, the volume fraction and radius are linked, which allows for calculation of strengthening at each titanium and aluminum composition as nickel does not affect the APBE or volume fraction as shown in FIGS. 48(c) and 50(c). Using the single and paired dislocation strengthening models, the maximum strengthening of the γ' phase can be calculated. The results of this analysis are shown in FIG. 51 where the strength addition to reach 896 MPa, 554 MPa, is shown. The calculated radii and volume fractions at the peak strengthening are shown in FIG. 52. It was assumed that the radii at peak strengthening would be larger than the critical radius for coherency transition, and thus calculations were only performed for radii greater than 5 nm.

Figure 53:
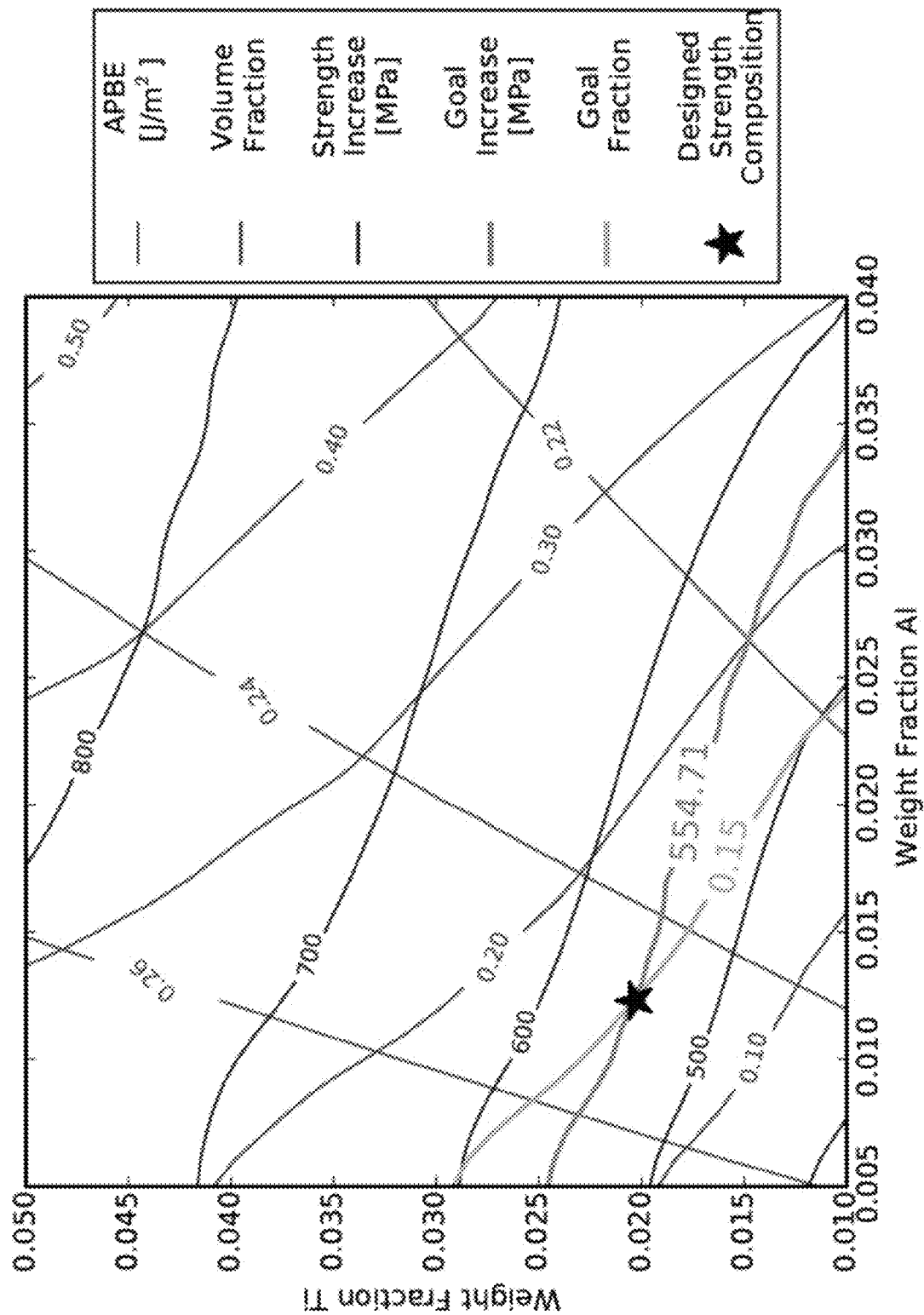
FIG. 53 shows contour plot showing strength increase, volume fraction at maximum strength, APBE, and goals for strength and strengthening efficiency, according to one embodiment of the invention. The chosen design composition for achieving the strength goal is shown as a black star.

The contour plot in FIG. 53 is a compilation of several variables shown to guide the selection of the weight fractions of aluminum and titanium that reach the strength goal. It shows the maximum strength increase from the γ' precipitation, the volume fraction at the maximum strength, and the APBE energy. It is seen at given iso-strengthening contours the APBE increases and the volume fraction decreases when titanium is substituted for aluminum. This indicates the strengthening efficiency is greater when more titanium is present. As to maintain strengthening efficiency, and not have the γ' phase grow so large, a phase fraction goal of 0.15 is selected. FIG. 53 also shows the goal strength increase and the new volume fraction goal. The contours overlap at weight fractions aluminum and titanium of 0.0123 and 0.0203, respectively. The capillary energy added to achieve a volume faction of 0.15 is 254 J/mol which yields a radius of 13.343 nm and an APBE of 0.2485 J/m².

2.6 Achieving the Austenite Stability Goal

The stability of the austenite is controlled primarily by the nickel and chromium content remaining in the matrix after the precipitation of the γ'. To control the austenite stability in this design, nickel was selected to vary with the chromium content constant. By taking the weight fractions of aluminum and titanium designed for in Section 2.5 of 0.0123 and 0.0203, respectively, the maximum weight fraction nickel can be determined through the analysis that generated FIG. 44. This maximum weight fraction is 0.3373. The Olson-Cohen relation, reproduced below in Equation (16), can be solved versus weight fraction nickel for the $M_s^o$(u.t.) and $M_s^o$(sh) temperatures and implemented for the LEAP results in Section 1.5.

$$\Delta G_{ch} + \Delta G_\alpha = -G_n - W_f^{sol}$$

when $\sigma = \sigma_y$ and $T = M_s^\sigma$ (16)

Figure 54:
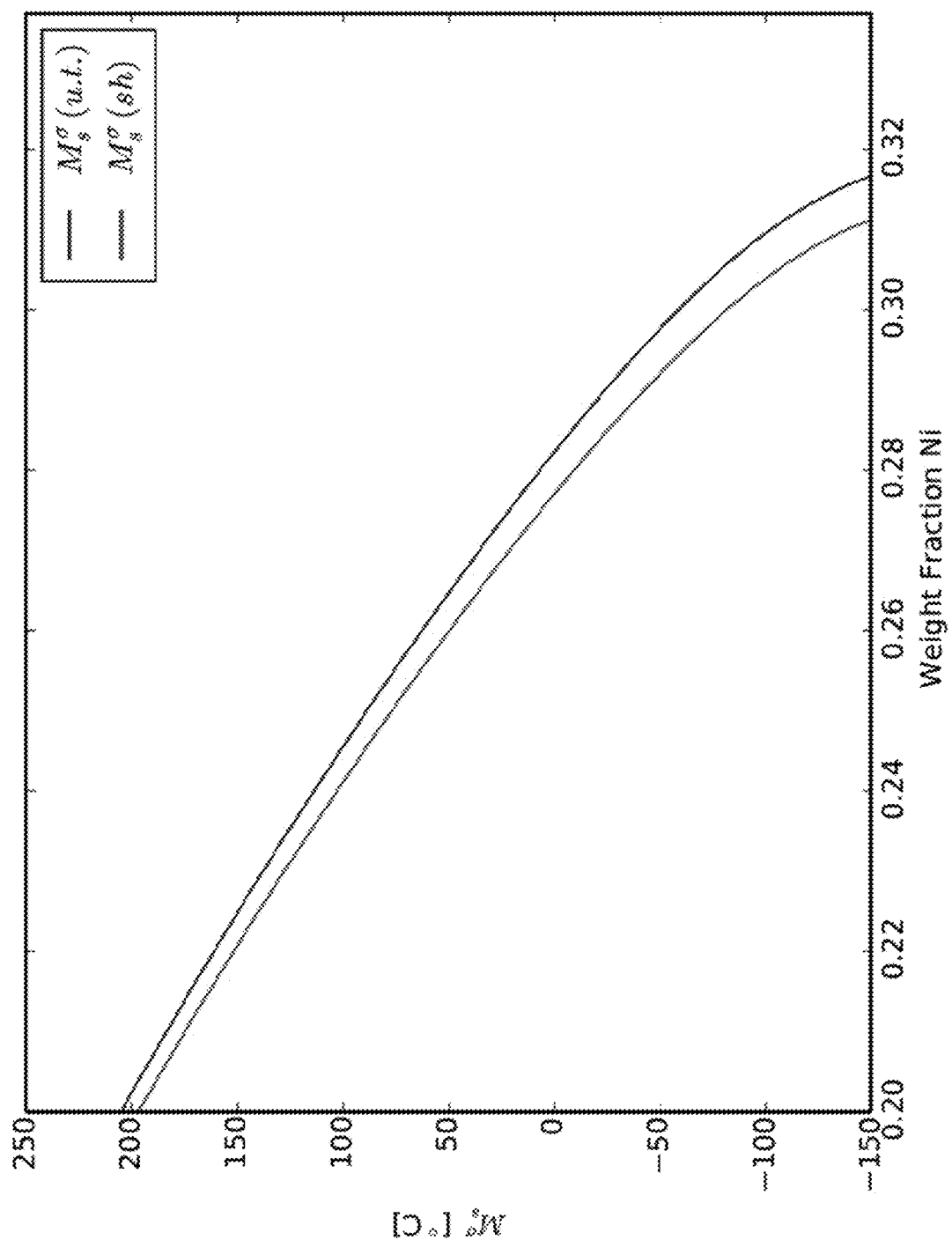
FIG. 54 shows $M_s^\sigma$ temperatures versus weight fraction nickel, according to one embodiment of the invention.

The results are shown in FIG. 54. It is shown that as nickel content increases, the stability of the austenite increases and the $M_s^o$ temperatures decrease, as expected. From FIG. 38, the required weight fraction nickel to achieve the austenite stability goal of $M_s^o$(sh)=−40° C. is 0.2893.

Figure 55:
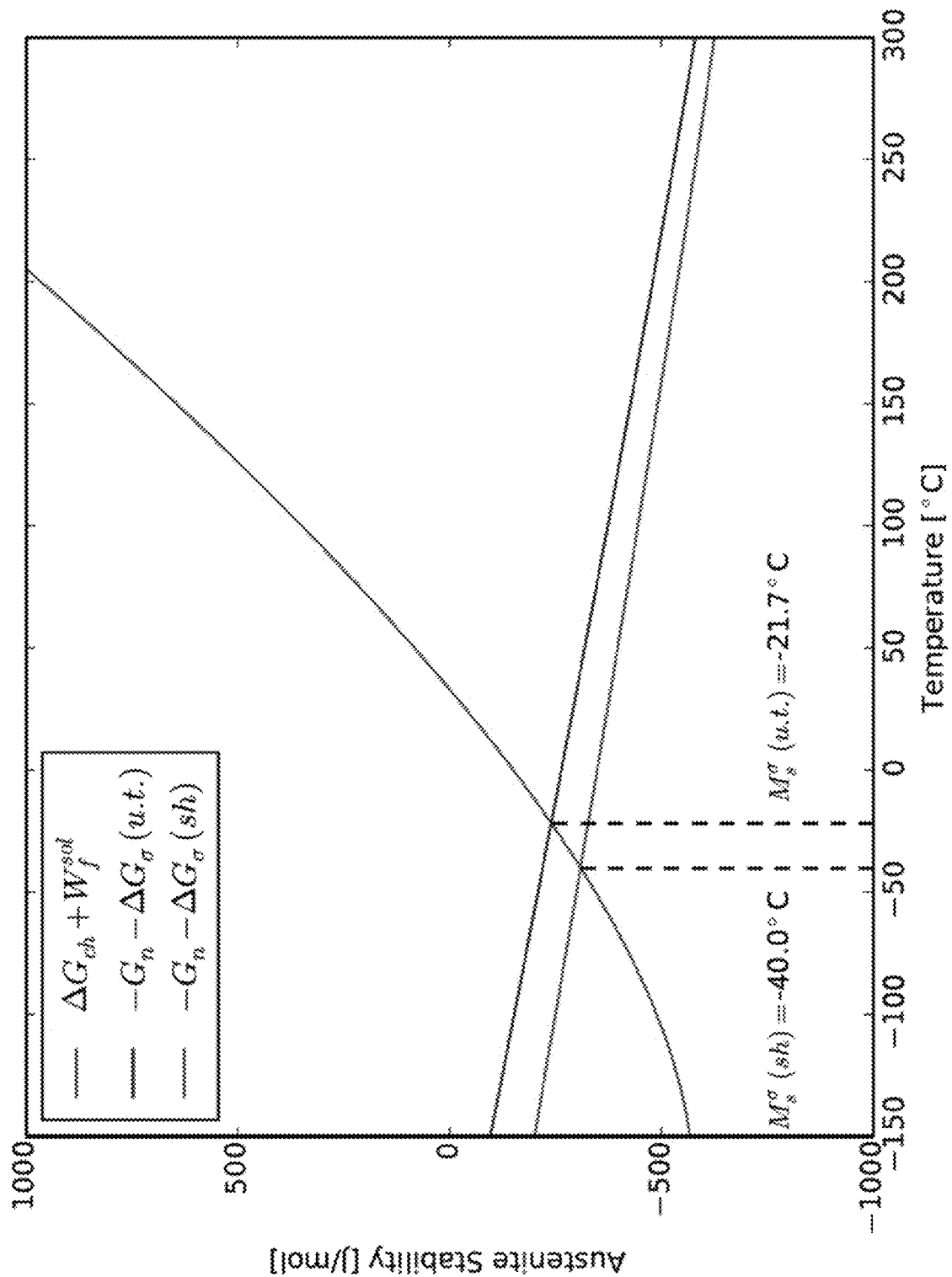
FIG. 55 shows austenite stability versus temperature for uniform tension and shear loading conditions, according to one embodiment of the invention. The intersections of the composition dependent and microstructure dependent terms yield the $M_s^\sigma$ temperatures.

At an aluminum, titanium, and nickel weight fraction of 0.0123, 0.203, and 0.2893, respectively, FIG. 55 shows the curves for the composition dependent terms, $\Delta G_{ch} + W_f^{sol}$, and the microstructure dependent terms, $-G_n - \Delta G_o$, of the resulting alloy. The figure shows the $M_s^o$(sh) and $M_s^o$(u.t.) temperatures to be −40° C. and −21.7° C. This composition achieves the desired austenite stability.

2.7 Blastalloy TRIP 130 Design Composition

Figure 56:
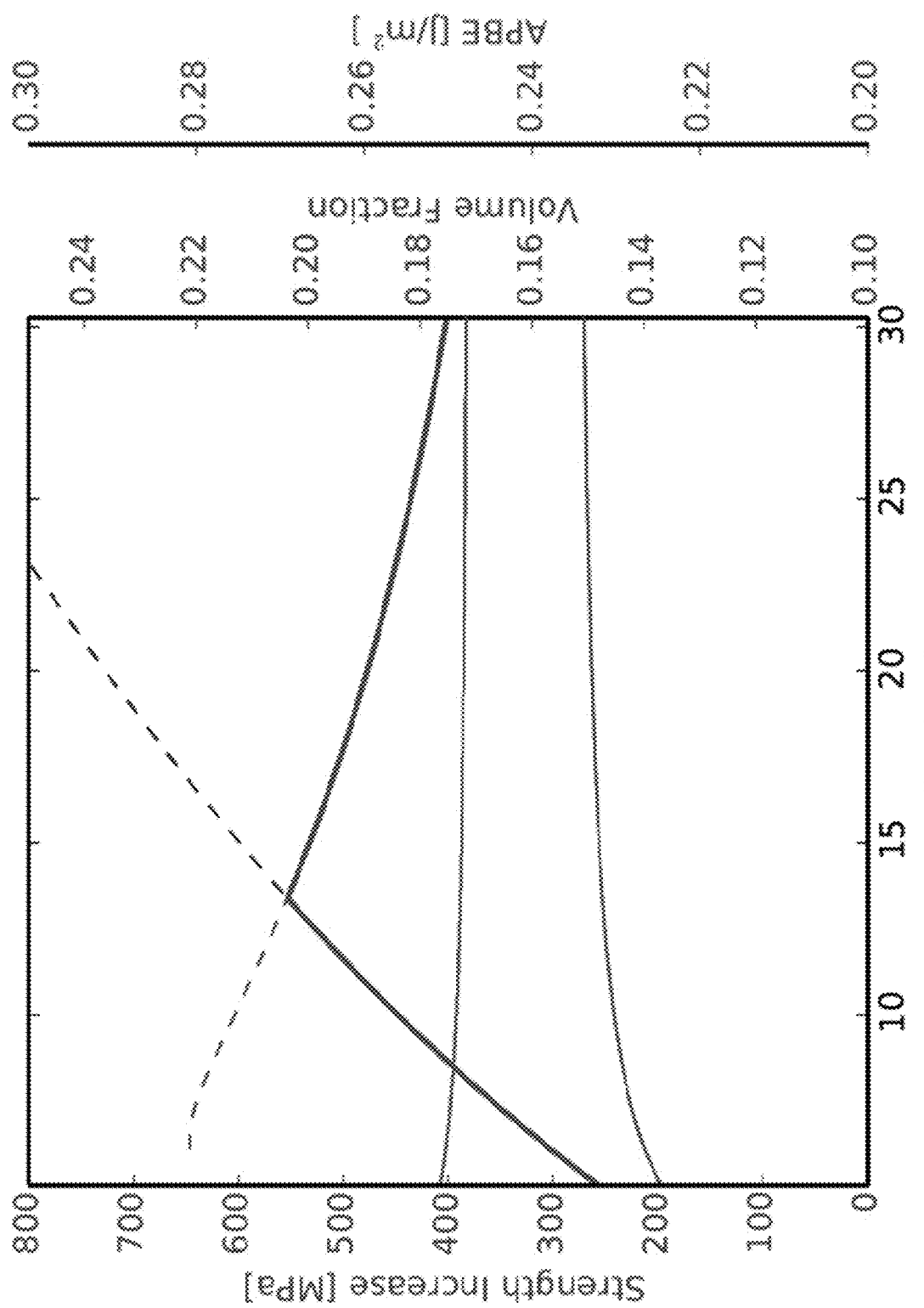
FIG. 56 shows austenite stability versus temperature for uniform tension and shear loading conditions, according to one embodiment of the invention. The intersections of the composition dependent and microstructure dependent terms yield the $M_s^\sigma$ temperatures.

From the previous sections, the design of Blastalloy TRIP 130 has weight fractions of aluminum, titanium, and nickel as 0.0123, 0.0203, and 0.2893, respectively. To ensure that controlling the austenite stability to have a $M_s^o$(sh) temperature of −40° C. by reducing the nickel content did not change the strengthening contribution of the γ', the strengthening contribution is recalculated at the above composition. FIG. 56 compiles these results. At peak strengthening, which is 552 MPa for a total yield strength of 893 MPa (130 ksi), the radius is 13.3 nm, the volume fraction is 0.147, the APBE is 0.25 J/m², and the added capillary energy is 254 J/mol. This shows that the values calculated for achieving the strength goal in Section 2.5 remained essentially the same even with changing the nickel content as expected from FIGS. 48(c) and 50(c). To check for thermodynamic stability, the driving force difference was calculated to be −284 J/mol, which is above the minimum value of −415 J/mol as a calculated baseline from A-286.

TABLE 10

Composition of Blastalloy TRIP 130.

|  | Ni | Cr | Ti | Al | Mo | V | C | B | Fe |
|---|---|---|---|---|---|---|---|---|---|
| wt. % | 28.93 ±0.2 | 4.0 ±0.2 | 2.03 ±0.1 | 1.23 ±0.05 | 1.2 ±0.05 | 0.3 ±0.05 | 0.01 ±0.005 | 0.0125 ±0.005 | Bal. |

TABLE 11

Specifications at peak strengthening and optimum austenite stability for Blastalloy TRIP 130.

| r | f | $\gamma_0$ (J/m$^2$) | $\Delta\sigma$ (MPa) | $\sigma_y$ (MPa) | $M_s^\sigma$ (sh) (° C.) | $M_s^\sigma$ (u.t.) (° C.) | $\Delta$DF (J/mol) |
|---|---|---|---|---|---|---|---|
| 343 | 0.1473 | 0.2489 | 551.80 | 893.08 | −40.0 | −21.7 | −284 |

The final design composition of Blastalloy TRIP 130 is shown in Table 10. Table 11 tabulates the strengthening contributions, austenite stability, and thermodynamic stability of the newly designed alloy at peak strengthening. This information shows that the design meets the optimized austenite stability, exceeds the minimum thermodynamic stability and is slightly lower than the strength goal by approximately 3 MPa (0.5 ksi). To further evaluate the thermodynamic stability of the γ' phase, a phase field of the γ, γ', and η phases was created in FIG. 57 where all other phases are not present in the shown composition space. Blastalloy TRIP 130, even at equilibrium conditions, does not have η precipitation as illustrated by the black star. This is shown in comparison to TRIP-180, shown as the blue diamond, which at equilibrium does not include γ' but rather only γ and η. This is indicative of the long aging times resulting in precipitation of η in TRIP-180 through Feinberg's research [8].

Blastalloy TRIP 130 was designed based off the designed composition of TRIP-180 with the weight fractions of aluminum and titanium chosen to achieve the strength and thermodynamic stability goals and the weight fraction nickel to achieve the austenite stability goal. This prototype alloy is briefly evaluated in Section 3.

2.8 Processing Design

From the parametric modeling in the previous sections, the composition of Blastalloy TRIP 130 is designed to meet the property objectives detailed in Table 8. To finish the design, the processing steps must be controlled to ensure the desired structure, properties, and performance are achieved. As shown in FIG. 40, the three heat treating steps are the homogenization, solution treatment, and tempering or aging.

Figure 58:
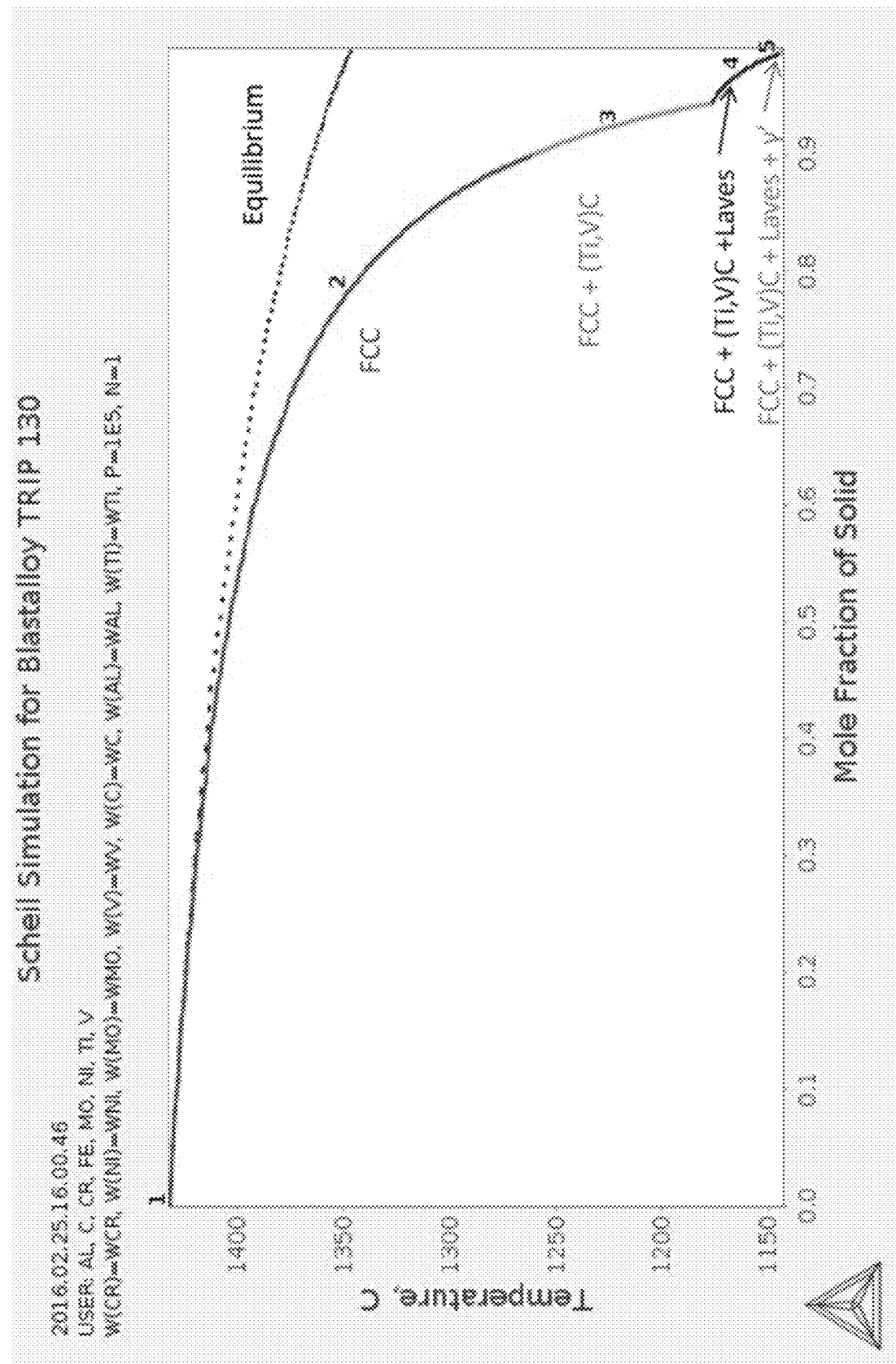
FIG. 58 shows a Scheil simulation for Blastalloy TRIP 130, according to one embodiment of the invention, colored lines, as compared to equilibrium solidification model, dotted black line. Simulation performed using the Ni-Data 7 database.

The homogenization temperature and time is chosen at a high enough temperature to promote fast diffusion, but below a temperature to prevent incipient melting. To effectively model the extreme case of incipient melting during solidification as compared to equilibrium solidification, a Scheil simulation was performed using the Scheil module in Thermo-Calc. The Scheil simulation implements the Scheil-Gulliver equation for solute redistribution during solidification. FIG. 58 shows the results of the Scheil simulation of Blastalloy TRIP 130 compared to the equilibrium solidification model. The equilibrium solidification model follows the liquidus line and is the black dotted line. The solid lines represent the Scheil simulation where each new color represents the solidification of another solid phase. The Scheil simulation indicates that the lowest possible temperature where liquid should be present as 1143° C. For TRIP-180 the temperature is calculated to be 1138° C. This indicates that the solidification behavior between Blastalloy TRIP 130 and TRIP-180 are similar and the homogenization temperature and time for TRIP-180, 1190° C. for 24 hrs, can be used for Blastalloy TRIP 130. In order to ensure that incipient melting does not occur, a step homogenization process is implemented, where the alloy is held at 1093° C. (2000° F.) for 6 hrs and then stepped up in temperature to 1204° C. (2200° F.) for the final 18 hrs.

Figure 59:
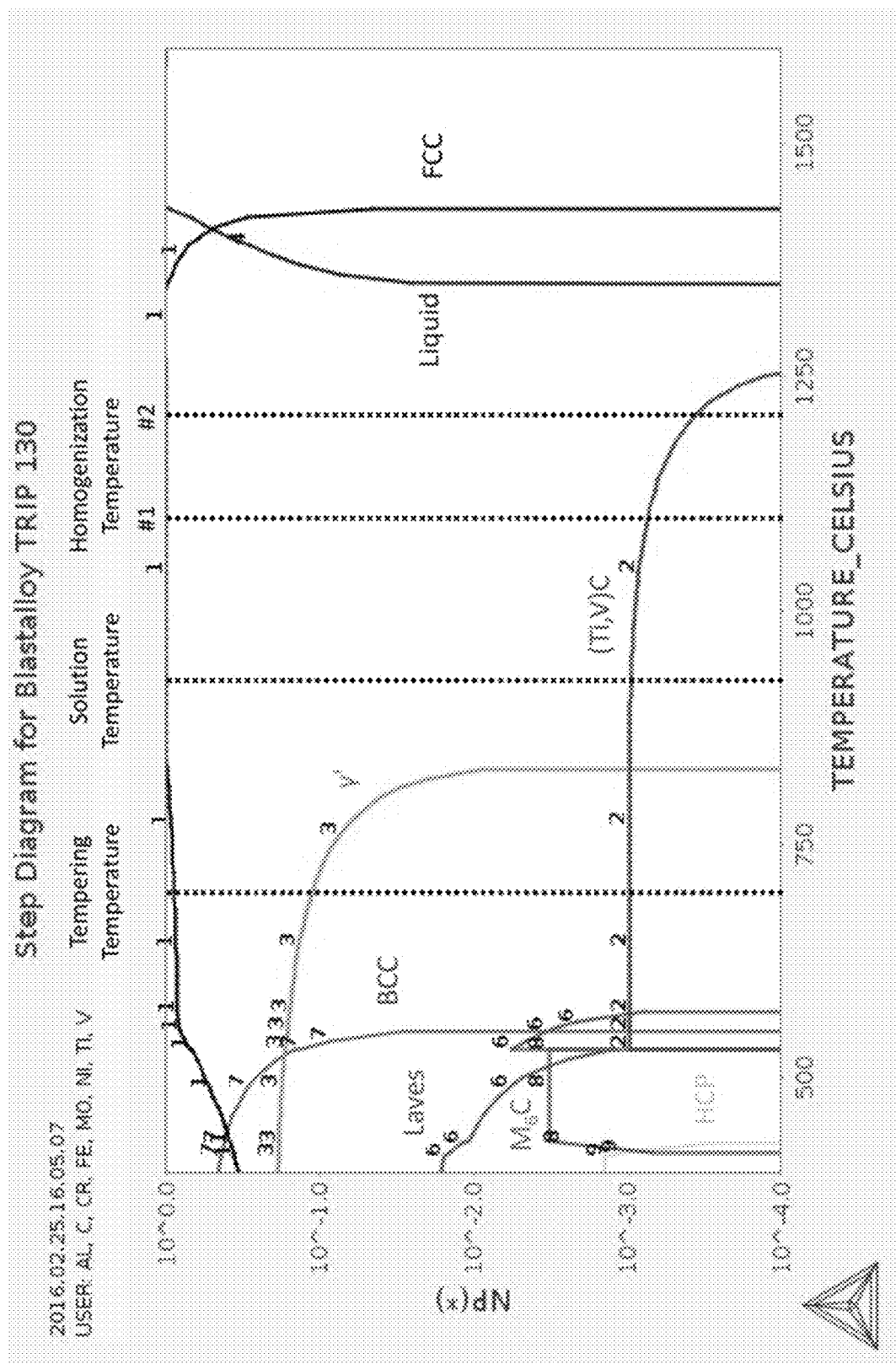
FIG. 59 shows a step diagram of Blastalloy TRIP 130 showing the designed heat treatment temperature as black dashed lines, according to one embodiment of the invention. Calculation performed using the Ni-Data 7 database.

The solution temperature is selected not only at a temperature above where the γ' phase is in solution, but also where the grain refining titanium carbide phase is present. The titanium carbide phase allows for grain boundary pinning in order to maintain the grain structure achieved by the hot working. In Thermo-Calc the titanium carbide phase is the second composition set of the FCC matrix, FCC_A1#2. The solution treatment step is chosen as 926° C. (1700° F.) for 1 hr. These temperatures are displayed in the step diagram showing all the phases present at equilibrium in the alloy as a function of temperature, shown in FIG. 59. The designed tempering temperature is also indicated on this plot. FIG. 59 shows that at the solution temperature the only phases present are the austenite matrix and titanium carbide grain refiners. In addition, the tempering temperature can be modified from approximately 600° to 800° C. and still only the γ' phase would precipitate out. This allows for flexibility within this processing step.

Figure 60:
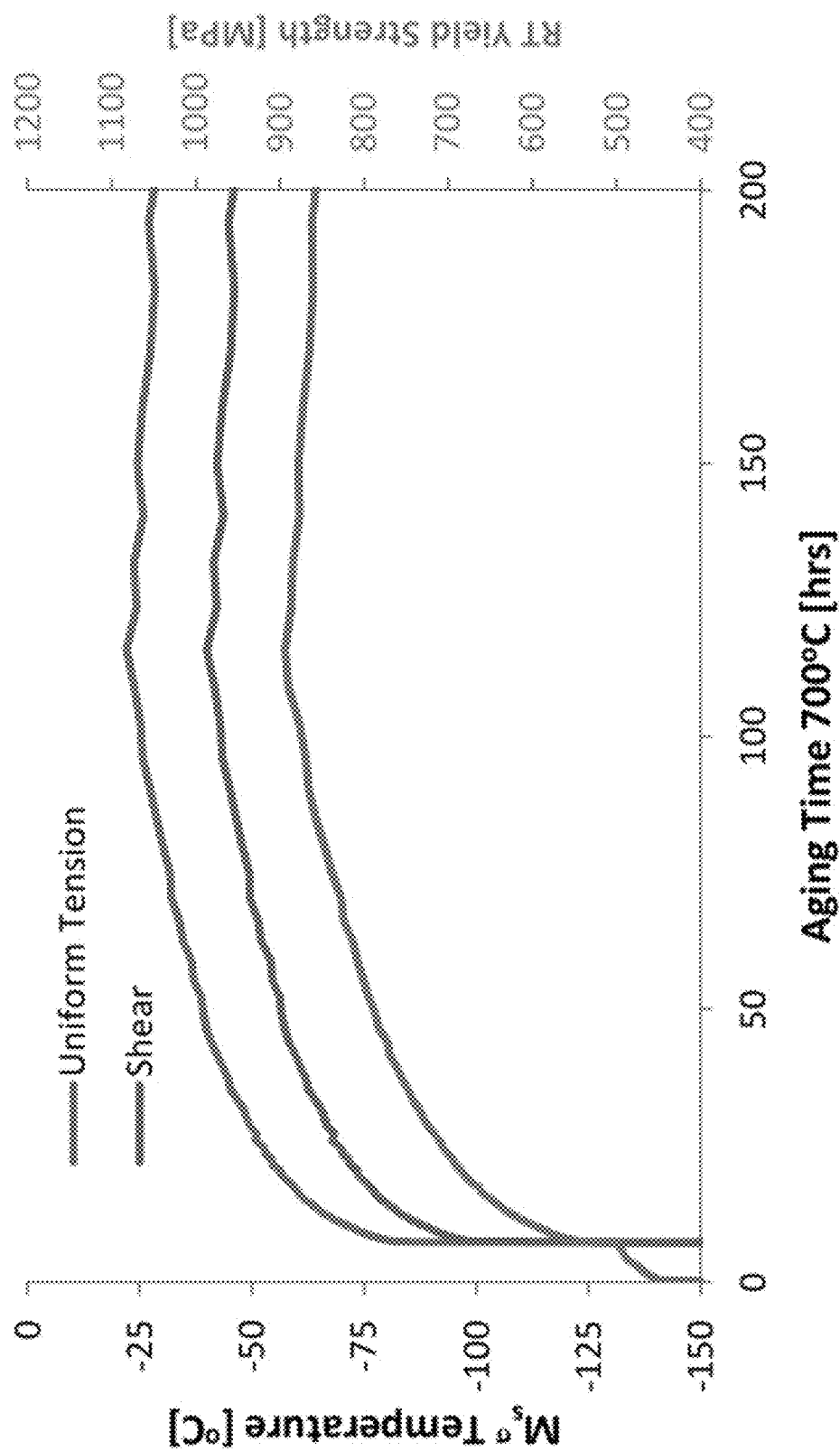
FIG. 60 shows $M_s^\sigma$ temperature model showing predictions for $M_s^\sigma$(u.t.) and $M_s^\sigma$(sh) at parametrically designed aging temperature of 700° C., according to one embodiment of the invention. The calculated room temperature yield strength is shown in green on the second y-axis.

In order to determine the aging time at 700° C. for Blastalloy TRIP 130 to reach peak strengthening and optimum austenite stability, the PrecipiCalc models calibrated in Section 1.6 are used to simulate the precipitation kinetics of the γ' precipitates. At each timestep of output, the room temperature yield strength and the $M_s^\sigma$ temperatures were calculated. FIG. 60 shows these results where the calculated peak strength of 893.7 MPa aligns with the optimum $M_s^\sigma$ (sh) temperature of −39.95° C. The optimized tempering time for Blastalloy TRIP 130 is calculated to be 116 hrs at 700° C. which is nonideal for commercial aging times. The optimized strengthening time also corresponds to the r* value of 13.3 nm as calculated in Section 2.7. The critical radius of transition between coherent and incoherent precipitation, $r_{crit}$ is seen in the discontinuity in the curvature of the yield strength curve which occurs after approximately 7.25 hrs of aging.

Figure 61:
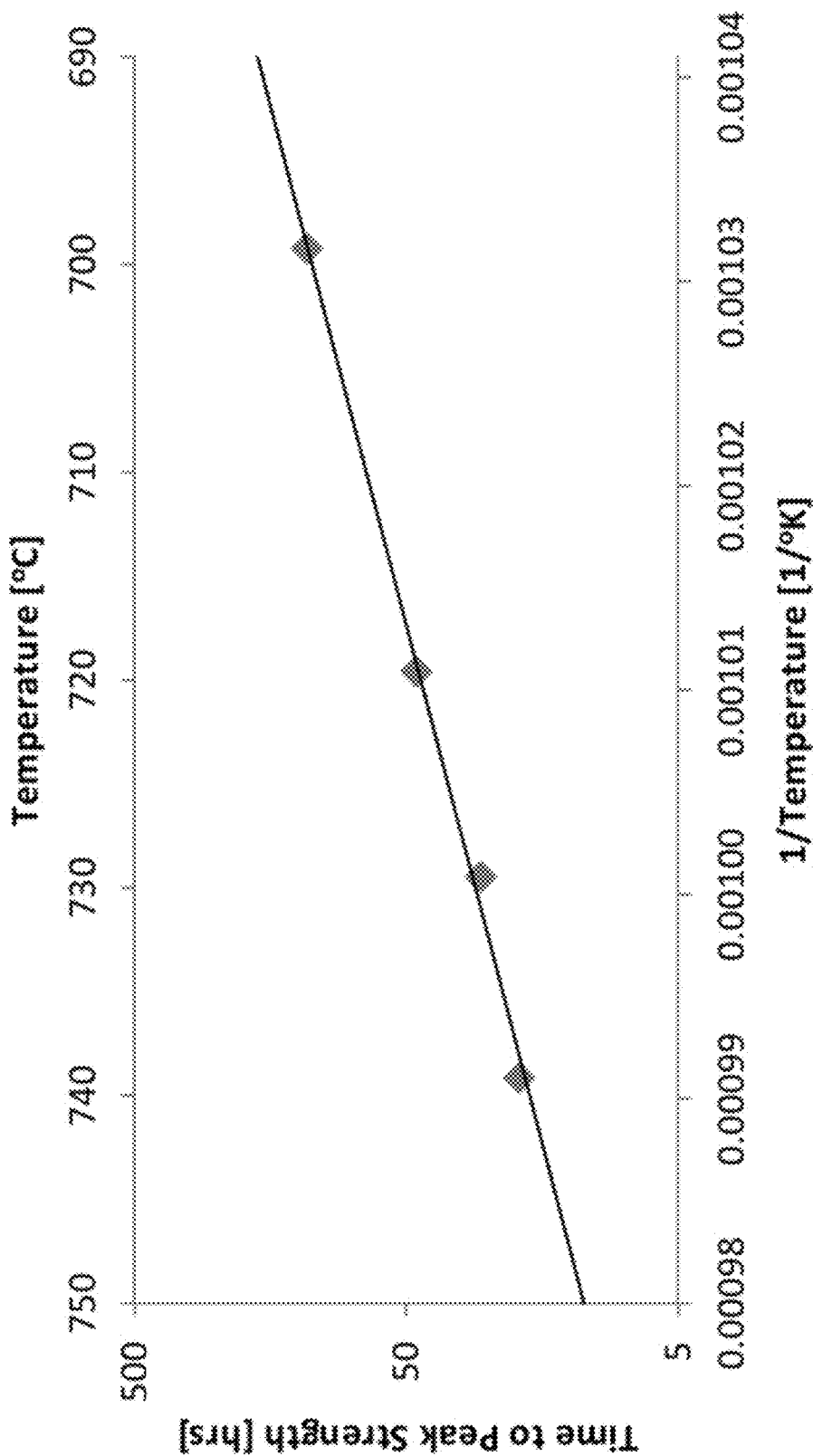
FIG. 61 shows precipitation rate predictions for the precipitation kinetics of Blastalloy TRIP 130 as the time to calculated peak strength through four PrecipiCalc simulations, according to one embodiment of the invention.

To reduce the aging time to less than 20 hrs, several PrecipiCalc simulations were run at different tempering times to create precipitation predictions aligning time to peak strength to the aging temperature. The aging temperatures of the additional simulations are 720° C., 730° C., and 740° C. The results are shown in FIG. 61. When plotted as the log of time to strengthening, $t_p$, versus inverse temperature in Kelvin, a linear relationship is observed as shown in Equation (17).

$$\ln t_p = 23818 \frac{1}{T} - 29.279 \tag{17}$$

The aging temperature calculated to achieve peak strengthening at 20 hrs is 738° C. When increasing the temperature, the volume fraction of the γ' is reduced as seen in the step diagram in FIG. 59. This slightly reduces the peak yield strength and increases the austenite stability as more nickel remains in the matrix. Therefore, to achieve the designed strength and austenite stability, an 18 hr age at 740°

C. is followed by a furnace cooling to a 2 hr age at 700° C. This achieves a yield strength of 887.6 MPa and a $M_s^\circ(sh)$ temperature of −39.5° C.

3 Preliminary Blastalloy TRIP 130 Prototype Evaluation

In the following sections, the mechanical properties of the prototype Blastalloy TRIP 130 are preliminary evaluated. A 50 pound heat of Blastalloy TRIP 130 was ordered to make these assessments. The creation and processing of the alloy is discussed in Section 3.1. Section 3.2 briefly discusses the variation in the composition from the design. Sections 3.3, 3.4 and 3.5 detail the aging studies and subsequent mechanical testing to show that the η phase was thermodynamically suppressed, the strength goal was achieved, and the optimum austenite stability was met as described in Sections 2.3, 2.5, and 2.6.

3.1 Processing

The first heat of Blastalloy TRIP 130 was produced by Huntington Alloys Corporation of Special Metals Company in Huntington, W. Va., in collaboration with QuesTek Innovations. The alloy was cast as a best effort basis of the composition in Table 10 into a 50 lb, nominal 4.5 inch diameter ingot. The ingot was manufactured by using a vacuum induction melting (VIM) of pure, virgin elements. Following the solidification of the ingot, the surface is machine turned to remove the oxide layer and coated to minimize oxidation during homogenization and hot working. The ingot is homogenized at 1093° C. (2000° F.) for 6 hrs and after raising the temperature to 1204° C. (2200° F.), held for 18 hrs. After cooling to 1093° C. (2000° F.), the ingot is hot rolled into a plate with nominal final dimensions of 0.75 in by 7 in by length and air cooled. The resulting plate is then solution treated at 926° C. (1700° F.) for 1 hr and air cooled. The plate was delivered in the unaged condition. The rational for temperature selection for these processing steps was discussed in Section 2.8. The final weight of the finished plate is 32.5 lbs.

3.2 Composition Verification

Figure 62:
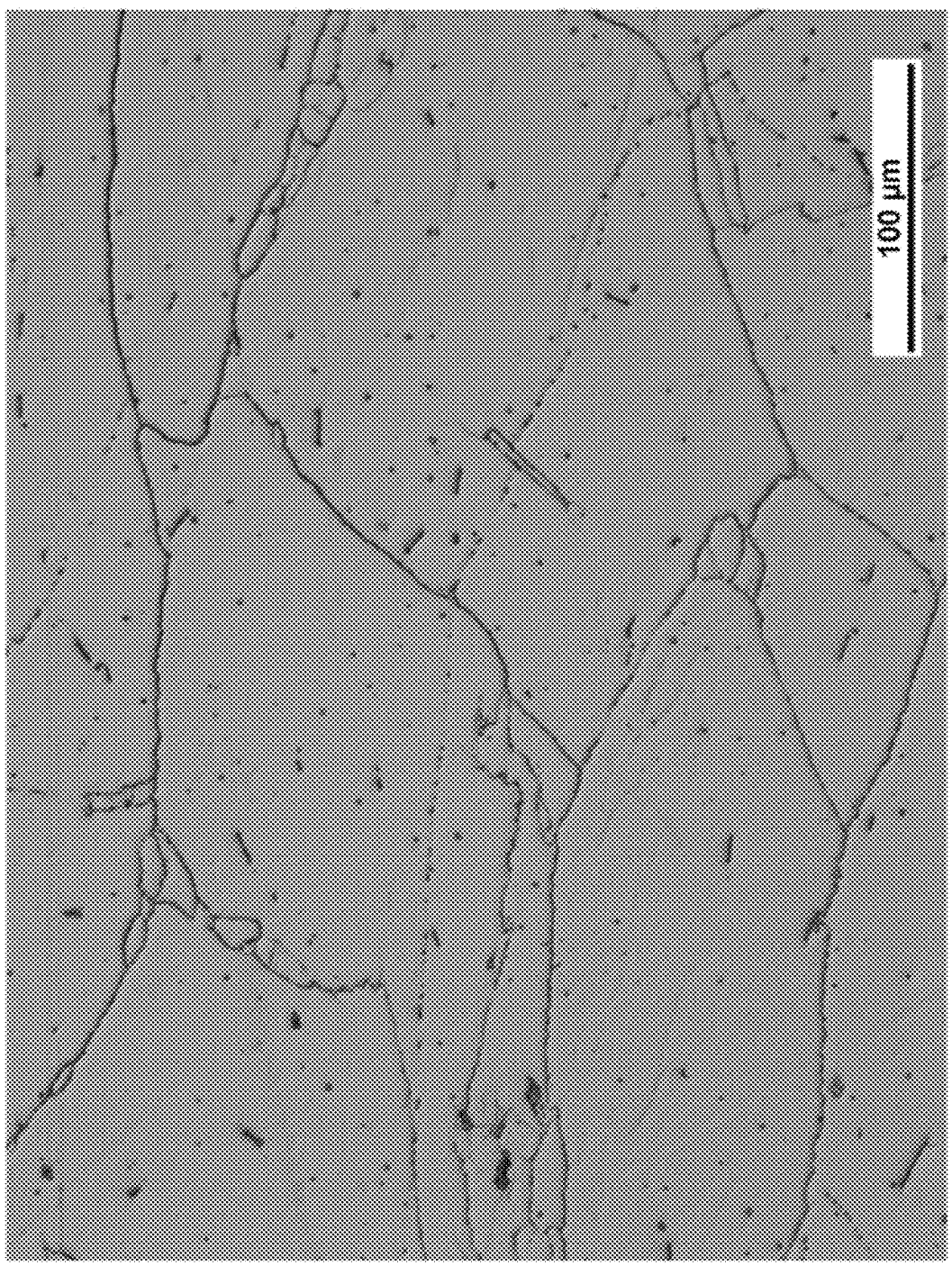
FIG. 62 shows an optical micrograph of the unaged, as received Blastalloy TRIP 130 showing the grain structure, according to one embodiment of the invention. Etched with 5% nital.

The composition of Blastalloy TRIP 130 was measured using inductively coupled plasma mass spectrometry for the metal elements and LECO combustion analysis for the non-metals by the Technology Processing Center at Huntington Alloys Corporation after casting and before homogenization and hot working. The measured composition as compared to the design composition is shown in Table 12.

methanol) for a few minutes to fully reveal the grain boundary structure. FIG. 62 shows the unaged, as received (homogenized, hot worked, and solution treated) microstructure.

Figure 57:
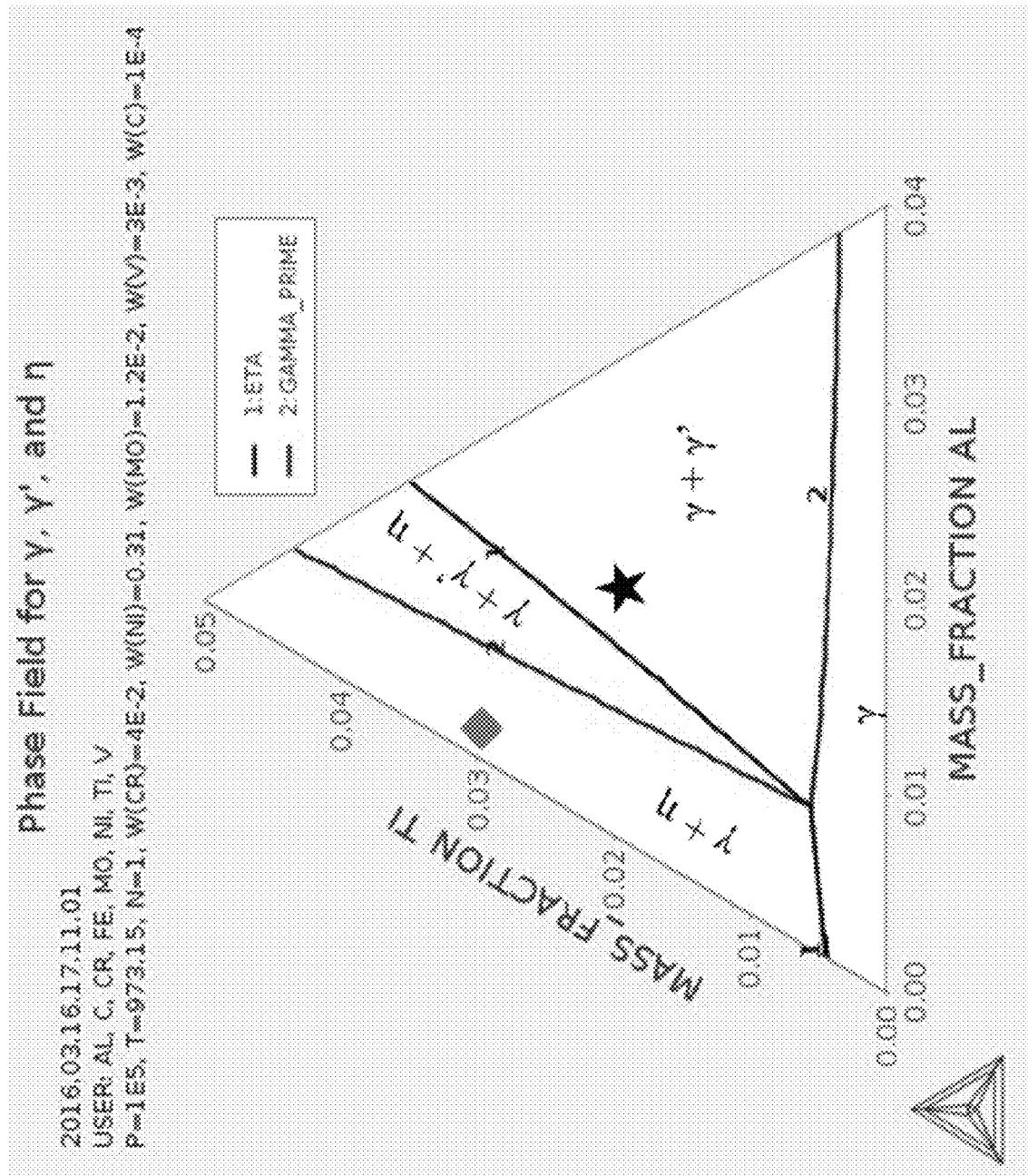
FIG. 57 shows a phasefield of Blastalloy TRIP 130 showing the designed composition as the black star and the composition for TRIP-180 is shown as the blue diamond, according to one embodiment of the invention.
Figure 63:
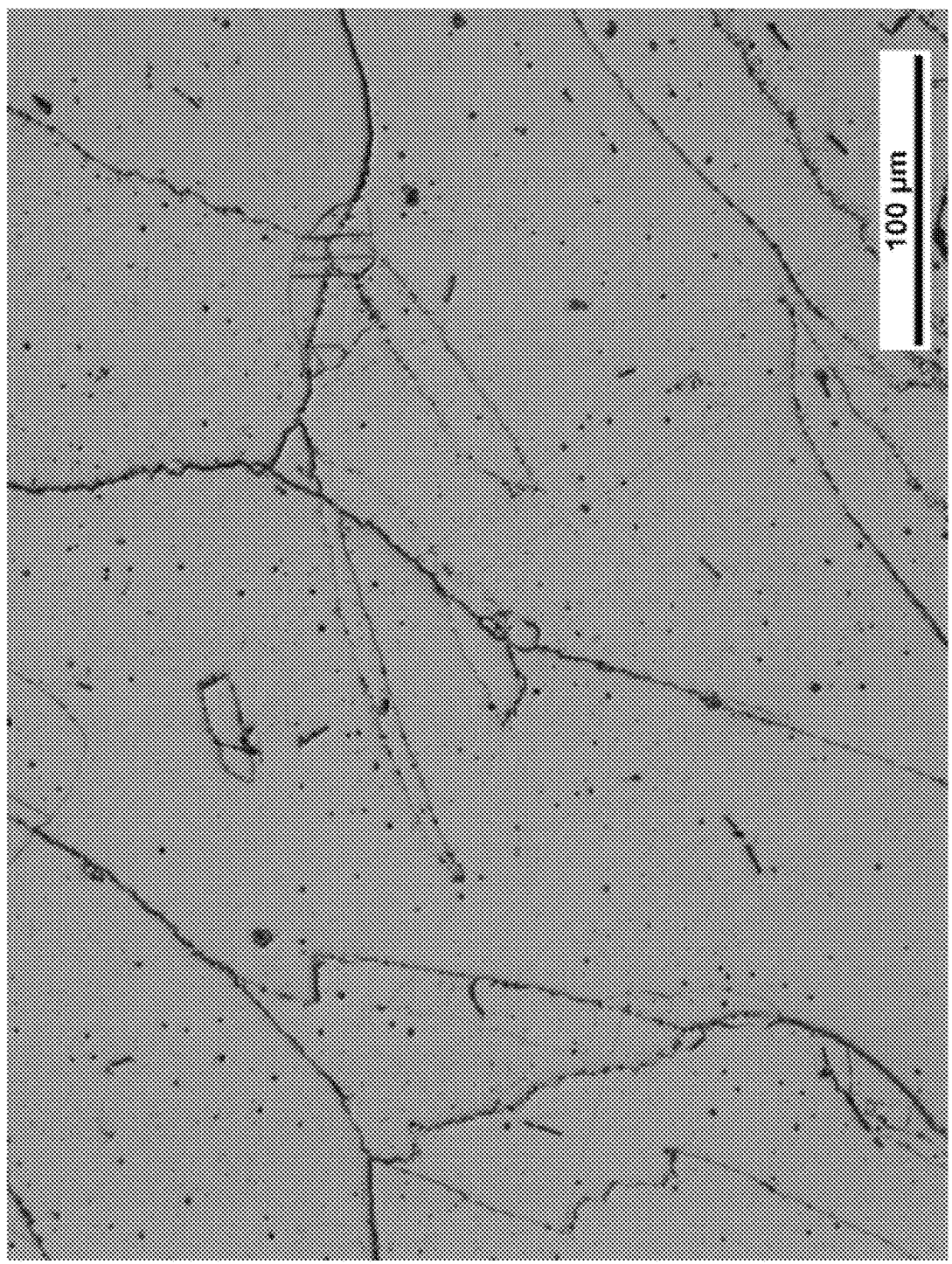
FIG. 63 shows an optical micrograph showing the lack of grain boundary η at long aging times in the microstructure of Blastalloy TRIP 130 aged for 60 hrs (2.5 days) at 700° C. Etched with 5% nital, according to one embodiment of the invention.

FIG. 63 shows microstructures of Blastalloy TRIP 130 aged for 60 hrs (2.5 days) at 700° C. The presence of the grain boundary cellular precipitation in TRIP-180 is not seen in either sample, nor was it seen in the check of microstructures at intermediate aging times. From the micrographs shown, the microstructure is seen to be fully austenitic with TiC carbides seen at the grain boundaries where the η grain boundary reaction has been successfully thermodynamically suppressed as deigned for in Section 2.3. This indicates that the γ', as seen in the phase field in FIG. 57, is the equilibrium phase in Blastalloy TRIP 130 and not metastable as in TRIP-180 where dislocations were added through warm working to provide potent nucleation sites for the γ'.

3.4 Strength Testing

An aging study was performed on Blastalloy TRIP 130 to determine the heat treating conditions that achieve 896 MPa (130 ksi) yield strength. The yield strength was approximated by performing Vickers microhardness measurements. The yield strength was calculated via the power law relationship for high strength steels shown in Equation (18) in MPa as a function of Vickers microhardness, HV.

$$\sigma_y = 0.7312 HV^{1.226} \tag{18}$$

Figure 64:
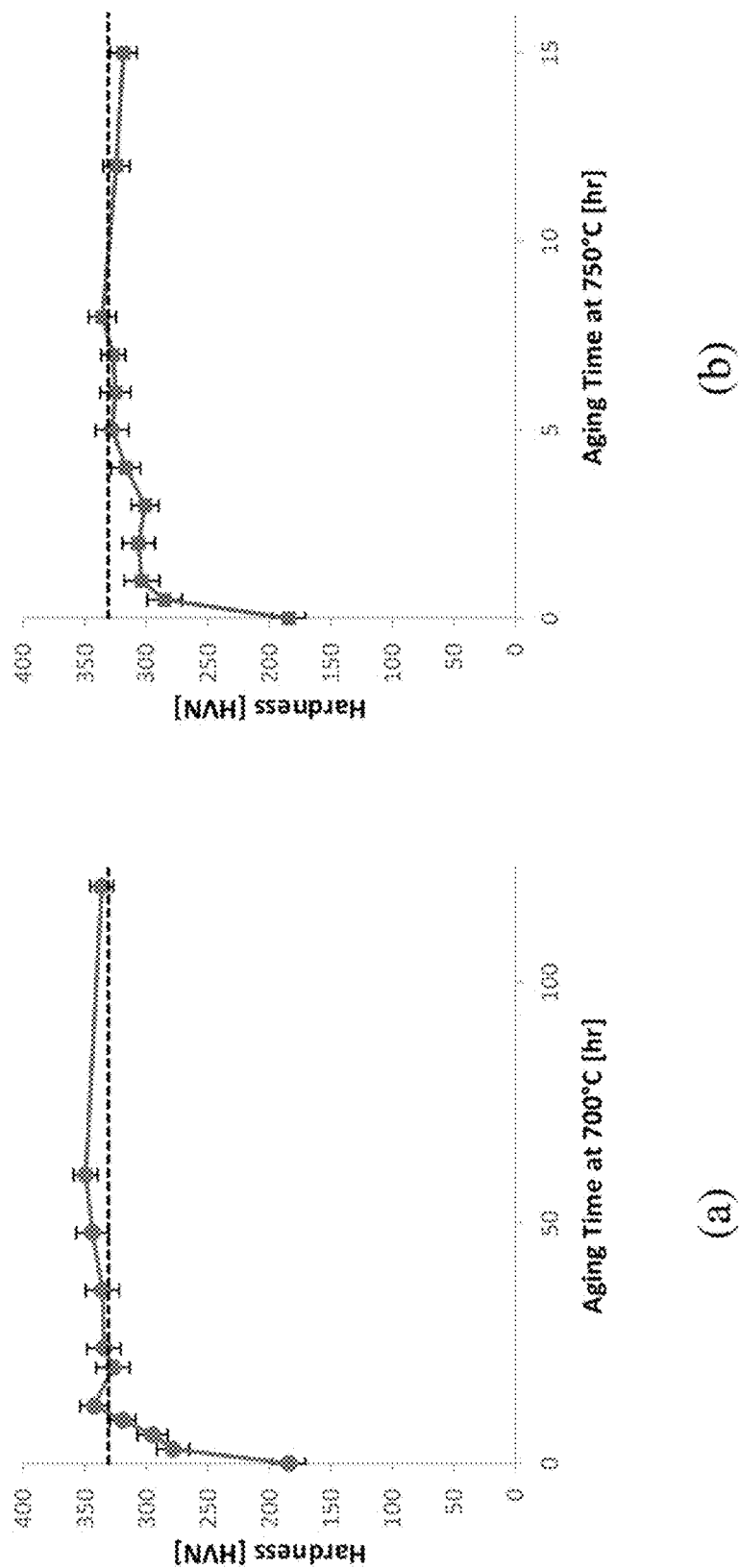
FIG. 64 shows Vickers microhardness of Blastalloy TRIP 130 aged at (a) 700 C and (b) 750 C with target hardness value indicated by the dashed line, according to one embodiment of the invention.
Figure 65:
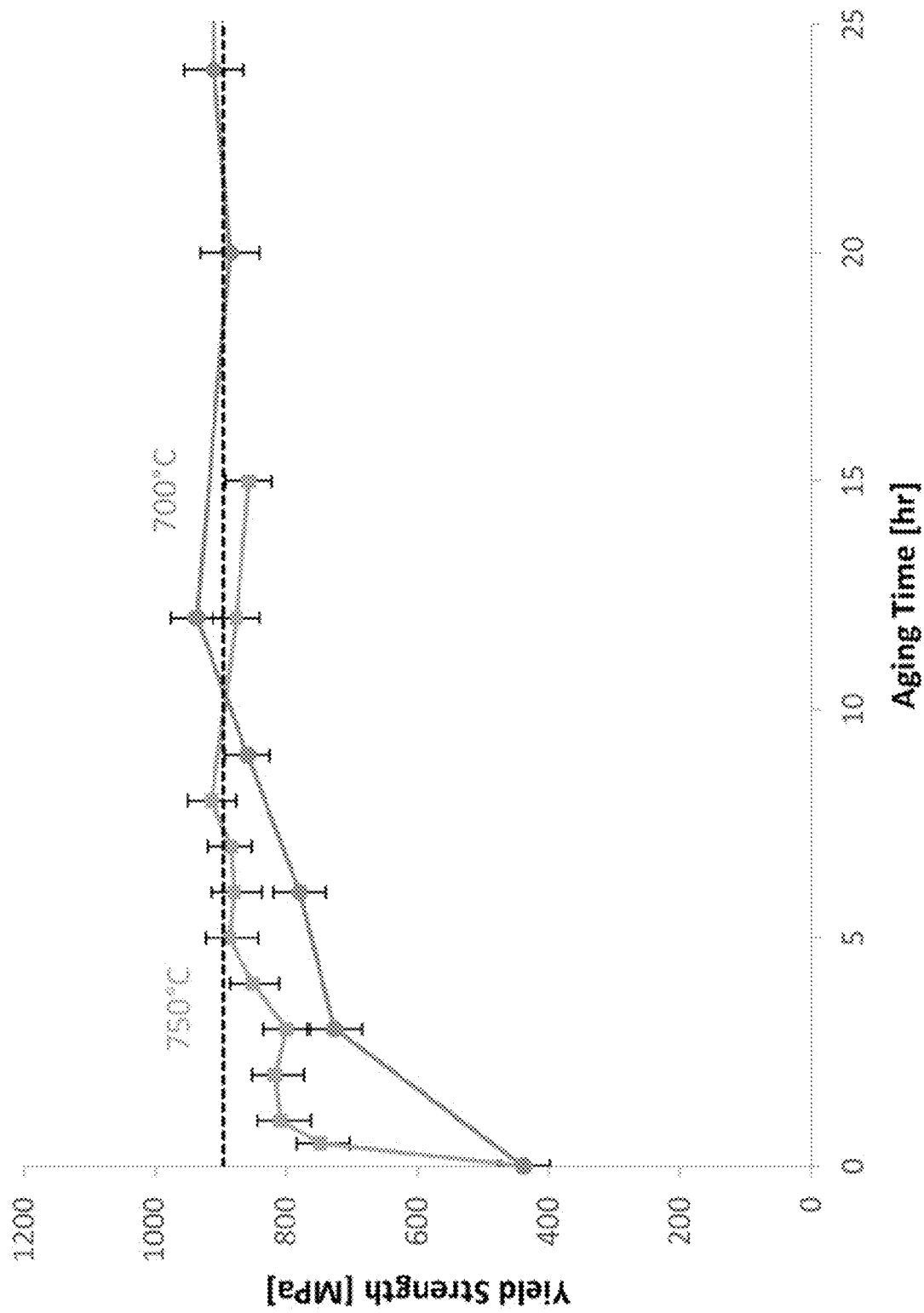
FIG. 65 shows a yield strength as calculated using Equation (18) for Blastalloy TRIP 130 aged at 700° C. (light blue) and 750° C. (orange) with target yield strength (896 MPa) indicated by the dashed line, according to one embodiment of the invention.

Following the process design in Section 2.8, initial samples were prepared for an aging study at 700° C. and 750° C. with a two step age (740° C. then 700° C.) following the conclusion of the isothermal aging study. During the course of the aging study, it was found that by 12 hrs at 700° C., rather than 116 hrs, Blastalloy TRIP 130 achieves the target strength of 896 MPa. Therefore, the two step age was not performed in order to simplify the processing of Blastalloy TRIP 130. FIG. 64 shows the results of the aging study. The profile in FIG. 64(a) shows that from 12 hrs to 120 hrs the hardness maintains similar values at or just above the target for aging at 700° C. Meanwhile aging at 750° C. achieves target hardness from 5 hrs to 12 hrs. FIG. 65 shows the conversion from hardness to yield strength by Equation (18), where the target strength of 896 MPa (130 ksi) is

TABLE 12

Blastalloy TRIP 130 designed composition, measured composition, and the percent difference in wt. %.

| | Ni | Cr | Ti | Al | Mo | V | C | B | Fe |
|---|---|---|---|---|---|---|---|---|---|
| Design | 28.93 | 4.0 | 2.03 | 1.23 | 1.2 | 0.3 | 0.01 | 0.0125 | Bal. |
| Measured | 29.09 | 4.10 | 2.00 | 1.24 | 1.22 | 0.4 | 0.013 | 0.01 | Bal. |
| Diff. | 0.55% | 2.5% | −1.5% | 0.81% | 1.8% | 33% | 30% | −20% | |

This shows that the actual measured composition very nearly matches the design composition for aluminum, titanium, and nickel with differences of less than 1.5%. The slight difference in weight percent vanadium, carbon, and boron (although large percent difference as their additions are so small) should not effect the design much.

3.3 η Suppression and Phase Stability

The presence, or lack thereof, of the grain boundary cellular precipitation of η was determined though optical microscopy on the longest tempered samples at each aging temperature. The samples shown in the following figures were etched with a 5% nital solution (5% nitric acid in indicated. Yield strength values calculated from hardness at 700° C. are shown in light blue and at 750° C. are shown in orange.

The differences between the predicted and observed aging behavior could result from a variety of factors. One aspect that was not incorporated into the design of Blastalloy TRIP 130, but was just calibrated for the composition of TRIP-180, is the misfit between the austenite matrix and the γ' precipitates. Using the TCNI8 database, the misfit in TRIP-180 was calculated to be 2.36% giving a critical radius for transition between coherent and incoherent precipitates to be 3.47 nm. Thermo-Calc calculates the misfit of Blastalloy TRIP 130 to be 0.95%. This would enable larger coherent γ' precipitates, which if using the same interfacial energies, yields a transition radius of 21.39 nm. Following that inquiry, a model for APBE was developed for variations in composition, but the interfacial energies and coherent strain energy were assumed to be constant. Another option is to incorporate a more specific mobility database for either steels or nickel based superalloys rather than the standard mobility database.

Figure 66:
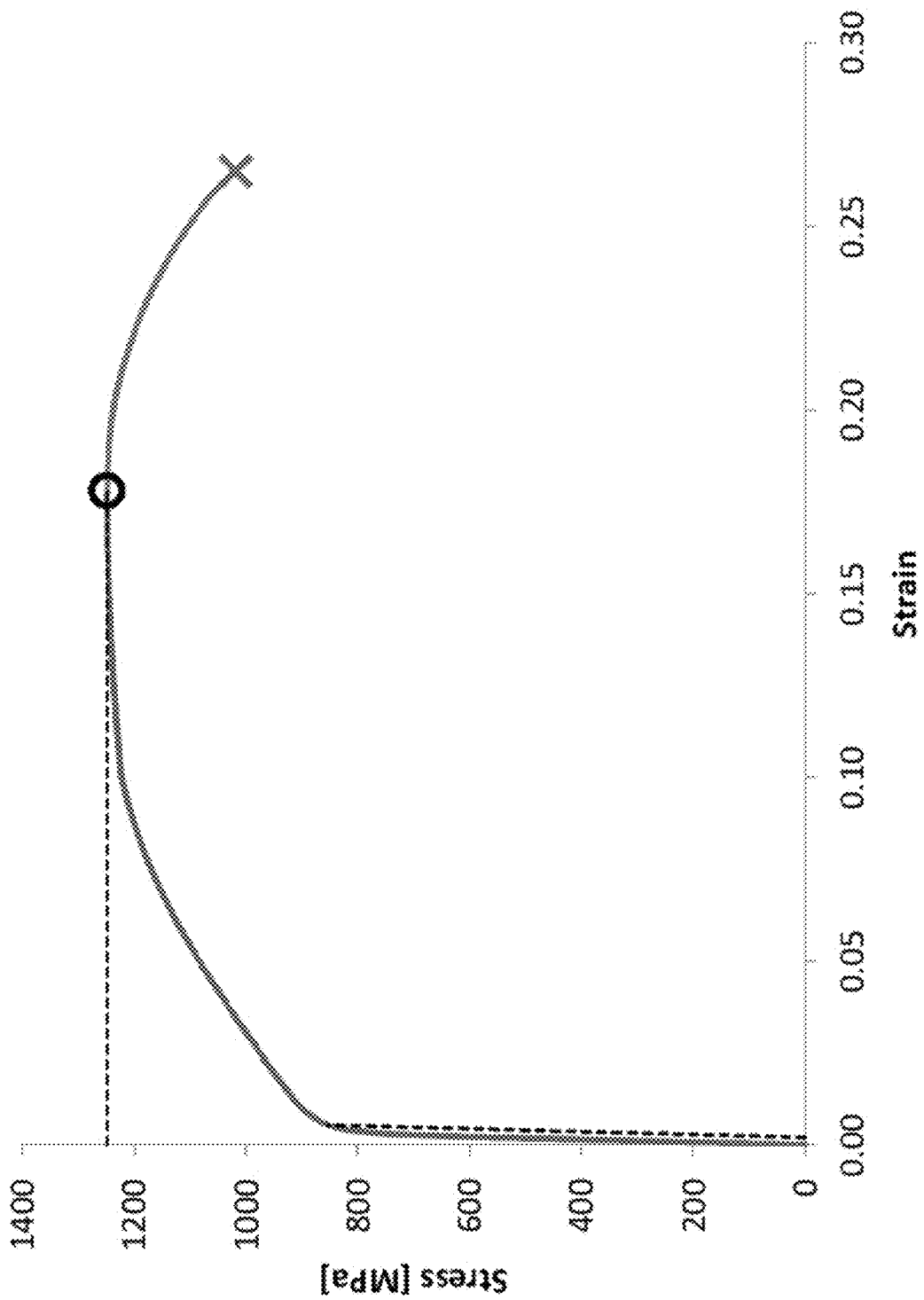
FIG. 66 shows a tensile stress-strain curve for Blastalloy TRIP 130 aged at 700° C. for 20 hrs, according to one embodiment of the invention. The dashed lines indicate yield strength and UTS calculations. The onset of necking is circled, and the red "X" indicates failure.

In order to validate the hardness to yield strength conversion in Equation (18), a room temperature tensile test was performed on a sample aged at 700° C. for 20 hrs. Of the samples tested for $M_s^°$(u.t.), the sample with that aging condition had the desired austenite stability as is discussed in Section 3.5. The results of the tensile test are shown in FIG. 66. The sample had a yield strength of 852 MPa (123.5 ksi) at a 0.2% offset, an ultimate tensile strength, UTS, of 1248 MPa (181 ksi), a Young's Modulus of 257 GPa, an elongation of 26.5% on a 18.6 mm gauge length, an uniform elongation of 17.6%, and a true failure strain of 61.3%. The failure strain and uniform strain were calculated by reduction in area measurements taken at failure and along the uniformly deformed gauge section. The onset of necking is confirmed in the true stress-strain curve in FIG. 67 where the change in stress equals the current stress level. This is given stated in the necking criterion by Backofen in Equation (19) [2].

$$\frac{d\sigma}{d\varepsilon} = \sigma \tag{19}$$

Figure 67:
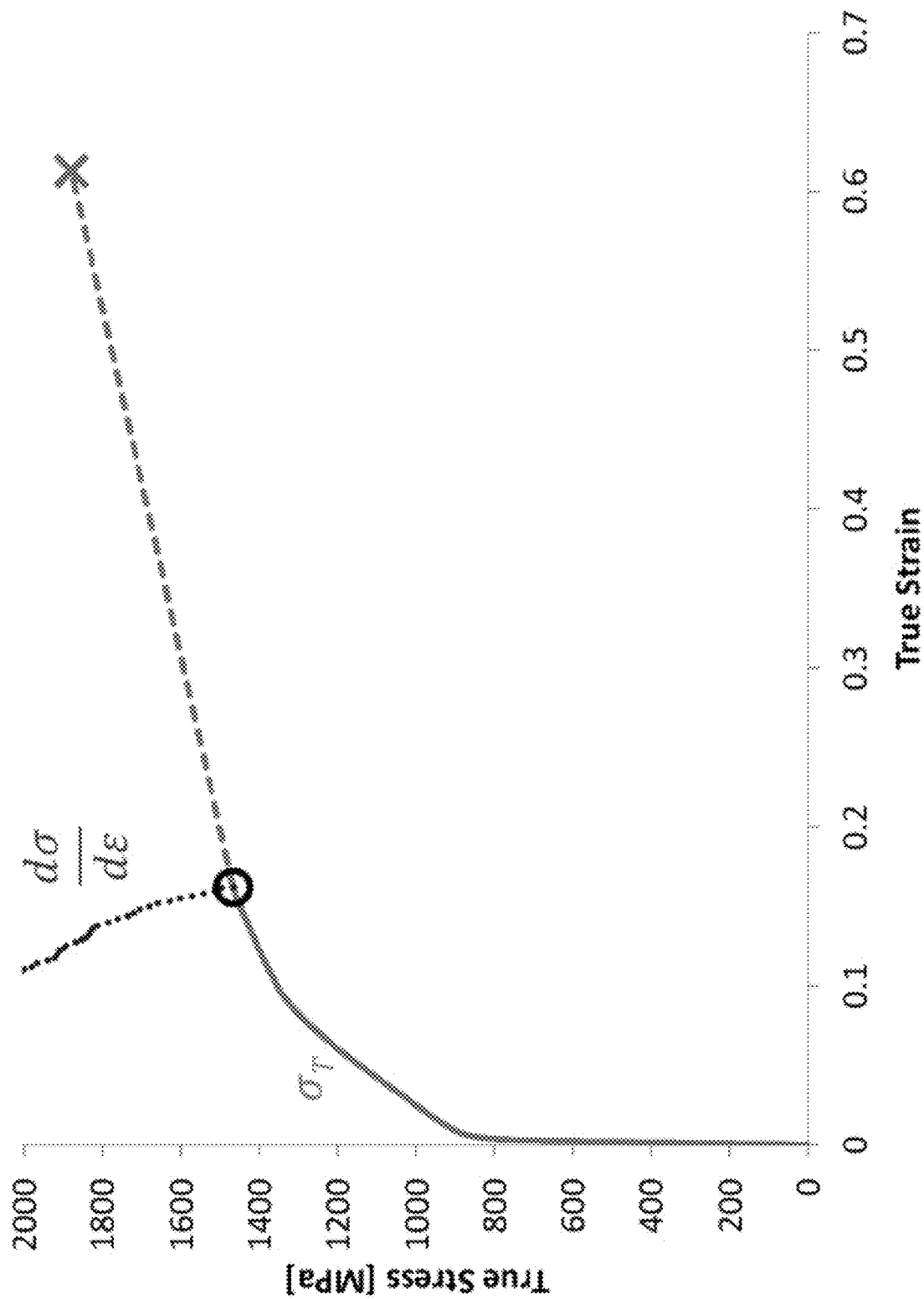
FIG. 67 shows true tensile stress-strain and dσ/dε curves for Blastalloy TRIP 130 aged at 700° C. for 20 hrs, according to one embodiment of the invention. The onset of necking is circled at the intersection of the two curves, and the red "X" indicates failure.

The true stress-strain in FIG. 67 initially shows slight upward curvature which is characteristic of transformation hardening when at temperatures above the $M_s^°$ temperature. As another confirmation of the lack of η phase, the reduction in area at failure of the neck, 45.8%, indicates no embrittling of the steel due to grain boundary cellular precipitation.

The designed for yield strength of 896 MPa was not achieved, even though the predicted yield strength from hardness did achieve the strength goal. This is because hardness correlates better to UTS, rather than yield strength, as hardness and UTS are indicators of a materials resistance to plastic deformation. When comparing Blastalloy TRIP 130 to QLT 10Ni, Blastalloy TRIP 130 exhibits a lower yield strength (852 MPa compared to 900 MPa), but has a higher UTS (1248 MPa compared to 1100 MPa) at a greater elongation (26.5% compared to 22.5%) [25]. The strain hardening behavior of Blastalloy TRIP 130 is seen to exceed QLT 10Ni with a difference in flow stress between the UTS and yield strength of approximately 400 MPa for Blastalloy TRIP 130 versus 200 MPa for QLT 10Ni. This is indicative of more effective utilization of transformation plasticity through the optimally stabilized austenite in Blastalloy TRIP 130 as compared to the dispersed austenite in QLT 10Ni. Therefore, even with a lower than designed for yield strength, Blastalloy TRIP 130 may still exhibit superior ballistic performance.

3.5 Austenite Stability Testing

In order to test for austenite stability, two quasi-static tensile specimens were cut and tested for $M_s^°$(u.t.). The samples were aged for 10 hrs and 20 hrs at 700° C. As seen in FIG. 64(a) the hardness, and thus yield strength, remains fairly constant at or above the target. From FIG. 65, at 700° C. Blastalloy TRIP 130 is expected to achieve the 896 MPa strength goal at 10 hrs and does achieve the goal at 20 hrs. This gives a spread of aging times at similar strength levels which have differing austenite stabilities.

Figure 68:
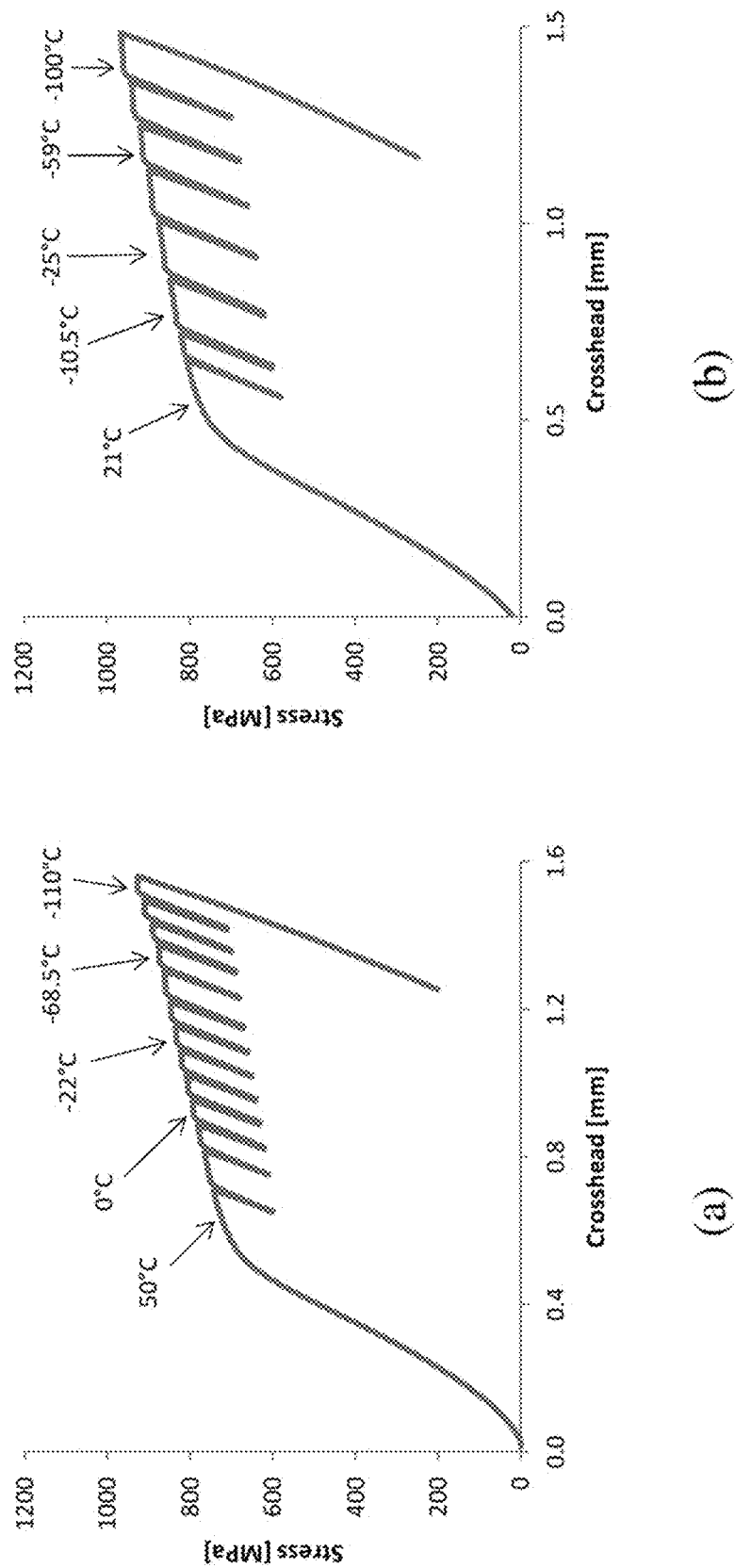
FIG. 68 shows a single specimen $M_s^\sigma$(u.t.) temperature tests for Blastalloy TRIP 130 aged at 700° C. for (a) 10 hrs. and (b) 20 hrs, according to one embodiment of the invention.

FIG. 68 shows the results of the two tests. This figure shows no evidence of the traditional inversion of the yield dependence at the $M_s^°$(u.t.) temperature as expected and shown previously in FIG. 35 for TRIP-180 and reported in the work of Feinberg, Sadhukhan, and Bolling and Richman among others [8, 18, 20]. This inversion occurs due to the change in the yielding behavior from slip of the austenite above the $M_s^°$ temperature in the strain-induced region to transformation of the austenite below the $M_s^°$ temperature in the stress-assisted region.

Figure 69:
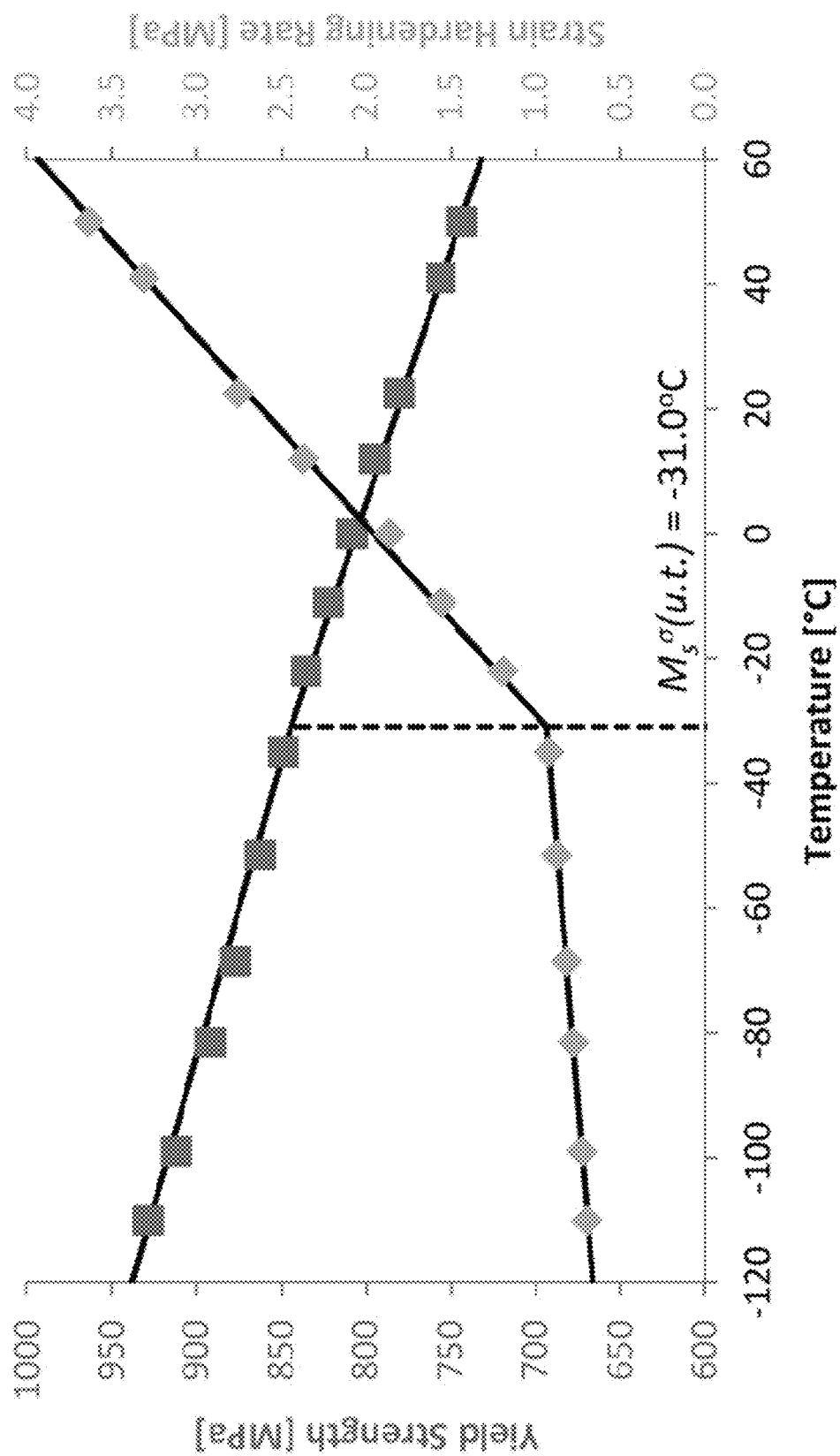
FIG. 69 shows yield strength (red) and strain hardening (orange) of Blastalloy TRIP 130 aged at 700° C. for 10 hrs from a single specimen $M_s^\sigma$(u.t.) test, according to one embodiment of the invention. The discontinuity in the slopes indicates the $M_s^\sigma$(u.t.) temperature of −31.0° C.
Figure 70:
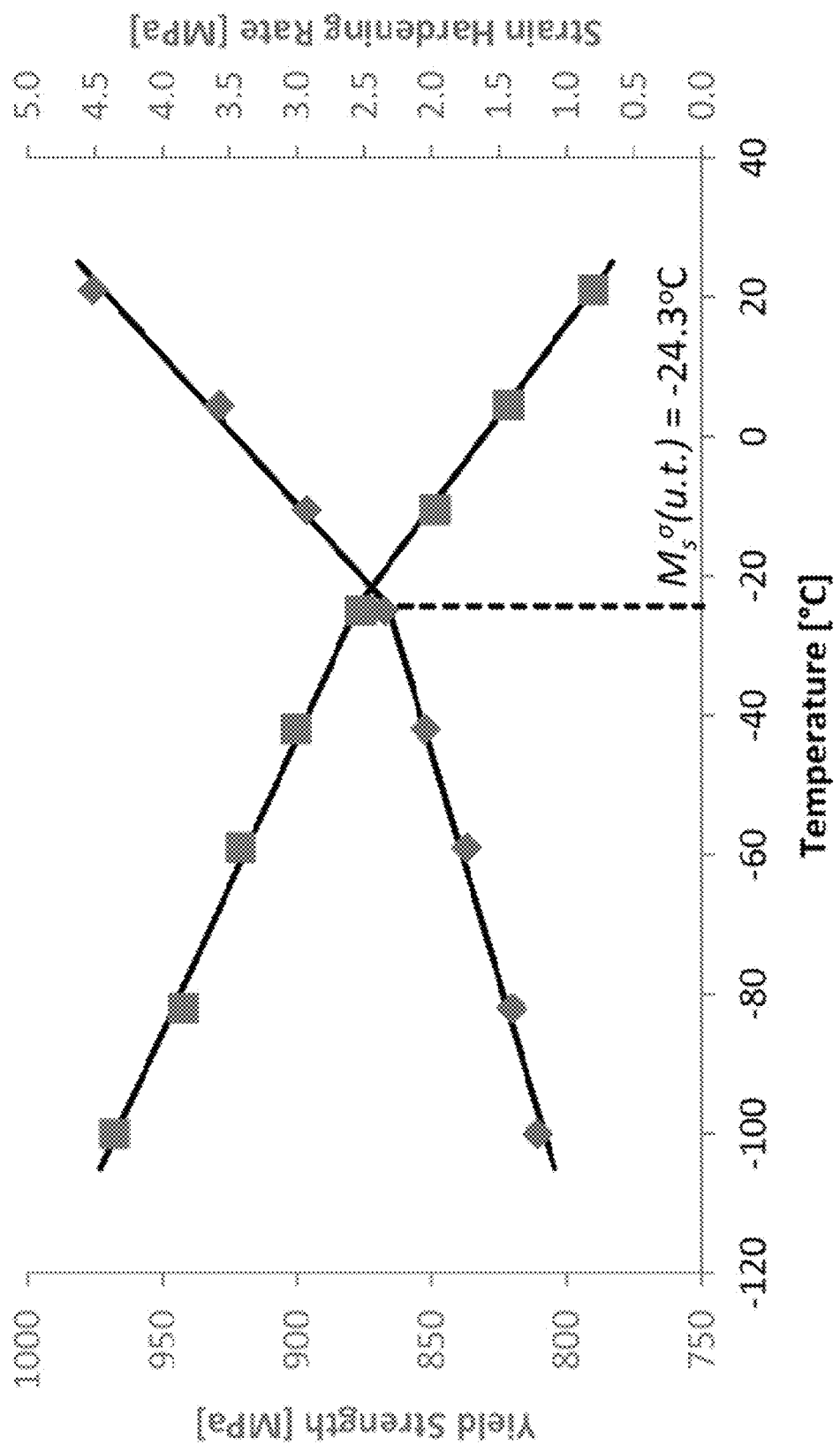
FIG. 70 shows yield strength (blue) and strain hardening (purple) of Blastalloy TRIP 130 aged at 700° C. for 20 hrs from a single specimen $M_s^\sigma$(u.t.) test, according to one embodiment of the invention. The discontinuity in the slopes indicates the $M_s^\sigma$(u.t.) temperature of −24.3° C.

Further inspection of the curves in FIG. 68 reveals that the strain hardening rate decreases from the higher temperature to lower temperature tests. FIGS. 69 and 70 show an analysis of the yield points and strain hardening rate (taken as the slope of the stress-strain curve post yield) for the samples aged for 10 hrs and 20 hrs, respectively. As with the previous samples tested for $M_s^°$(u.t.) temperature in Section 1.5, the yield strengths measured are calculated to determine the yield behavior as a function of temperature as each subsequent measurement also has strain hardening increment added from all previous tests on the single sample. The change of slope in the yield strength and strain hardening rate is attributed to change in yielding behavior where once below the $M_s^°$ temperature, the initial yielding by the stress-assisted martensitic transformation produces a strain softening and a thus a lower strain hardening rate. The data points from the 10 hr aged sample in FIG. 69 show a slight discontinuity in the yield strength between −25° C. and −50° C. and a large discontinuity in the strain hardening rate between −25° C. and −35° C. Calculation of linear best fit lines of each slope region for the yield strength and strain hardening rate suggest that the $M_s^°$(u.t.) temperature is approximately −31° C. Similarly, the data points from the 20 hr aged sample in FIG. 70 are analyzed and a discontinuity in both the yield strength and strain hardening rate is seen between −20° C. and −30° C. Calculation of the linear best fit lines produces a $M_s^°$(u.t.) temperature of −24.3° C. As expected, with additional aging, the austenite becomes more unstable and $M_s^°$(u.t.) increases.

Blastalloy TRIP 130 was designed for an austenite stability in shear where $M_s^°$(sh)=−40° C. and the corresponding austenite stability in uniform tension is $M_s^°$(u.t.)=−21.7° C. To calculate the $M_s^°$(sh) temperature from the measured $M_s^°$(u.t.) temperature, a range of $M_s^°$(u.t.) temperatures are predicted by varying the composition input. Where the $M_s^°$(u.t.) temperature equals −31.0° C. and −24.3° C., the $M_s^°$(sh) temperatures are also predicted. This produces a $M_s^°$(sh) temperature of −48.4° C. for the 10 hr aged sample and −42.0° C. for the 20 hr aged sample. The 20 hr aged sample achieves the designed austenite stability within 2° C.

3.6 Blastalloy TRIP 130 Design and Characterization Conclusions

The quantification of adiabatic shear localization resistance through the optimization of TRIP-180 defines the overarching parameters for the design of fully austenitic TRIP steels for fragment protection. By incorporating the need for a lower, optimum strength level and for the elimination of the η phase without warm working, more detailed constraints are placed on the processing, structure, and composition of this novel prototype design. Combining this knowledge with updated parametric models allowed for the design of a new prototype alloy, Blastalloy TRIP 130. The 130 signifies the yield strength goal of 130 ksi (896 MPa). The alloy is designed to thermodynamically suppress the η phase, achieve a peak strength of 896 MPa through γ' precipitation, and an austenite stability where $M_s^o(sh)=-40°$ C. given the austenite matrix composition at peak strength. The driving force difference between the γ' and η phases is −285 J/mol whereas for A-286 it is −830 J/mol. The radius, volume fraction, and APBE of the γ' precipitates at peak strengthening are 13.343 nm, 0.1473, 0.2489 J/mol providing a strength increase of 552 MPa. At this peak strengthening, the $M_s^o(sh)$ and $M_s^o(u.t.)$ temperatures are −40.0° C. and −21.7° C., respectively.

A 50 lb heat of this alloy was cast and processed according to the design specifications. The alloy closely matched the design composition, where the three major elements modified for the thermodynamic suppression, strengthening, and austenite stability were achieved with less than 1.5% difference from the design. The prototype alloy was preliminary evaluated, with performance meeting the design goals. At long aging times, there was no evidence of grain boundary cellular precipitation of η indicating that the γ' strengthening phase successfully achieved thermodynamic stability. Given a aging of 20 hrs at 700° C., rather than the predicted 116 hrs through PrecipiCalc, Blastalloy TRIP 130 has a yield strength of 852 MPa (123.5 ksi) and a $M_s^o(sh)$ temperature of −42° C. as predicted from a measured $M_s^o(u.t.)$ temperature of −24.3° C. Even though the yield strength did not meet the strength goal where $\sigma_y=896$ MPa, the strain hardening behavior via transformation hardening was seen to greatly outperform QLT 10Ni and resulted in a higher UTS given the yield strength. The optimum austenite stability where $M_s^o(sh)=-40°$ C. was achieved to be estimated within 2° C. and experimental error.

The austenite stability optimization and model calibration performed on TRIP-180 have enabled the successful design of Blastalloy TRIP 130 for a given stability at a 0.15 phase fraction of γ' to achieve a 896 MPa (130 ksi) yield strength. To extend this to higher strength levels, with a larger γ' phase fraction, the quantities of aluminum and titanium can be increased to attain a strength on the order of 1000 MPa (145 ksi). This could be achieved at phase fractions greater than 0.20 with weight fractions of aluminum and titanium of 0.02 and 0.03, respectively, or greater. A corresponding increase or decrease in nickel weight fraction to maintain optimum stability would also need to be incorporated. These parametric models have identified one optimum composition and the accompanying thermodynamic conditions to achieve strength and austenite stability goals.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1] A. J. Ardell and J. C. Huang. Antiphase boundary energies and the transition from shearing to looping.pdf. *Philosophical Magazine Letters*, 58(4):189-197, 1988.

[2] W. A. Backofen. Deformation processing. *Metallurgical Transactions B*, 4(December), 1972.

[3] D. Baither, C. Rentenberger, H. P. Karnthaler, and E. Nembach. Three alternative experimental methods to determine the antiphase-boundary energies of the gamma-prime precipitates in superalloys. *Philosophical Magazine A*, 82(9):1795-1805, 2002.

[4] L. M. Brown and G. R. Woolhouse. The loss of coherency of precipitates and the generation of dislocations. *Philosophical Magazine*, 21(170):329-345, February 1970.

[5] L. M. Brown and R. K. Ham. Dislocation-Particle Interactions. In A. Kelly and R. B. Nicholson, editors, *Strengthening Methods in Crystals*, pages 9-135. Elsevier Pub. Co., Amsterdam, N.Y., 1971.

[6] Morris Cohen. Unknowables in the essence of materials science and engineering. *Materials Science and Engineering*, 25:3-4, sep 1976.

[7] J. D. Eshelby. The Elastic Field Outside an Ellipsoidal Inclusion. *Proceedings of the Royal Society A: Mathematical, Physical and Engineering Sciences*, 252(1271): 561-569, October 1959.

[8] Zechariah Daniel Feinberg. *Design and Optimization of an Austenitic TRIP Steel for Blast and Fragment Protection*. PhD thesis, Northwestern University, 2012.

[9] R. K. Ham. Strengthening by Ordered Precipitates. In *Ordered alloys: structural applications and physical metallurgy*, pages 365-374. Claitor's Publishing Division, Baton Rouge, La., 1970.

[10] Dieter Isheim, David N. Seidman, and Nelia Wanderka. Doubly- and Triply-Charged Diatomic Molybdenum Cluster Ions As Observed in Pulsed-Laser Assisted Local-Electrode Atom-Probe (LEAP™) Tomography. *Microscopy and Microanalysis*, 13(Suppl 2):1650-1651, 2007.

[11] Takeshi Kawabata, Daisuke Shindo, and Kenji Hiraga. High-Resolution TEM Observations of Superdislocations in Ni3(Al, Ti). *Mater Trans (JIM)*, 33(6):565-570, 1992.

[12] H. Kolsky. An investigation of the mechanical properties of materials at very high rates of loading. *Proceedings of the Physical Society. Section B*, 62:676-700, 1949.

[13] By R Mises. Mechanics of solid bodies in the plastically-deformable state. *Math.-Phys. Klasse*, 4:1-10, 1913.

[14] V. Munjal and A. J. Ardell. Precipitation hardening of Ni-12.19 at. % Al alloy single crystals. *Acta Metallurgica*, 23:513-520, 1975.

[15] Gregory B. Olson and M. Azrin. Transformation behavior of TRIP steels. *Metallurgical and Materials Transactions A*, 9A(May):713-721, 1978.

[16] Gregory B. Olson. Computational Design of Hierarchically Structured Materials. *Science*, 277(5330):1237-1242, aug 1997.

[17] D. Raynor and J. M. Silcock. Strengthening Mechanisms in γ' Precipitating Alloys. *Metal Science*, 4(1):121-130, 1970.

[18] R. H. Richman and G. F. Bolling. Stress, deformation, and martensitic transformation. *Metallurgical and Materials Transactions B*, 2(September):2451-2462, 1971.

[19] Carl Richter and Ben A. van der Pluijm. Separation of paramagnetic and ferrimagnetic susceptibilities using low temperature magnetic susceptibilities and comparison with high field methods. *Physics of the Earth and Planetary Interiors*, 82(2):113-123, feb 1994.

[20] Padmanava Sadhukhan. *Computational Design and Analysis of High Strength Austenitic TRIP Steels for Blast Protection Applications*. PhD thesis, Northwestern University, 2008.

[21] Cyril Stanley Smith. *A Search for Structure*. The MIT Press, Cambridge, Mass., 1981.

[22] M. Vittori and A. Mignone. On the antiphase boundary energy of Ni3(Al, Ti) particles. *Materials Science and Engineering*, 74(1):29-37, 1985.

[23] Nicholas J. Wengrenovich and Gregory B. Olson. Optimization of a TRIP steel for adiabatic fragment protection. *Materials Today: Proceedings*, S2:S639-S642, 2015.

[24] Chune-Ching Young. *Transformation Toughening in PhosphoCarbide Strengthened Austenitic Steels*. PhD thesis, Massachusetts Institute of Technology, 1988.

[25] X. J. Zhang. Microhardness characterisation in developing high strength, high toughness and superior ballistic resistance low carbon Ni steel. *Materials Science and Technology*, 28(7):818-822, July 2012.

What is claimed is:

1. A method for designing an iron-based alloy, comprising:
   defining property objectives of the iron-based alloy, wherein the property objectives are design specifications of the iron-based alloy;
   designing a composition of the iron-based alloy according to the property objectives; and
   processing the composition to form the the iron-based alloy that meets the property objectives,
   wherein the iron-based alloy is an optimized Gamma-prime ($\gamma'$) strengthened austenitic transformation induced plasticity (TRIP) steel; and
   wherein the property objectives comprise a yield strength of 896 MPa (130 ksi), and a austenite stability designed to have $M_s^o(sh)=-40°$ C., $M_s^o(sh)$ being a temperature for shear.

2. The method of claim 1, wherein the property objectives further comprise a fragment simulating projectile (FSP) ballistic limit, $V_{50}>1.2*V_{50}^{baseline}$, a shear instability resistance, $\gamma_t^a>75\%$, a uniform tensile ductility, $\varepsilon_u>30\%$, and a fracture toughness, $K_{IC} \geq 90$ MPa/m$^{0.5}$.

3. The method of claim 2, wherein the composition comprises nickel (Ni) in a range of about 28.93±0.2 wt. %, chromium (Cr) in a range of about 4.0±0.2 wt. %, titanium (Ti) in a range of about 2.03±0.1 wt. %, aluminum (Al) in a range of about 1.23±0.05 wt. %, molybdenum (Mo) in a range of about 1.2±0.05 wt. %, vanadium (V) in a range of about 0.3±0.05 wt. %, C in a range of about 0.01±0.005 wt. %, boron (B) in a range of about 0.0125±0.005 wt. %, and iron (Fe) in balance.

4. The method of claim 3, wherein the optimized $\gamma'$ strengthened austenitic TRIP steel is Blastalloy TRIP 130.

5. The method of claim 4, wherein $\eta$ grain boundary cellular precipitation is thermodynamically eliminated, and a peak strength of 896 MPa is achieved through $\gamma'$ precipitation, and wherein the austenite stability designed to have $M_s^o(sh)=-40°$ C. is achieved given the austenite matrix composition at the peak strength.

6. The method of claim 4, wherein a driving force difference between the $\gamma'$ and $\eta$ phases is -285 J/mol.

7. The method of claim 4, wherein a volume fraction and a radius of the $\gamma'$ precipitates are controlled by tempering times and temperatures while an antiphase boundary energy (APBE) is a function of the composition of the $\gamma'$ precipitates.

8. The method of claim 7, wherein the radius, the volume fraction, and the APBE of the $\gamma'$ precipitates at peak strengthening are respectively 13.343 nm, 0.1473, 0.2489 J/mol providing a strength increase of 552 MPa from the $\gamma'$ precipitates.

9. The method of claim 8, wherein the strength increase is a function of the radius, the volume fraction, and the APBE.

10. The method of claim 1, wherein the step of defining the property objectives of the the iron-based alloy is implemented based on design specifications of one or more selected alloys, and experimental knowledge, computational predictions and empirical data from the one or more selected alloys.

11. The method of claim 10, wherein the step of designing the composition of the iron-based alloy is implemented based on designed compositions of the one or more selected alloys.

12. A method for designing an iron-based alloy, comprising:
   defining property objectives of the iron-based alloy, wherein the property objectives are design specifications of the iron-based alloy;
   designing a composition of the iron-based alloy according to the property objectives; and
   processing the composition to form the the iron-based alloy that meets the property objectives, wherein the step of processing the composition to form the iron-based alloy comprises:
   deoxidizing and melting the composition;
   solidifying the deoxidized and melted composition to form an ingot;
   homogenizing the ingot at a homogenization temperature, wherein the homogenization temperature is selected at a high enough temperature to promote fast diffusion, but below a temperature to prevent incipient melting;
   performing hot working for the ingot at a hot working temperature that is above its recrystallization temperature at which the ingot is plastically deformed;
   solution treating the ingot at a solution temperature, wherein the solution temperature is selected not only at a temperature above where the $\gamma'$ phase is in solution, but also where the grain refining titanium carbide phase is present, such that at the solution temperature, the only phases present are the austenite matrix and titanium carbide grain refiners;
   fast cooling the ingot; and
   tempering the ingot at a tempering temperature for a tempering time to form the iron-based alloy.

13. The method of claim 12, wherein to effectively model an extreme case of incipient melting during solidification as compared to equilibrium solidification, a Scheil simulation is performed using the Scheil module in Thermo-Calc, wherein the Scheil simulation implements the Scheil-Gulliver equation for solute redistribution during solidification.

14. The method of claim 12, wherein the homogenizing step is performed to ensure that the incipient melting does not occur.

15. The method of claim 12, wherein the titanium carbide phase allows for grain boundary pinning in order to maintain the grain structure achieved by the hot working.

16. The method of claim 12, wherein in order to determine the tempering time at 700° C. for Blastalloy TRIP 130 to reach peak strengthening and optimum austenite stability, the PrecipiCalc models are used to simulate precipitation kinetics of the $\gamma'$ precipitates, wherein at each timestep of output, the room temperature yield strength and the $M_s^o$ temperatures are calculated.

17. The method of claim 12, wherein to reduce the tempering time being less than about 20 hrs, a number of PrecipiCalc simulations are run at different tempering times to create precipitation predictions aligning time to peak strength to the tempering temperature, wherein the tempering temperature calculated to achieve peak strengthening at about 20 hr is about 738° C.

18. The method of claim 12, wherein to achieve the designed strength and austenite stability, the tempering step is performed at about 740° C. for about 18 hr, followed by a furnace cooling to at 700° C. for about 2 hr, wherein a yield strength of 887.6 MPa and a $M_s^\circ(sh)$ temperature of −39.5° C. are achieved.

* * * * *